US00RE50283E

(19) United States
(12) Reissued Patent
Auricchio et al.

(10) Patent Number: US RE50,283 E
(45) Date of Reissued Patent: Jan. 28, 2025

(54) EFFECTIVE DELIVERY OF LARGE GENES BY DUAL AAV VECTORS

(71) Applicant: Fondazione Telethon ETS, Rome (IT)

(72) Inventors: Alberto Auricchio, Naples (IT); Pasqualina Colella, Naples (IT); Ivana Trapani, Naples (IT)

(73) Assignee: FONDAZIONE TELETHON ETS (IT)

(21) Appl. No.: 17/541,846

(22) Filed: Dec. 3, 2021

Related U.S. Patent Documents

Reissue of:
(64) Patent No.: 10,494,645
Issued: Dec. 3, 2019
Appl. No.: 14/785,229
PCT Filed: Apr. 18, 2014
PCT No.: PCT/EP2014/058000
§ 371 (c)(1),
(2) Date: Oct. 16, 2015
PCT Pub. No.: WO2014/170480
PCT Pub. Date: Oct. 23, 2014

U.S. Applications:
(60) Provisional application No. 61/813,342, filed on Apr. 18, 2013.

(51) Int. Cl.
*C12N 15/86* (2006.01)
*A61K 48/00* (2006.01)
*C07K 14/705* (2006.01)

(52) U.S. Cl.
CPC ..... *C12N 15/86* (2013.01); *A61K 48/005* (2013.01); *C07K 14/705* (2013.01); *C12N 2750/14143* (2013.01); *C12N 2800/40* (2013.01); *C12N 2840/20* (2013.01); *C12N 2840/44* (2013.01); *C12N 2840/445* (2013.01)

(58) Field of Classification Search
CPC ..... C12N 15/86; C12N 2750/14143; C12N 2800/40; C12N 2840/20; C12N 2840/44; C12N 2840/445; A61K 48/005; C07K 14/705; A61P 27/02
See application file for complete search history.

(56) References Cited

U.S. PATENT DOCUMENTS 5,166,331 A 11/1992 Della Valle et al.
6,255,071 B1 * 7/2001 Beach ..... C07K 14/005 435/320.1
6,399,587 B1 6/2002 Mehtali et al.
6,808,922 B1 * 10/2004 Bebbington ..... C12N 15/63 424/93.1
6,846,970 B1 * 1/2005 Christou ..... C12N 15/8201 435/470
7,250,406 B2 * 7/2007 Tang ..... C07K 14/62 435/455
8,394,604 B2 3/2013 Liu et al.
10,214,572 B2 2/2019 Boye et al.
10,494,645 B2 12/2019 Auricchio et al.
2004/0142884 A1 7/2004 Tang et al.
2005/0101582 A1 5/2005 Lyons et al.
2005/0181017 A1 8/2005 Hughes et al.
2005/0250737 A1 11/2005 Hughes et al.
2005/0281861 A1 12/2005 Hughes et al.
2006/0105953 A1 5/2006 Lacoste et al.
2006/0141049 A1 6/2006 Lyons et al.
2006/0182783 A1 8/2006 Hughes et al.
2007/0059336 A1 3/2007 Hughes et al.
2007/0224278 A1 4/2007 Lyons et al.
2008/0241252 A1 10/2008 Lyons et al.
2009/0149435 A1 6/2009 Wang et al.
2009/0215172 A1 8/2009 Schnidt et al.
2009/0082321 A1 9/2009 Edelman et al.
2010/0003218 A1 1/2010 Duan et al.
2010/0209414 A1 8/2010 Schmidt et al.
2014/0256802 A1 * 9/2014 Boye ..... C07K 14/47 514/44 R
2016/0076054 A1 3/2016 Auricchio et al.
2018/0327779 A1 11/2018 Colella et al.
2021/0371878 A1 12/2021 Auricchio et al.
2022/0002749 A1 1/2022 Colella et al.
2022/0389450 A1 12/2022 Auricchio et al.

FOREIGN PATENT DOCUMENTS

CA 2909733 A1 10/2014
CN 1279723 A 1/2001
CN 102282255 A 12/2011
EP 0356130 A2 2/1990
EP 3265571 B1 1/2018
JP H02-124094 A 5/1990
JP 2002-511751 A 4/2002
JP 2007-209227 A 8/2007
JP 2012-531191 A 1/2011
(Continued)

OTHER PUBLICATIONS

Esposito et al., Liver gene therapy with intein-mediated F8 thans-splicing corrects mouse Haemophilia A, EMBO Molecular Medicine, 2022, 14: e15199.
Padula et al., Full-length ATP7B reconstituted through protein trans-splicing corrects Wolson disease in mice, Molecular Therapy: Methods and Clinicla Development, Sep. 2022, 26: 495-504.
Tornabene et al., 240. Inclusion of a degron reduces levels of undesired inteins after AAV-mediated protein trans-splicing in the retina, Molecular Therapy, New Technologies Advancing Gene Therapy for Neurologic Diseases, Apr. 27, 2021, 29(4S1): 125-126 (Abstract).
Tornabene et al., 931. Selective Intein Degradation for safe AAV Mediated Large Gene Delivery, Molecular Therapy, New Techniques in Gene Therapy for Neurologic Disorders, Apr. 28, 2020, 28(4S1): 402-403 (Abstract).
(Continued)

*Primary Examiner* — Padmashri Ponnaluri
(74) *Attorney, Agent, or Firm* — LATHROP GPM LLP; James H. Velema, Esq.

(57) ABSTRACT

The present invention relates to constructs, vectors, relative host cells and pharmaceutical compositions which allow an effective gene therapy, in particular of genes larger than 5 Kb.

55 Claims, 15 Drawing Sheets

Figure 1:
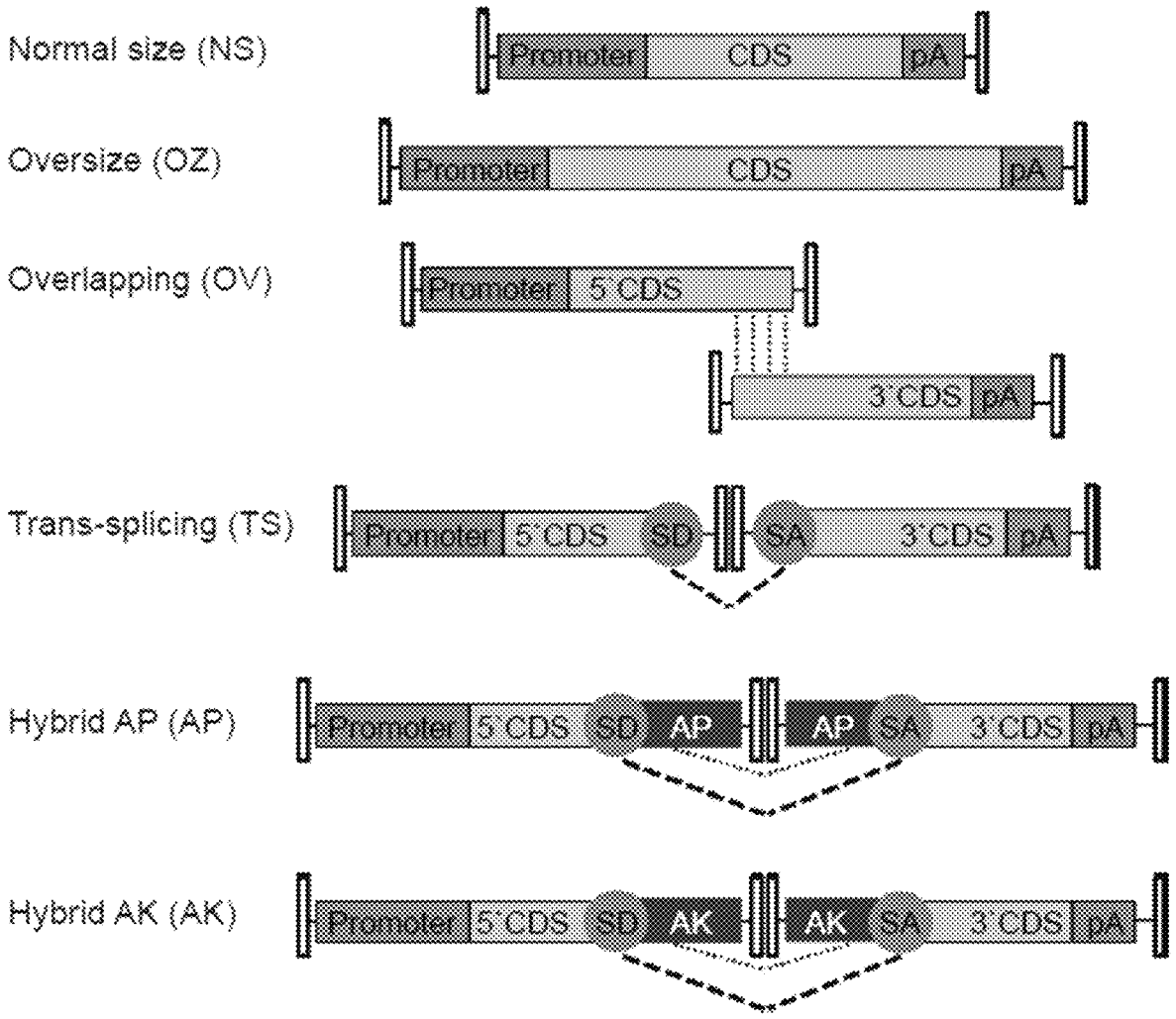

Specification includes a Sequence Listing.

(56) References Cited

FOREIGN PATENT DOCUMENTS

| | | | |
|---|---|---|---|
| WO | WO 1999/015683 | A1 | 4/1999 |
| WO | WO 1999/041397 | A1 | 8/1999 |
| WO | WO 2001/029243 | A1 | 4/2001 |
| WO | WO 2001/079518 | A2 | 10/2001 |
| WO | WO 2004/025264 | A2 | 3/2004 |
| WO | 2008106644 | | 9/2008 |
| WO | WO 2008/106644 | A2 | 9/2008 |
| WO | 2009103562 | | 8/2009 |
| WO | WO 2009/103562 | A1 | 8/2009 |
| WO | WO 2010/048086 | A1 | 4/2010 |
| WO | WO 2010/059763 | A1 | 5/2010 |
| WO | WO 2011/000929 | A1 | 1/2011 |
| WO | WO 2013/045632 | A1 | 4/2013 |
| WO | 2013075008 | | 5/2013 |
| WO | WO 2013/075008 | A1 | 5/2013 |
| WO | WO 2014/170480 | A1 | 10/2014 |
| WO | WO 2015/054653 | A2 | 4/2015 |
| WO | WO 2015/121501 | A1 | 8/2015 |
| WO | WO 2016/139321 | A1 | 9/2016 |
| WO | WO 2016/146757 | A1 | 9/2016 |
| WO | WO 2017/019994 | A2 | 2/2017 |
| WO | WO 2017/132580 | A2 | 8/2017 |
| WO | WO 2017/216560 | A1 | 12/2017 |
| WO | WO 2018/071868 | A1 | 4/2018 |
| WO | WO 2018/160582 | A1 | 9/2018 |

OTHER PUBLICATIONS

Tornabene et al., Inclusion of a degron reduces levels of undesired inteins after AAV-mediated protein trans-splicing in the retina, Mol Ther.: Methods and Clinical Development, Dec. 2021, 23: 448-459.
Tornabene et al., Intein-mediated protein trans-splicing expands adeno-associated virus transfer capacity in the retina, Sci Transl Med., May 15, 2019, 11(492): 1-30.
Hill et al., "Nucleotide Sequence of Bacteriophage f1 DNA", *Journal of Virology*, 1982, 44: 32-46.
International Search Report for International Patent Application No. PCT/EP2014/058000, mailed Jul. 21, 2014, 5 pages.
Allikmets R., A photoreceptor cell-specific ATP-binding transporter gene (ABCR) is mutated in recessive Stargardt macular dystrophy, Nature Genetics, 1997, vol. 15(3) pp. 236-246 & Erratum published in Nature Genetics. 1997, vol. 17(1), 122.
Auricchio A et al, Exchange of surface proteins impacts on viral vector cellular specificy and transduction characteristics: the retina as a model. (2001) Human Molecular Genetics., 10(26):3075-3081.
Auricchio, A. J. Smith, R. R. Ali, The Future Looks Brighter After 25 Years of Retinal Gene Therapy, Human Gene Therapy, 2017, vol. 28(11), pp. 982-987.
Bennicelli J, et al Mol Ther. Jan. 22, 2008; Reversal of Blindness in Animal Models of Leber Congenital Amaurosis Using Optimized AAV2-mediated Gene Transfer, Mar. 2008, vol. 16, No. 3, pp. 458-465.
Bothwell et al. (1981) Heavy chain variable region contribution to the NPb family of antibodies: somatic mutation evident in a γ2a variable region, Cell 24, pp. 625-637.
Bungert S, L. L. Molday, R. S. Molday, Membrane topology of the ATP binding cassette transporter ABCR and its relationship to ABC1 and related ABCA transporters: identification of N-linked glycosylation sites, J Biol Chem 276(26), 23539-23546 (2001).
Bunting, S., et al., Gene Therapy with BMN 270 Results in Therapeutic Levels of FVIII in Mice and Primates and Normalization of Bleeding in Hemophilic Mice. Mol Ther, 2018. 26(2): p. 496-509.
Cheriyan M, S. H. Chan, F. Perler, Traceless splicing enabled by substrate-induced activation of the Nostoc punctiforme Npu DnaE intein after mutation of a catalytic cysteine to serine, J Mol Biol 426(24), 4018-4029 (2014).
Cho et al., A degron created by SMN2 exon 7 skipping is a principal contributor to spinal muscular atrophy severity, Genes and Development, Mar. 1, 2010, 24(5): 438-442.
Colella P et al., "Efficient gene delivery to the cone-enriched pig retina by dual AAV vectors", Gene Therapy, Apr. 1, 2014, vol. 21 No. 4, pp. 450-456 XP055270423 https://www.nature.com/articles/gt20148.
Dalkara D et al., In vivo-directed evolution of a new adeno-associated virus for therapeutic outer retinal gene delivery from the vitreous, Sci Transl Med. Jun. 12, 2013;5(189):189ra76.
Devereux J et al., A comprehensive set of sequence analysis programs for the VAX, Nucl. Acid Res., 12:387-395 (1984).
Donello J E, J. E. Loeb, T. J. Hope, Woodchuck hepatitis virus contains a tripartite posttranscriptional regulatory element, J Virol 72, 5085-5092 (1998).
Doria M, A. Ferrara, A. Auricchio, AAV2/8 vectors purified from culture medium with a simple and rapid protocol transduce murine liver, muscle, and retina efficiently, Hum Gene Ther Methods 24 (6), 392-398 (2013).
Drivas T G., E. L. Holzbaur, J. Bennett, Disruption of CEP290 microtubule/membrane-binding domains causes retinal degeneration, J Clin Invest 123(10), 4525-4539 (2013).
Duan et al., Expanding AAV Packaging Capacity with Trans-slicing or Overlapping Vectors: A Quantitiative Comparison, the Journal of the American Society of Gene Therapy, vol. 4, No. 4, pp. 383-391 (2001).
Dyka F M et al., Dual adeno-associated virus vectors result in efficient in vitro and in vivo expression of an Oversized Gene, MYO7A, Human Gene Therapy Methods, Apr. 1, 2014, vol. 25, No. 2, pp. 166-177.
Esumi N, et al., Analysis of the VMD2 Promoter and Imlications of E-box Binding Factors in its Regulation, J. Biol. Chem. vol. 279, No. 18, pp. 19064-19073 (2004).
FDA approves hereditary blindness gene therapy. Nat Biotechnol 36, 6 (2018).
Flotte TR. Adeno-associated virus-based gene therapy for inherited disorders. Pediatr Res. Dec. 2005;58(6):1143-7.
Gao G et al., Purification of recombinant adeno-associated virus vectors by column chromatography and its performance in vivo, Human Gene Therapy, 2000, 11(15), 2079-2091.
Ghosh et al. (2008), A hybrid vector system expands adeno-associated viral vector packaging capacity in a transgene-independent manner, Molecular Therapy Jan. 2008, 16(1): 124-130.
Gibbs D, et al., Function of MYO7A in the Human RPE and the Validity of Shaker1 Mice as a Model for Usher Syndrome 1B, Invest. Ophthalmol. Vis. Sci. 2010, 51, 1130-1135.
Gilon et al., Degradation signals for ubiquitin system proteolysis in *Saccharomyces cerevisiae*, EMBO J., May 15, 1998, 17(10): 2759-2766.
Goncalves MA. Adeno-associated virus: from defective virus to effective vector, Virol J. May 6, 2005;2:43-60.
Grimm et al. (1998) Novel Tools for Production and Purification of Recombinant Adeno associated Virus Vectors, Hum. Gene Ther, pp. 2745-2760.
Hasson T et al., Expression in cochlea and retina of myosin VIIa, the gene product defective in Usher syndrome type 1B, Proc. Natl Acad Sci USA, 1995, vol. 92, 9815-9819.
Hickey DG et al., Tropism of engineered and evolved recombinant AAV serotypes in the rd1 mouse and ex vivo primate retina, Gene Therapy Dec. 2017;24(12):787-800.
International Search Report and Written Opinion for PCT International Patent Application No. PCT/EP2016/054602, mailed Jul. 20, 2016.
International Search Report and Written Opinion for PCT International Patent Application No. PCT/EP2019-078020, mailed May 14, 2020.
Iwai H, S. Zuger, J. Jin, P. H. Tam, Highly efficient protein trans-splicing by a naturally split DnaE intein from Nostoc punctiforme, FEBS Letters, 2006, 580(7), pp. 1853-1858.
Iwamoto M et al., A general chemical method to regulate protein stability in the mammalian central nervous system, Chem Biol. Sep. 24, 2010; 17(9): 981-988.
Jansen M et al., Role of ORPs in sterol transport from plasma membrane to ER and lipid droplets in mammalian cells, Traffic 2011, vol. 12(2), pp. 218-231.

(56) References Cited

OTHER PUBLICATIONS

Karlin S and Altschul S F, Applications and statistics for multiple high-scoring segments in meolcular sequences, Proc Natl Acad Sci USA, Jun. 1993, vol. 90, pp. 5873-5877.
Karlin S and Altschul S F, Methods for assessing the statistical significant of molecular sequence features by using general scoring schemes, Proc Natl Acad Sci USA, 1990, vol. 87, pp. 2264-2268.
Khani S C et al., AAV-mediated expression targeting of rod and cone photoreceptors with a human rhodopsin kinase promoter, Invest Ophthalmol Vis Sci, vol. 48(9), pp. 3954-3961 (2007).
Klimczak R R et al., A novel adeno-associated viral variant for efficient and selective intravitreal transduction of rat Müller cells, PLoS One. Oct. 14, 2009;4(10):e7467.
Levitt N et al., Definition of an efficient synthetic poly(A) site. Genes Dev. Jul. 1989;3(7):1019-1025.
Li et al "Protein Trans-Splicing as a means for viral vector-mediated in vivo gene therapy", Human Gene Therapy, Sep. 1, 2008, vol. 19, No. 9, pp. 958-964.
Li Y, Split-inteins and their bioapplications , Biotechnol Letters, 2015, 37, 2121-2137.
Liang F-Q et al. (2000) Intraocular Delivery of Recombinant Virus, in Methods in Molecular Medicine, vol. 47: Vision Research Protocols edited by P E Rakoczy, Humana Press, V pp. 125-139.
Lilley, D.M. and Dahlberg, J.E. (1992) Methods in Enzymology: DNA Structures Part A: Synthesis and Physical Analysis of DNA, Academic Press.
Liu X Q et al., A DnaB intein in Rhodothermus marinus: Indication of recent intein homing across remotely related organisms, Proc Natl Acad Sci USA, Jul. 22, 1997;94(15):7851-6.
Liu X, et al. Myosin Vlla, the product of the Usher 1B syndrome gene, is concentrated in the connecting cilia of photoreceptor cells, Cell. Motil. Cytoskeleton, 1997, 37, 240-252 (1997).
Liu Y-L et al.(2003) Optimized Production of High-Titer Recombinant Adeno-associated Virus in Roller Bottles, Biotechniques 34(1): 184-189.
Lockless S W, T. W. Muir, Traceless protein splicing utilizing evolved split inteins, Proc Natl Acad Sci USA, 2009, vol. 106, pp. 10999-11004.
Lostal et al., Full-Length Dystrophin Reconstitution with Adeno-Associated Viral Vectors, Human Gene Therapy, Jun. 2014, 25: 552-562.
Ma S L et al. (2015) Whole Exome Sequencing Reveals Novel PHEX Splice Site Mutations in Patients with Hypophosphatemic Rickets, PLoS One 10(6): p. e0130729.
Maddalena S et al., Triple Vectors Expand AAV Transfer Capacity in the Retina, Mol Ther 2018, vol. 26, pp. 524-541.
Madeira F et al., (2019) The EMB:-EBI search and seqeunce analysis tools API in 2019. Nucleic Acids Research, 47(W1), pp. W636-W641.
Mandel RJ, Manfredsson FP, Foust KD, Rising A, Reimsnider S, Nash K, Burger C. Recombinant adeno-associated viral vectors as therapeutic agents to treat neurological disorders. Mol Ther. Mar. 2006;13(3):pp. 463-483.
Mata N L et al., Invest Ophthalmol Vis Sci, 2001, vol. 42, pp. 1685-1690.
McIntosh J et al., Therapeutic levels of FVIII following a single peripheral vein administration of rAAV vector encoding a novel human factor VIII variant, Blood Feb. 20, 2013, 121(17):3335-3344.
Millan J M, et al., An update on the genetics of usher syndrome, J. Ophthalmol. 2011, vol. 2011, 417217.
Mills K V, M. A. Johnson, F. B. Perler, Protein Splicing: How Inteins Escape from Precursor Proteins, J Biol Chem 289, 2014, 14498-14505.
Mussolino C et al., AAV-mediated photoreceptor transduction of the pig cone-enriched retina, Gene Ther 2011, vol. 18, pp. 637-645.
Nakano T et al., Self-formation of optic cups and storable stratified neural retina from human ESCs , Cell Stem Cell 2012, vol. 10, pp. 771-785.
Nathwani A C et al. (2006) Self-complementary adeno-associated virus vectors containg a novel liver-specific human factor OX expression cassette enable highly efficient transduction of murine and non-human primate liver, Blood 107: 2653-2661.
NIH National Library of Medicine, Bacteriophage f1, complete genome, GenBank Database Accession No. J02448.1, Apr. 27, 1993.
NIH National Library of Medicine, luciferase luc2CP [Firefly luciferase reporter vector pGL4.12[luc2CP]], GenBank Database Accession No. AAV52873.1, Nov. 8, 2004.
Novikova O, N. Topilina, M. Belfort, J Biol Chem 2014, 289, pp. 14490-14497.
Panda-Jonas et al., Retinal Photoreceptor Count, Retinal Surface Area, and Optic Disc Size in Normal Human Eyes, Opthamology, Mar. 1994, 101(3): 519-523.
Pellissier L P et al., Specific tools for targeting and expression in Müller glial cells. Mol Ther Methods Clin Dev., 2014, vol. 1, 14009.
Perler B et al., Protein splicing and autoproteolysis mechanisms, Mechanisms, 1997, pp. 292-299.
Perler, F. B. InBase, the Intein Database. Nucleic Acids Res., 2002, vol. 30, pp. 383-384.
Petrs-Silva H et al., Novel Properties of Tyrosine-mutant AAV2 Vectors in the Mouse Retina, Mol Ther. Feb. 2011;19(2):293-301.
Pietrokovski S, Conserved sequence features of inteins (protein introns) and their use in identifying new inteins and related proteins, Protein Science, 1994, vol. 3, issue 12, pp. 2340-2350.
Pietrokovski S, Modular organization of inteins and C-terminal autocatalytic domains, Protein Science vol. 7 No. 1, pp. 64-71.
Rangarajan, S., et al., AAV5-Factor VIII Gene Transfer in Severe Hemophilia A. N Engl J Med, 2017. 377(26): p. 2519-2530.
Reich S J, et al. Efficient trans-splicing in the retina expands the utility of adeno-associated virus as a vector for gene therapy, Human Gene Therapy, 2003, 14(1), 37-44.
Remtulla et al., A schematic eye for the mouse, and comparisons with the rat, Vision Research, 1985, 25(1): 21-31.
Salvetti et al. (1998) Factors Influencing Recombinant Adeno-Associated Virus Production, Hum. Gene Ther. 9, pp. 695-706.
Sangermano R et al., Photoreceptor Progenitor mRNA Analysis Reveals Exon Skipping Resulting from the ABCA4 c.5461-10T-→C Mutation in Stargardt Disease, Ophthalmology, 2016, vol. 123, pp. 1375-1385.
Schmelas C, D. Grimm, Split Cas9, Not Hairs—Advancing the Therapeutic Index of CRISPR Technology, Biotechnol J., 2018, vol. 13(9), e1700432.
Shah N H, et al., Extein Residues Play an Intimate Role in the Rate-Limiting Step of Protein Trans-Splicing, J Am Chem Soc 135, 5839-5847 (2013).
Shah N H, T. W. Muir, Inteins: nature's gift to protein chemists, Chem Sci, 2014) vol. 5, pp. 446-461.
Smith A J et al., Gene supplementation therapy for recessive forms of inherited retinal dystrophies, Gene Ther. Feb. 2012;vol. 19(2):pp. 154-161.
Sohocki M. M., et al. Prevalence of mutations causing retinitis pigmentosa and other inherited retinopathies, Hum. Mutat. 2001, vol. 17, pp. 42-51.
Srivastava A, In vivo tissue-tropism of adeno-associated viral vectors, Curr Opin Virol. Dec. 2016;vol. 21 pp. 75-80.
Stevens et al., Design of a Split Intein with Exceptional Protein Splicing Activity, J Am Chem Soc. Feb. 24, 2016; 138(7):2162-5.
Subramanyam P et al., Manipulating L-type calcium channels in cardiomyocytes using split-intein protein transsplicing, Proc Natl Acad Sci, 2013, vol. 110(38) pp. 15461-15466.
Sun H, P. M. Smallwood, J. Nathans, Biochemical defects in ABCR protein variants associated with human retinopathies., Nat Genet, 2000, vol. 26, pp. 242-246.
Surace EM, Auricchio A. Adeno-associated viral vectors for retinal gene transfer. Prog Retin Eye Res. Nov. 2003;22(6):705-19.
Tatusova T A et al., BLAST 2 Sequences, a new tool for comparing protein and nucleotide sequences, FEMS Microbiol. Lett., 1999, vol. 174, No. 2, p. 247-250.
Tatusova T A et al., Erratum to BLAST 2 Sequences, a new tool for comparing protein and nucleotide sequences, FEMS Microbiol. Lett., 1999, vol. 177, No. 1, p. 187-188.

(56) References Cited

OTHER PUBLICATIONS

Trapani et al., Improved dual AAV vectors with reduced expression of truncated proteins are safe and effective in the retina of a mouse model of Stargardt disease, Human Molecular Genetics, Sep. 29, 2015, 24(23): 6811-6825.
Trapani I, A. Auricchio, Seeing the Light after 25 Years of Retinal Gene Therapy, Trends Mol Med., 2018, vol. 24(8) pp. 669-681.
Tsybovsky Y, K. Palczewski, Expression, purification and structural properties of ABC transporter ABCA4 and its individual domains, Protein Expr Purif, 2014, vol. 97, pp. 50-60.
U.S. Appl. No. 60/519,237 entitled "Compositions and methods for treating a posterior segment of an eye", filed Nov. 12, 2003.
U.S. Appl. No. 60/567,423 entitled "Sustained release intraocular implants and related methods", filed Apr. 30, 2004.
U.S. Appl. No. 60/630,062 entitled "Compositions and methods for treating a posterior segment of an eye", filed Dec. 16, 2003.
U.S. Appl. No. 60/721,600 entitled "Anti-angiogenic sustained release intraocular implants and related methods", filed Sep. 28, 2005.
Villiger L et al., Treatment of a metabolic liver disease by in vivo genome base editing in adult mice, Nat Med., 2018, vol. 24, pp. 1519-1525.
Weng J et al., Insights into the function of Rim protein in photoreceptors and etiology of Stargardt's disease from the phenotype in abor knockout mice, Cell, 1999, vol. 98, pp. 13-23.
Wu Z et al. (2008) Optimization of self-complementary AAV Vectors for Liver-directed Expression Results in Sustained Correction of Hemophilia B at Low Vector Dose., Mol. Ther. 16: 280-289.
Yan Z, Y. et al., Trans-splicing vectors expand the utility of adeno-associated virus for gene therapy, Proc Natl Acad Sci USA, 2000, vol. 97, pp. 6716-6721.
Zettler J, V. Schutz, H. D. Mootz, The naturally split Npu DnaE intein exhibits an extraordinarily high rate in the protein trans-splicing reaction, FEBS Letters, 2009, vol. 583, pp. 909-914.
Zhang N et al., Protein misfolding and the pathogenesis of ABCA4-associated retinal degenerations, Hum Mol Genet., 2015, vol. 24, pp. 3220-3237.
Zhong X et al., Generation of three-dimensional retinal tissue with functional photoreceptors from human iPSCs, Nature Communications, 2014, vol. 5, 4047.
Zhu F et al., Inter-chain disulfide bond improved protein trans-splicing increases plasma coagulation activity in C57BL/ mice following portal vein FVIII gene delivery by dual vectors, Science China Life, 2013, vol. 56(3) pp. 262-267.
Zhu F et al,, Protein trans-splicing based dual-vector delivery of the coagulation factor VIII gene, Science China Life Sciences, 2010, vol. 53(6) pp. 683-689.
Zolotukhin S et al., (1999) Recombinant adeno-associated virus purification using novel methods improves infection titer and yield, Gene Ther. 6: 973-985.
U.S. Appl. No. 14/785,229, filed Apr. 18, 2014, U.S. Pub. No. 2016/0076054, Dec. 3, 2019, U.S. Pat. No. 10,494,645, Dec. 3, 2019, Alberto Auricchio, Effective Delivery Of Large Genes By Dual AAV Vectors.
U.S. Appl. No. 15/555,479, filed Mar. 3, 2016, U.S. Pub. No. 2018/0327779, Nov. 15, 2018, Pasqualina Colella, Multiple Vector System And Uses Thereof.
U.S. Appl. No. 17/202,098, filed Mar. 15, 2021, U.S. Pub. No. 2022/0002749, Jan. 6, 2022, Pasqualina Colella, Multiple Vector System and Uses Thereof.
U.S. Appl. No. 17/285,356, filed Oct. 15, 2019, U.S. Pub. No. 2021/0371878, Dec. 2, 2021, Alberto Auricchio, Intein Proteins And Uses Thereof.
U.S. Appl. No. 17/742,924, filed May 12, 2022, U.S. Pub. No. 2022/0389450, Dec. 8, 2022, Alberto Auricchio, Vector System.
Ghosh et al., "Efficient Transgene Reconstrutition with Hybrid Dual AAV Vectors Carrying the Minimized Bridging Sequences," Human Gene Therapy, Jan. 2011, 11: 77-83.
Fujimoto et al., "Minimum Length of Homology Arms Required for Effective Red/ET Recombination", Bioscience, Biotechnology, and Biochemistry, Dec. 23, 2009, 73(12): 2783-2786.
Powell et al., "Viral expression cassette elements to enhance transgene target specificity and expression in gene therapy", Discov Med., Jan. 2015, 19(102): 49-57.
Rubnitz et al., "The minimum amount of homology required for homologous recombination in mammalian cells", Molecular and Cellular Biology, Nov. 1984, 4(11): 2253-2258.
Lopes et al., "Retinal gene therapy with a large MY07A cDNA using adeno-associated virus", Gene Therapy, vol. 20, No. 8, Jan. 24, 2013, pp. 824-833.
Trapan et al., "Effective delivery of large genes to the retina by dual AAV vectors", EMBO Molecular Medicine, vol. 6, No. 2, Dec. 2013, pp. 194-211.
McClements et al., "Gene therapy for retinal disease", Transitional Research, vol. 161, No. 4, Apr. 2013, pp. 241-254.

* cited by examiner

D

E

F

A

B

EFFECTIVE DELIVERY OF LARGE GENES BY DUAL AAV VECTORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a reissue application of U.S. Pat. No. 10,494,645, issued Dec. 3, 2019, which* is a 371 of PCT/EP2014/058000 filed on Apr. 18, 2014 which claims the benefit of priority from U.S. 61/813,342 filed on Apr. 18, 2013.

STATEMENT OF FUNDING

This invention was made with the support of the Italian Telethon Foundation (grant TGM11MT1 and European funds). The Italian Telethon Foundation has rights in this invention.

Studies on the dual AAV trans-splicing and dual AAV hybrid AP strategies were made with U.S. Government support under Contract No. R24RY019861 awarded by the National Eye Institute. The U.S. Government has certain rights in this invention.

*SEQUENCE LISTING*

*The instant application contains a Sequence Listing which has been submitted electronically in ASCII format and is hereby incorporated by reference in its entirety. Said ASCII file, created on May 15, 2024, is named 716968_TIGEM-001REI_ST25.txt and is 74,120 bytes in size.*

TECHNICAL FIELD

The present invention relates to constructs, vectors, relative host cells and pharmaceutical compositions which allow an effective gene therapy, in particular of genes larger than 5 Kb.

BACKGROUND OF THE INVENTION

Inherited retinal degenerations (IRDs), with an overall global prevalence of 1/2,000 (1), are a major cause of blindness worldwide. Among the most frequent and severe IRDs are retinitis pigmentosa (RP), Leber congenital amaurosis (LCA), and Stargardt disease (STGD), which are most often inherited as monogenic conditions. The majority of mutations causing IRDs occur in genes expressed in neuronal photoreceptors (PR), rods and/or cones in the retina (2). No therapy is currently available for these blinding diseases.

Gene therapy holds great promise for the treatment of IRDs. Among the available gene transfer vectors, those based on the small adeno-associated virus (AAV) are most efficient at targeting both PR and retinal pigment epithelium (RPE) (3-4) for long-term treatment upon a single subretinal administration (3-4). Recently the inventors and others, have demonstrated that subretinal administration of AAV is well-tolerated and effective for improving vision in patients affected with type 2 LCA, which is caused by mutations in RPE65, a gene expressed in the RPE (5-9). These results bode well for the treatment of other forms of LCA and IRDs in general. The availability of AAV vector serotypes such as AAV2/8, which efficiently targets PR (10-14) and RPE, further supports this approach. However, a major limitation of AAV is its cargo capacity, which is thought to be limited to around 5 kb, the size of the parental viral genome (15-19). This limits the application of AAV gene therapy approaches for common IRDs that are caused by mutations in genes whose coding sequence (CDS) is larger than 5 kb (herein referred to as large genes). These include:

| DISEASE | GENE | CDS | EXPRESSION |
|---|---|---|---|
| Stargardt Disease | ABCA4 | 6.8 Kb | rod&cone PRs |
| Usher 1B | MYO7A | 6.7 Kb | RPE and PRs |
| Leber Congenital Amaurosis10 | CEP290 | 7.5 Kb | mainly PRs (pan retinal) |
| Usher1D, Nonsyndromic deafness, autosomal recessive (DFNB12) | CDH23 | 10.1 Kb | PRs |
| Retinitis Pigmentosa | EYS | 9.4 Kb | PR ECM |
| Usher 2A | USH2a | 15.6 Kb | rod&cone PRs |
| Usher 2C | GPR98 | 18.0 Kb | mainly PRs |
| Alstrom Syndrome | ALMS1 | 12.5 Kb | rod&cone PRs |

Stargardt disease (STGD; MIM#248200) is the most common form of inherited macular degeneration caused by mutations in the ABCA4 gene (CDS: 6822 bp), which encodes the all-trans retinal transporter located in the PR outer segment (20); Usher syndrome type IB (USH1B; MIM#276900) is the most severe form of RP and deafness caused by mutations in the MYO7A gene (CDS: 6648 bp) (21) encoding the unconventional MYO7A, an actin-based motor expressed in both PR and RPE within the retina (22-24).

Cone-rod dystrophy type 3, fundus flavimaculatus, age-related macular degeneration type 2, Early-onset severe retinal dystrophy, and Retinitis pigmentosa type 19 are also associated with ABCA4 mutations (ABCA4-associated diseases).

Various strategies have been investigated to overcome the limitation of AAV cargo capacity. Several groups, including the inventors' own, have attempted to "force" large genes into one of the many AAV caspids available by developing the so-called oversize vectors (25-27). Although administration of oversize AAV vectors achieves therapeutically-relevant levels of transgene expression in rodent and canine models of human inherited diseases (27-30), including the retina of the Abca4−/− and shaker 1 (sh1) mouse models of STGD and USH1B (27, 30), the mechanism underlying oversize AAV-mediated transduction remains elusive. In contrast to what the inventors and others originally proposed (25-27), oversize AAV vectors do not contain a pure population of intact large size genomes but rather a heterogeneous mixture of mostly truncated genomes≤5 kb in length (15-18). Following infection, reassembly of these truncated genomes in the target cell nucleus has been proposed as a mechanism for oversize AAV vector transduction (15-17, 31). Independent of transduction mechanism and in vivo efficacy, the heterogeneity in oversize AAV genome sizes is a major limitation for their application in human gene therapy.

Alternatively, the inherent ability of AAV genomes to undergo intermolecular concatemerization (32) is exploited to transfer large genes in vivo by splitting a large gene expression cassette into halves (<5 kb in size), each contained in one of two separate (dual) AAV vectors (33-35). In the dual AAV trans-splicing strategy, a splice donor (SD) signal is placed at the 3' end of the 5'-half vector and a splice acceptor (SA) signal is placed at the 5' end of the 3'-half vector. Upon co-infection of the same cell by the dual AAV vectors and inverted terminal repeat (ITR)-mediated head-to-tail concatemerization of the two halves, trans-splicing results in the production of a mature mRNA and full-size protein (33). Trans-splicing has been successfully used to express large genes in muscle and retina (36-37).

In particular, Reich et al. (37) used the trans-splicing strategy with AAV2 and AAV5 capsids and show that both vectors transduce both retinal pigment epithelium and photoreceptors using LacZ gene as a reporter gene. This strategy was not employed using a therapeutic and/or large gene.

Alternatively, the two halves of a large transgene expression cassette contained in dual AAV vectors may contain homologous overlapping sequences (at the 3' end of the 5'-half vector and at the 5' end of the 3'-half vector, dual AAV overlapping), which will mediate reconstitution of a single large genome by homologous recombination (34). This strategy depends on the recombinogenic properties of the transgene overlapping sequences (38). A third dual AAV strategy (hybrid) is based on adding a highly recombinogenic region from an exogenous gene [i.e. alkaline phosphatase, AP (35, 39)] to the trans-splicing vector. The added region is placed downstream of the SD signal in the 5'-half vector and upstream of the SA signal in the 3'-half vector in order to increase recombination between the dual AAVs. The document US2010/003218 is directed to an AP-based hybrid dual vector system. The document shows the transduction efficiency of the AP-based hybrid dual vector expressing mini-dystrophin but no data concerning efficacy.

Lopes et al. (30) studied retinal gene therapy with a large MYO7A cDNA using adeno-associated virus and found that MYO7A therapy with AAV2 or AAV5 single vectors is efficacious to some extent, while the dual AAV2 approach proved to be less effective.

Therefore there is still the need for constructs and vectors that can be exploited to reconstitute large gene expression for an effective gene therapy.

SUMMARY OF THE INVENTION

Retinal gene therapy with adeno-associated viral (AAV) vectors is safe and effective in humans. However, AAV cargo capacity limited to 5 kb prevents it from being applied to therapies of those inherited retinal diseases, such as Stargardt disease (STGD) or Usher syndrome type IB (USH1B) that are due to mutations of genes exceeding 5 kb. Previous methods for large gene transfer tested in the retina and based on "forced" packaging of large genes into AAV capsids (oversize AAV) may not be easily translated to the clinical arena due to the heterogeneity of vector genome size, which represents a safety concern.

Taking advantage of AAV ability to undergo intermolecular concatemerization, the inventors generated dual AAV vectors which reconstitute a large gene by either splicing (trans-splicing), homologous recombination (overlapping), or a combination of the two (hybrid).

To determine which AAV-based strategy most efficiently transduces large genes in the retina, the inventors compared several AAV-based strategies side-by-side in HEK293 cells and in mouse and pig retina in vivo using EGFP, ABCA4 or MYO7A.

The inventors found that dual trans-splicing and hybrid but not overlapping AAV vectors transduce efficiently mouse and pig photoreceptors, the major cell target for treatment of inherited retinal degenerations. The levels of retinal transduction by dual trans-splicing or hybrid AAV resulted in a significant improvement of the phenotype of Abca4−/− and sh1 mouse models of STGD and USH1B. Dual AAV trans-splicing or hybrid vectors are an attractive strategy for gene therapy of retinal diseases that require delivery of large genes.

It is therefore an embodiment of the present invention a dual construct system to express the coding sequence of a gene of interest in an host cell, said coding sequence consisting of a 5' end portion and of a 3' end portion, comprising:

a) a first plasmid comprising in a 5'-3' direction:
- a 5'-inverted terminal repeat (5'-ITR) sequence;
- a promoter sequence;
- the 5' end portion of said coding sequence, said 5'end portion being operably linked to and under control of said promoter;
- a nucleic acid sequence of a splicing donor signal; and
- a 3'-inverted terminal repeat (3'-ITR) sequence; and b) a second plasmid comprising in a 5'-3' direction:
- a 5'-inverted terminal repeat (5'-ITR) sequence;
- a nucleic acid sequence of a splicing acceptor signal;
- the 3'end of said coding sequence;
- a poly-adenylation signal nucleic acid sequence; and
- a 3'-inverted terminal repeat (3'-ITR) sequence.

A preferred embodiment of the present invention is a dual construct system to express the coding sequence of a gene of interest in an host cell, said coding sequence consisting of a 5'end portion and of a 3' end portion, comprising:

a) a first plasmid comprising in a 5'-3' direction:
- a 5'-inverted terminal repeat (5'-ITR) sequence;
- a promoter sequence;
- the 5' end portion of said coding sequence, said 5'end portion being operably linked to and under control of said promoter;
- a nucleic acid sequence of a splicing donor signal; and
- a 3'-inverted terminal repeat (3'-ITR) sequence; and b) a second plasmid comprising in a 5'-3' direction:
- a 5'-inverted terminal repeat (5'-ITR) sequence;
- a nucleic acid sequence of a splicing acceptor signal;
- the 3'end of said coding sequence;
- a poly-adenylation signal nucleic acid sequence; and
- a 3'-inverted terminal repeat (3'-ITR) sequence, wherein upon introduction of said first plasmid and said second plasmid into the host cell, said coding sequence reconstitutes by means of the splicing donor and the splicing acceptor signals. The dual construct system of the present invention is advantageously exploited to reconstitute large gene expression. When the coding sequence reconstitutes, gene expression occurs.

Preferably, said first plasmid and said second plasmid further comprise a nucleic acid sequence of a recombinogenic region in 5' position of the 3'ITR and in 3' position of the 5'-ITR, respectively.

More preferably, the recombinogenic region is a F1 phage recombinogenic region.

Still preferably the nucleic acid sequence of a recombinogenic region consists essentially of the sequence:

(SEQ ID NO: 3)

GGGATTTTGCCGATTTCGGCCTATTGGTTAAAAAATGAGCTGATTTAACA

AAAATTTAACGCGAATTTTAACAAAAT.

The recombinogenic region may also be a fragment of SEQ ID NO. 3, said fragment maintaining the recombinogenic properties of the full length sequence. Preferably the fragment has 70%, 75%, 80%, 85%, 90%, 95% or 99% identity with SEQ ID NO. 3.

Still preferably, the nucleotide sequence of the ITRs derives from the same or different AAV serotype.

Preferably, the 3'-ITR of the first plasmid and the 5'-ITR of the second plasmid are from the same AAV serotype.

Yet preferably, the 5'-ITR and 3'-ITR of the first plasmid and the 5'-ITR and 3'-ITR of the second plasmid are respectively from different AAV serotypes.

Preferably, the 5'-ITR of the first plasmid and the 3'-ITR of the second plasmid are from different AAV serotypes.

Yet preferably the coding sequence is split into the 5' end portion and the 3' end portion at a natural exon-exon junction.

In a preferred embodiment the nucleic acid sequence of the splicing donor signal consists essentially of the sequence:

(SEQ ID NO: 1)

GTAAGTATCAAGGTTACAAGACAGGTTTAAGGAGACCAATAGAAACTGGG

CTTGTCGAGACAGAGAAGACTCTTGCGTTTCT.

In a preferred embodiment the nucleic acid sequence of the splicing acceptor signal consists essentially of the sequence:

(SEQ ID NO: 2)

GATAGGCACCTATTGGTCTTACTGACATCCACTTTGCCTTTCTCTCCACA

G.

The spicing acceptor signal and the splicing donor signal may also be chosen by the skilled person in the art among sequences known in the art.

Spliceosomal introns often reside within the sequence of eukaryotic protein-coding genes. Within the intron, a donor site (5' end of the intron), a branch site (near the 3' end of the intron) and an acceptor site (3' end of the intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. Upstream (5'-ward) from the AG there is a region high in pyrimidines (C and U), or polypyrimidine tract. Upstream from the polypyrimidine tract is the branchpoint, which includes an adenine nucleotide.

In a preferred embodiment the first plasmid further comprises at least one enhancer sequence, operably linked to the coding sequence. Any known suitable enhancer sequence may be selected by the skilled person in the art.

Preferably the coding sequence is a nucleotide sequence encoding a protein able to correct a genetic disease, in particular an inherited retinal degeneration.

Still preferably the coding sequence is selected from the group consisting of: ABCA4, MYO7A, CEP290, CDH23, EYS, USH2a, GPR98 or ALMS1.

It is a further embodiment of the invention a dual viral vector system comprising:

a) a first viral vector containing the first plasmid comprising in a 5'-3' direction: a 5'-inverted terminal repeat (5'-ITR) sequence, a promoter sequence, the 5' end portion of said coding sequence, said 5'end portion being operably linked to and under control of said promoter, a nucleic acid sequence of a splicing donor signal, and a 3'-inverted terminal repeat (3'-ITR) sequence; and b) a second viral vector containing the second plasmid comprising in a 5'-3' direction: a 5'-inverted terminal repeat (5'-ITR) sequence, a nucleic acid sequence of a splicing acceptor signal, the 3'end of said coding sequence, a poly-adenylation signal nucleic acid sequence; and a 3'-inverted terminal repeat (3'-ITR) sequence.

Preferably the vectors are adeno-associated virus (AAV) vectors.

Still preferably the adeno-associated virus (AAV) vectors are selected from the same or different AAV serotypes.

Still preferably the adeno-associated virus is selected from the serotype 2, the serotype 8, the serotype 5, the serotype 7 or the serotype 9.

It is a further embodiment of the invention a host cell transformed with the dual viral vector system according to the invention.

Preferably the host cell is a mammalian cell, a human cell, a retinal cell, a non-embryonic stem cell.

It is a further embodiment of the invention the dual construct system of the invention, the dual viral vector system of the invention or the host cell of the invention for medical use, preferably for use in a gene therapy, still preferably for the treatment and/or prevention of a pathology or disease characterized by a retinal degeneration. Preferably, the retinal degeneration is inherited.

Still preferably the pathology or disease is selected from the group consisting of: retinitis pigmentosa, Leber congenital amaurosis (LCA), Stargardt disease, Usher disease, Alstrom syndrome, a disease caused by a mutation in the ABCA4 gene (also named a ABCA4-associated disease). Cone-rod dystrophy type 3, fundus flavimaculatus, age-related macular degeneration type 2, Early-onset severe retinal dystrophy, and Retinitis pigmentosa type 19 are examples of disease caused by a mutation in the ABCA4 gene (ABCA4-associated diseases).

It is a further embodiment of the invention a pharmaceutical composition comprising the dual construct system according to the invention, the dual viral vector system according to the invention or the host cell according to the invention and pharmaceutically acceptable vehicle.

It is a further embodiment of the invention a method for treating and/or preventing a pathology or disease characterized by a retinal degeneration comprising administering to a subject in need thereof an effective amount of the dual construct system as described herein, the dual viral vector system as described herein or the host cell as described herein.

It is a further embodiment of the invention a nucleic acid consisting of SEQ ID No. 3 for use as a recombinogenic region.

It is a further embodiment of the invention a method to induce genetic recombination comprising using the sequence consisting of SEQ ID No. 3.

In the present invention preferably the promoter is selected from the group consisting of: cytomegalovirus promoter, Rhodopsin promoter, Rhodopsin kinase promoter, Interphotoreceptor retinoid binding protein promoter, vitelliform macular dystrophy 2 promoter. However any suitable promoter known in the art may be used.

In the present invention, the coding sequence is split into a first and a second fragment (5' end portion and 3' end portion) at a natural exon-exon junction. Preferably each fragment of the coding sequence should not exceed a size of 10 kb. Preferably each 5' end portion and 3' end portion may have a size of 4.5 Kb, 5 Kb, 5.5 Kb, 6 Kb, 6.5 Kb, 7 kb, 7.5 Kb, 8 Kb, 8.5 Kb, 9 Kb, 9.5 Kb or a smaller size.

During the past decade, gene therapy has been applied to the treatment of disease in hundreds of clinical trials. Various tools have been developed to deliver genes into human cells; among them, genetically engineered viruses, including adenoviruses, are currently amongst the most popular tool for gene delivery. Most of the systems contain vectors that are capable of accommodating genes of interest and helper cells that can provide the viral structural proteins and enzymes to allow for the generation of vector-containing infectious viral particles. Adeno-associated virus is a family of viruses that differs in nucleotide and amino acid sequence, genome structure, pathogenicity, and host range. This diversity provides opportunities to use viruses with different biological characteristics to develop different therapeutic applications. As with any delivery tool, the efficiency, the ability to target certain tissue or cell type, the expression of the gene of interest, and the safety of adenoviral-based systems are important for successful application of gene therapy. Significant efforts have been dedicated to these areas of research in recent years. Various modifications have been made to Adeno-associated virus-based vectors and helper cells to alter gene expression, target delivery, improve viral titers, and increase safety. The present invention represents an improvement in this design process in that it acts to efficiently deliver genes of interest into such viral vectors. Viruses are logical tools for gene delivery. They replicate inside cells and therefore have evolved mechanisms to enter the cells and use the cellular machinery to express their genes. The concept of virus-based gene delivery is to engineer the virus so that it can express the gene of interest. Depending on the specific application and the type of virus, most viral vectors contain mutations that hamper their ability to replicate freely as wild-type viruses in the host. Viruses from several different families have been modified to generate viral vectors for gene delivery. These viruses include retroviruses, lentivirus, adenoviruses, adeno-associated viruses, herpes simplex viruses, picornaviruses, and alphaviruses. The present invention preferably employs adeno-associated viruses.

An ideal adeno-associated virus based vector for gene delivery must be efficient, cell-specific, regulated, and safe. The efficiency of delivery is important because it can determine the efficacy of the therapy. Current efforts are aimed at achieving cell-type-specific infection and gene expression with adeno-associated viral vectors. In addition, adeno-associated viral vectors are being developed to regulate the expression of the gene of interest, since the therapy may require long-lasting or regulated expression. Safety is a major issue for viral gene delivery because most viruses are either pathogens or have a pathogenic potential. It is important that during gene delivery, the patient does not also inadvertently receive a pathogenic virus that has full replication potential.

Adeno-associated virus (AAV) is a small virus which infects humans and some other primate species. AAV is not currently known to cause disease and consequently the virus causes a very mild immune response. Gene therapy vectors using AAV can infect both dividing and quiescent cells and persist in an extrachromosomal state without integrating into the genome of the host cell. These features make AAV a very attractive candidate for creating viral vectors for gene therapy, and for the creation of isogenic human disease models.

Wild-type AAV has attracted considerable interest from gene therapy researchers due to a number of features. Chief amongst these is the virus's apparent lack of pathogenicity. It can also infect non-dividing cells and has the ability to stably integrate into the host cell genome at a specific site (designated AAVS1) in the human chromosome 19. The feature makes it somewhat more predictable than retroviruses, which present the threat of a random insertion and of mutagenesis, which is sometimes followed by development of a cancer. The AAV genome integrates most frequently into the site mentioned, while random incorporations into the genome take place with a negligible frequency. Development of AAVs as gene therapy vectors, however, has eliminated this integrative capacity by removal of the rep and cap from the DNA of the vector. The desired gene together with a promoter to drive transcription of the gene is inserted between the inverted terminal repeats (ITR) that aid in concatamer formation in the nucleus after the single-stranded vector DNA is converted by host cell DNA polymerase complexes into double-stranded DNA. AAV-based gene therapy vectors form episomal concatamers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency. AAVs also present very low immunogenicity, seemingly restricted to generation of neutralizing antibodies, while they induce no clearly defined cytotoxic response. This feature, along with the ability to infect quiescent cells present their dominance over adenoviruses as vectors for the human gene therapy.

AAV Genome, Transcriptome and Proteome

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry.

ITR Sequences

The Inverted Terminal Repeat (ITR) sequences comprise 145 bases each. They were named so because of their symmetry, which was shown to be required for efficient multiplication of the AAV genome. Another property of these sequences is their ability to form a hairpin, which contributes to so-called self-priming that allows primase-independent synthesis of the second DNA strand. The ITRs were also shown to be required for both integration of the AAV DNA into the host cell genome (19th chromosome in humans) and rescue from it, as well as for efficient encapsidation of the AAV DNA combined with generation of a fully assembled, deoxyribonuclease-resistant AAV particles.

With regard to gene therapy, ITRs seem to be the only sequences required in cis next to the therapeutic gene: structural (cap) and packaging (rep) genes can be delivered in trans. With this assumption many methods were established for efficient production of recombinant AAV (rAAV) vectors containing a reporter or therapeutic gene. However, it was also published that the ITRs are not the only elements required in cis for the effective replication and encapsidation. A few research groups have identified a sequence designated cis-acting Rep-dependent element (CARE)

inside the coding sequence of the rep gene. CARE was shown to augment the replication and encapsidation when present in cis.

As of 2006 there have been 11 AAV serotypes described, the 11th in 2004. All of the known serotypes can infect cells from multiple diverse tissue types. Tissue specificity is determined by the capsid serotype and pseudotyping of AAV vectors to alter their tropism range will likely be important to their use in therapy. In the present invention ITRs of AVV serotype 2 and serotype 5 are preferred.

Serotype 2

Serotype 2 (AAV2) has been the most extensively examined so far. AAV2 presents natural tropism towards skeletal muscles, neurons, vascular smooth muscle cells and hepatocytes.

Three cell receptors have been described for AAV2: heparan sulfate proteoglycan (HSPG), $\alpha_v\beta_5$ integrin and fibroblast growth factor receptor 1 (FGFR-1). The first functions as a primary receptor, while the latter two have a co-receptor activity and enable AAV to enter the cell by receptor-mediated endocytosis. These study results have been disputed by Qiu, Handa, et al. HSPG functions as the primary receptor, though its abundance in the extracellular matrix can scavenge AAV particles and impair the infection efficiency.

Serotype 2 and Cancer

Studies have shown that serotype 2 of the virus (AAV-2) apparently kills cancer cells without harming healthy ones. "Our results suggest that adeno-associated virus type 2, which infects the majority of the population but has no known ill effects, kills multiple types of cancer cells yet has no effect on healthy cells," said Craig Meyers, a professor of immunology and microbiology at the Penn State College of Medicine in Pennsylvania. This could lead to a new anti-cancer agent.

Other Serotypes

Although AAV2 is the most popular serotype in various AAV-based research, it has been shown that other serotypes can be more effective as gene delivery vectors. For instance AAV6 appears much better in infecting airway epithelial cells, AAV7 presents very high transduction rate of murine skeletal muscle cells (similarly to AAV1 and AAV5), AAV8 is superb in transducing hepatocytes and AAV1 and 5 were shown to be very efficient in gene delivery to vascular endothelial cells. In the brain, most AAV serotypes show neuronal tropism, while AAV5 also transduces astrocytes. AAV6, a hybrid of AAV1 and AAV2, also shows lower immunogenicity than AAV2.

Serotypes can differ with the respect to the receptors they are bound to. For example AAV4 and AAV5 transduction can be inhibited by soluble sialic acids (of different form for each of these serotypes), and AAV5 was shown to enter cells via the platelet-derived growth factor receptor.

In the present invention the delivery vehicles of the present invention may be administered to a patient. A skilled worker would be able to determined appropriate dosage rates. The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors etc as described above. Non-viral delivery mechanisms include lipid mediated transfection, liposomes, immunoliposomes, lipofectin, cationic facial amphiphiles (CFAs) and combinations thereof.

The delivery of one or more therapeutic genes by a vector system according to the present invention may be used alone or in combination with other treatments or components of the treatment.

The present invention also provides a pharmaceutical composition for treating an individual by gene therapy, wherein the composition comprises a therapeutically effective amount of the vector/construct or host cell of the present invention comprising one or more deliverable therapeutic and/or diagnostic transgenes(s) or a viral particle produced by or obtained from same. The pharmaceutical composition may be for human or animal usage. Typically, a physician will determine the actual dosage which will be most suitable for an individual subject and it will vary with the age, weight and response of the particular individual. The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system). Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The man skilled in the art is well aware of the standard methods for incorporation of a polynucleotide or vector into a host cell, for example transfection, lipofection, electroporation, microinjection, viral infection, thermal shock, transformation after chemical permeabilisation of the membrane or cell fusion.

As used herein, the term "host cell or host cell genetically engineered" relates to host cells which have been transduced, transformed or transfected with the construct or with the vector described previously.

As representative examples of appropriate host cells, one can cites bacterial cells, such as E. coli, Streptomyces, Salmonella typhimurium, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell. The invention further provides a host cell comprising any of the recombinant expression vectors described herein. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α, E. coli cells, Chinese hamster ovarian cells, monkey VERO cells, COS cells, HEK293 cells, and the like.

The present invention will now be illustrated by means of non-limiting examples in reference to the following drawings.

FIG. 1. Schematic representation of AAV-based strategies for large gene transduction.

CDS: coding sequence; pA: poly-adenilation signal; SD: splicing donor signal; SA: splicing acceptor signal; AP: alkaline phosphatase recombinogenic region (39); AK: F1 phage recombinogenic region. Dotted lines show the splicing occurring between SD and SA, pointed lines show overlapping regions available for homologous recombination. The inventors found that dual trans-splicing and hybrid AK may be used to successfully reconstitute large gene expression. In particular dual trans-splicing and hybrid AK vectors, but not overlapping and hybrid AP vectors, transduce efficiently mouse and pig photoreceptors. Normal size and oversize AAV vector plasmids contained full length expression cassettes including the promoter, the full-length transgene CDS and the poly-adenilation signal (pA) (Table 1). The two separate AAV vector plasmids (5' and 3') required to generate dual AAV vectors contained either the promoter followed by the N-terminal portion of the transgene CDS (5' plasmid) or the C-terminal portion of the transgene CDS followed by the pA signal (3' plasmid, Table 1). The structure of all plasmids is indicated in the material and method section.

Figure 2:
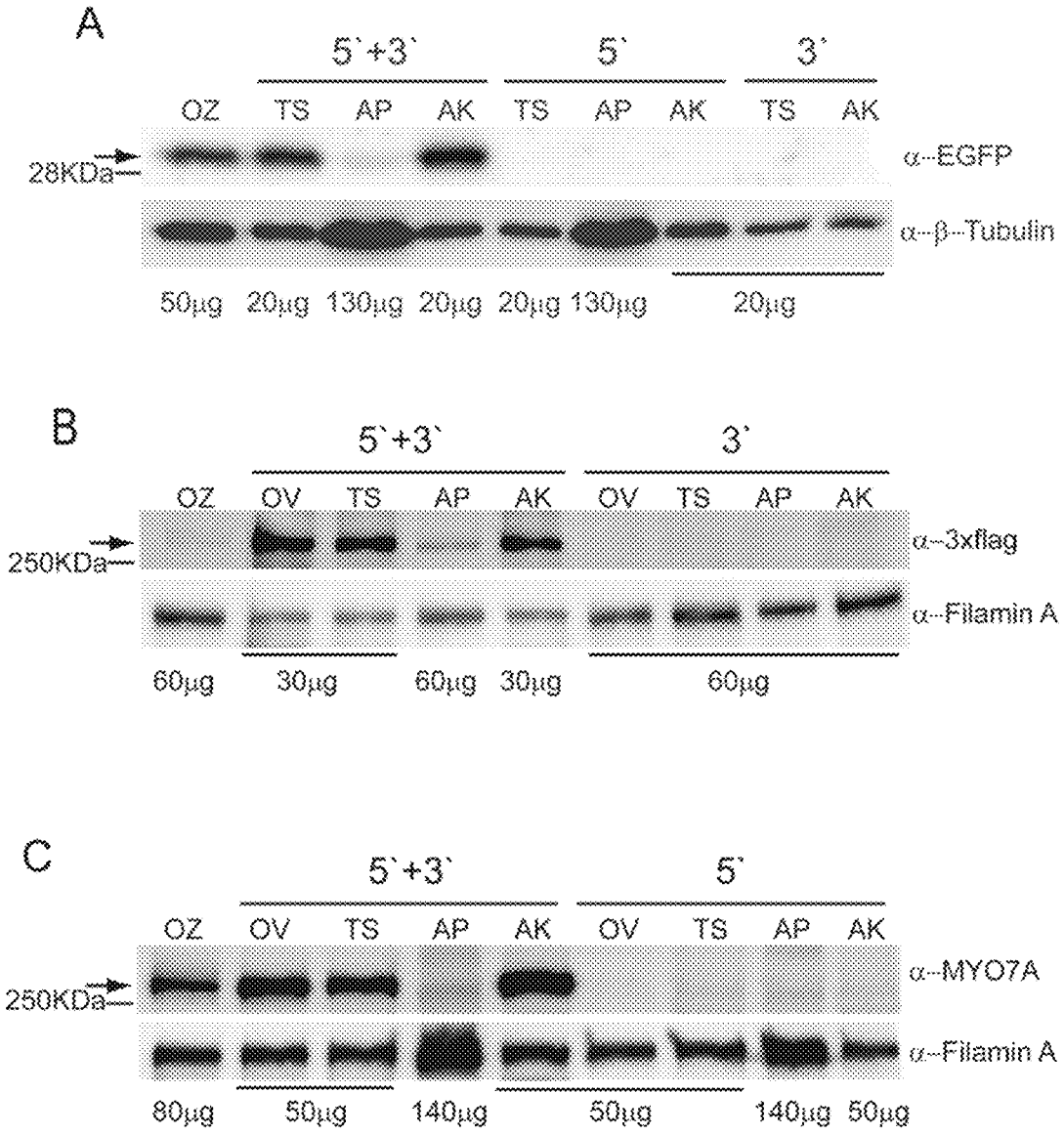
Figure 2:
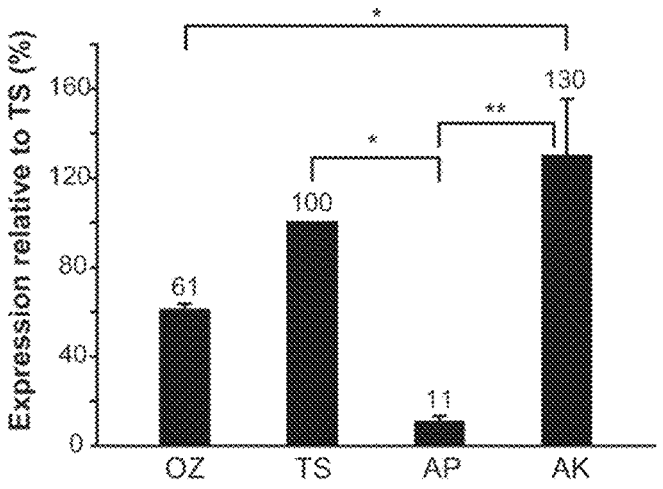
Figure 2:
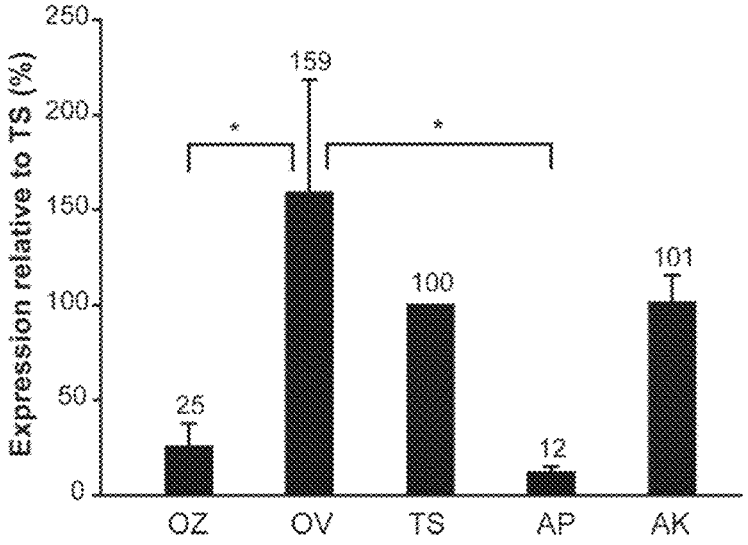
Figure 2:
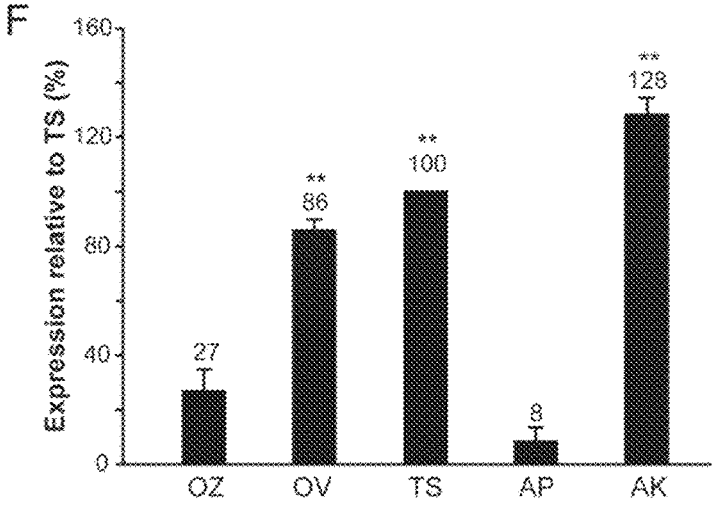

FIG. 2. Dual AAV overlapping, trans-splicing and hybrid AK vectors efficiently transduce large genes in vitro.

Figure 3:
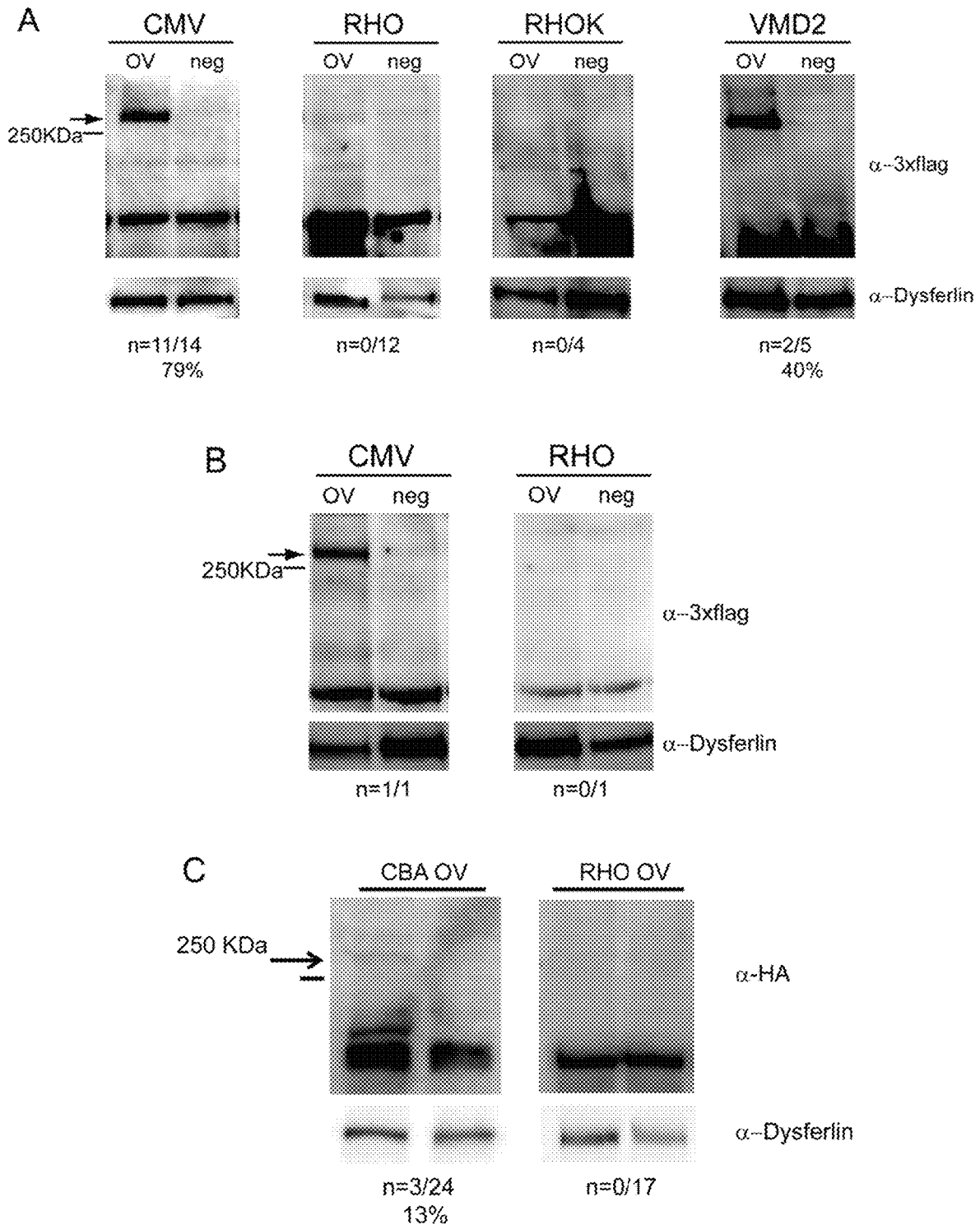

Western blot of HEK293 cells infected with AAV2/2 vectors encoding for EGFP (A and D), ABCA4 (B and E) and MYO7A (C and F). (A to C) The arrows indicate full-length proteins, the micrograms of proteins loaded are depicted under each lane, the molecular weight ladder is depicted on the left. (D to F) Quantification of EGFP (D), ABCA4 (E) and MYO7A (F) protein bands. The intensity of the EGFP, ABCA4 and MYO7A bands was divided by the intensity of the Tubulin (D) or Filamin A (E-F) bands. The histograms show the expression of proteins as a percentage relative to dual AAV trans-splicing (TS) vectors, the mean value is depicted above the corresponding bar. Error bars: mean±s.e.m. (standard error of the mean). (A-C) The Western blot images are representative of and the quantifications are from n=4 (A-B) or n=3 (C) independent experiments. OZ: AAV oversize; OV: dual AAV overlapping; TS: dual AAV trans-splicing; AP: dual AAV hybrid AP; AK: dual AAV hybrid AK; 5'+3': cells co-infected with 5'- and 3'-half vectors; 5': control cells infected with the 5'-half vector only; 3': control cells infected with the 3'-half only; α-EGFP: anti-EGFP antibody; α-3×flag: anti-3×flag antibody; α-MYO7A: anti-MYO7A antibody; α-β-Tubulin: anti-β-tubulin antibody; α-Filamin A: anti-filamin A antibody. * ANOVA p value<0.05;  ANOVA p value<0.001. (F) The asterisks depicted in the lower panel represent significant differences with both OZ and AP. In FIG. 3**. Dual AAV overlapping vectors transduce RPE but not photoreceptors in the mouse and pig retina.

Western blot analysis of C57BL/6 (A) and Large White pig (B) retinal lysates one month following injection of AAV2/8 dual AAV overlapping vectors encoding for ABCA4-3×flag (OV) or AAV2/8 vectors encoding for normal size EGFP (EGFP), under the control of the ubiquitous cytomegalovirus (CMV) promoter, the PR-specific Rhodopsin (RHO) and Rhodopsin kinase (RHOK) promoters, or the RPE-specific vitelliform macular dystrophy 2 (VMD2) promoter. (A-B) The arrows indicate full-length proteins, the molecular weight ladder is depicted on the left, 150 micrograms of proteins were loaded in each lane. The number (n) and percentage of ABCA4-positive retinas out of total retinas analyzed is depicted; α-3×flag: anti-3×flag antibody; α-Dysferlin: anti-Dysferlin antibody (C) Western blot analysis on C57/BL6 eyecups (left panel) and retinas (right panel) at 3 months following the injection of AAV2/8 overlapping vectors encoding for MYO7A-HA (OV) under the control of the ubiquitous chicken-beta-actin (CBA) promoter or the photoreceptor-specific rhodopsin (RHO) promoter. The arrow points at full-length proteins, the molecular weight ladder is depicted on the left, 100 micrograms of protein were loaded in each lane. The number (n) and percentage of MYO7A positive retinas out of total retinas analyzed is depicted. α-HA: anti-hemagglutinin (HA) antibody.

Figure 4:
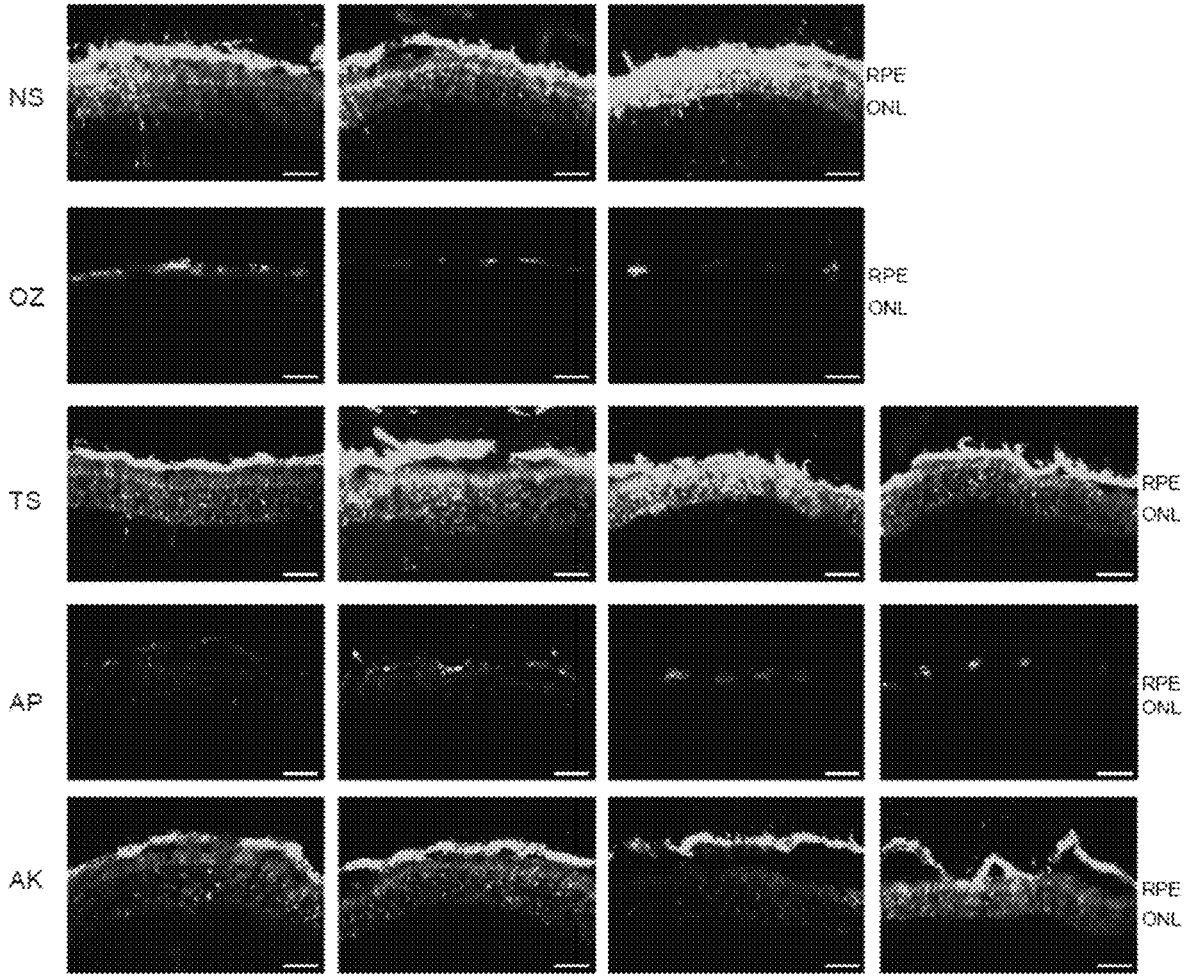

FIG. 4. Dual AAV trans-splicing and hybrid AK vectors efficiently transduce both RPE and photoreceptors.

Fluorescence analysis of retinal cryosections from C57BL/6 mice one month following subretinal injection of AAV2/8 vectors encoding for EGFP under the control of the ubiquitous cytomegalovirus (CMV) promoter. The scale bar (20 μm) is depicted in the figure. NS: AAV normal size; OZ: AAV oversize; TS: dual AAV trans-splicing; AP: dual AAV hybrid AP; AK: dual AAV hybrid AK; RPE: retinal pigmented epithelium; ONL: outer nuclear layer.

Figure 5:
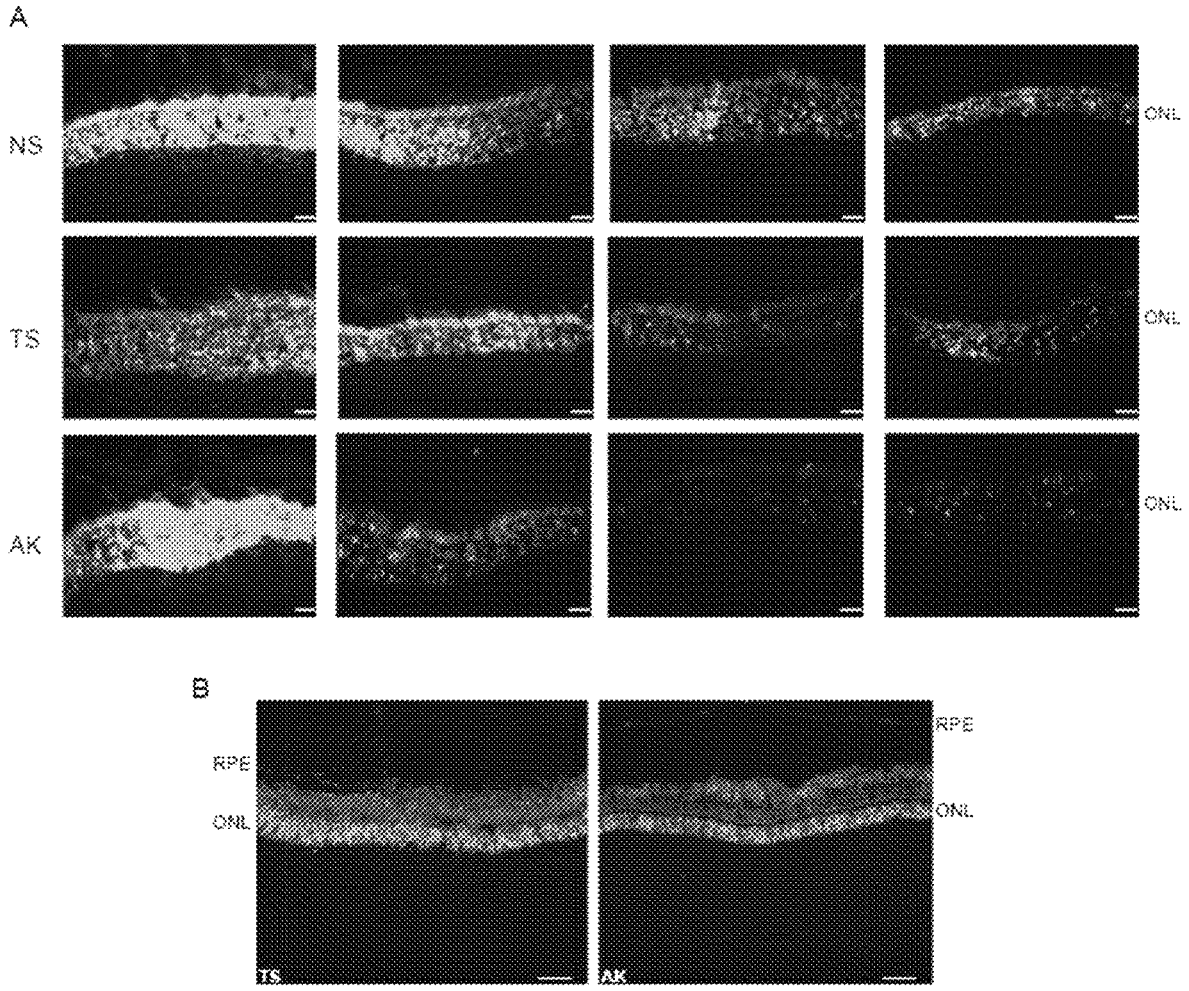

FIG. 5. Dual AAV trans-splicing and hybrid AK efficiently transduce mouse and pig photoreceptors.

(A) Fluorescence analysis of retinal cryosections from C57BL/6 mice one month following subretinal injection of AAV2/8 vectors encoding for EGFP under the control of the PR-specific Rhodopsin promoter (RHO). The scale bar (20 μm) is depicted in the figure. (B) Fluorescence analysis of retinal cryosections from Large White pigs one month following subretinal injection of AAV2/8 vectors encoding for EGFP under the control of the PR-specific RHO promoter. The scale bar (50 μm) is depicted in the figure. NS: AAV normal size; TS: dual AAV trans-splicing; AK: dual AAV hybrid AK; RPE: retinal pigmented epithelium; ONL: outer nuclear layer.

Figure 6:
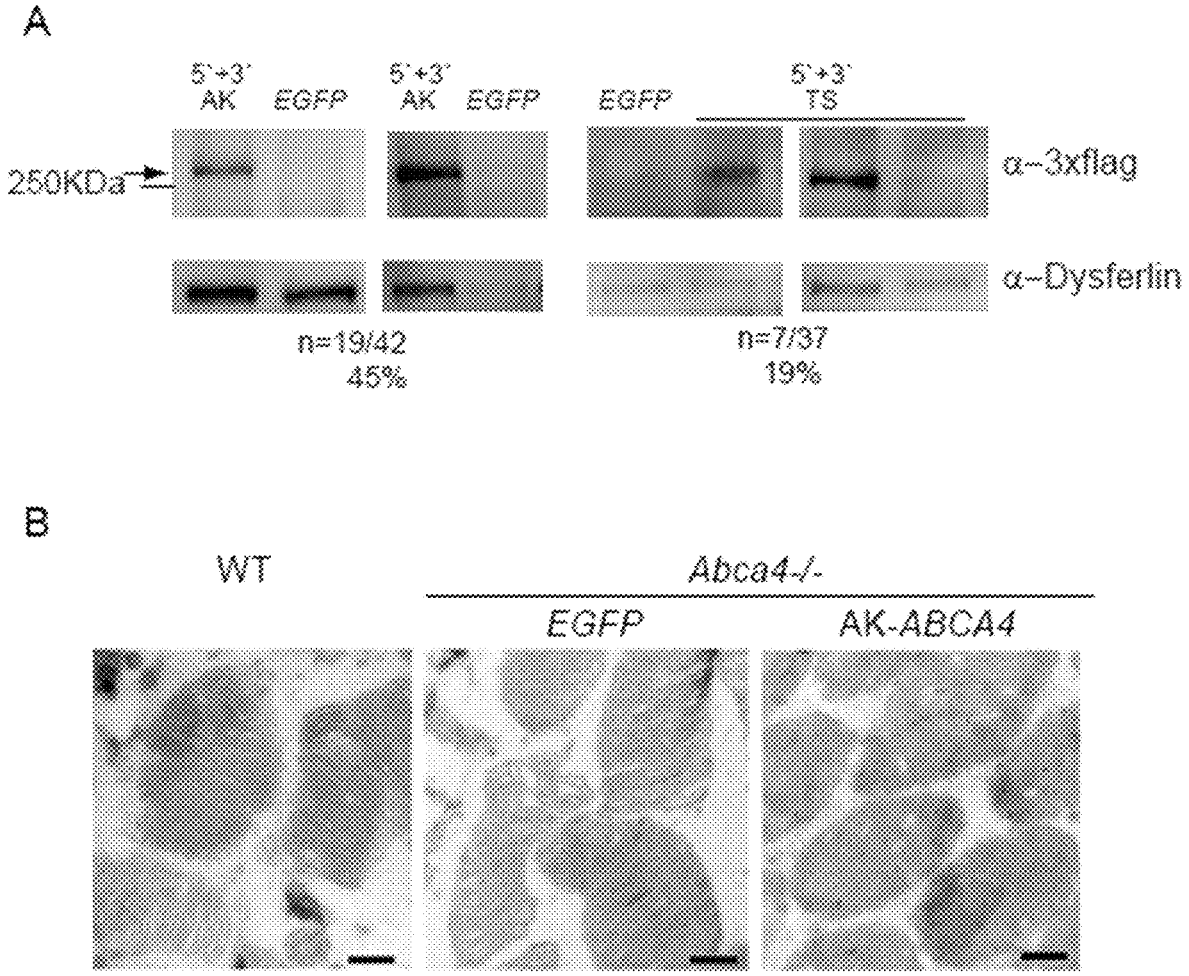

FIG. 6. Subretinal administration of dual AAV trans-splicing and hybrid AK vectors results in robust yet variable levels of ABCA4 expression in mouse photoreceptors.

(A) Western blot analysis of C57BL/6 retinal lysates one month following the injection of dual AAV trans-splicing (TS) and dual AAV hybrid AK (AK) vectors encoding for ABCA4 under the control of the PR-specific Rhodopsin promoter (RHO). The arrow points at full-length proteins, the molecular weight ladder is depicted on the left, 150 micrograms of protein were loaded in each lane. The number (n) and percentage of ABCA4-positive retinas out of total retinas analysed is depicted. 5'+3': retinas co-injected with 5'- and 3'-half vectors; α-3×flag: anti-3×flag antibody; α-Dysferlin: anti-Dysferlin antibody. (B) Immuno-electron microscopy analysis with anti-HA antibody of retinal sections from wild-type Balb/C (WT; n=3 eyes) and Abca4−/− mice injected with dual AAV hybrid AK vectors (AK-ABCA4; n=5 eyes) or with AAV normal size EGFP (EGFP, n=3 eyes) as control. The black dots represent the immunogold labelling of the ABCA4-HA protein. The scale bar (200 nm) is depicted in the figure.

Figure 7:
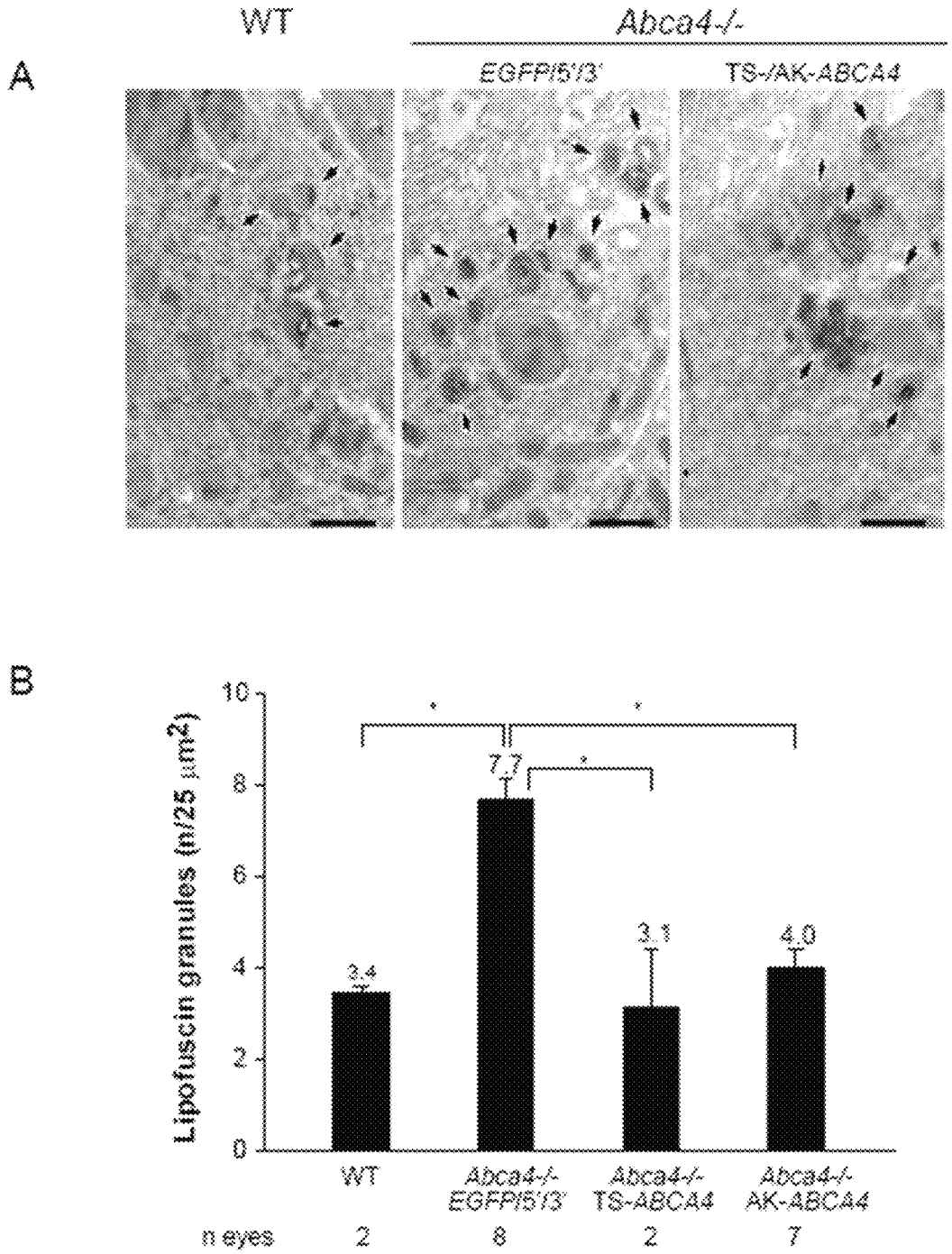

FIG. 7. Subretinal injection of dual AAV hybrid AK vectors reduces accumulation of lipofuscin granules in Abca4−/− mice.

(A) Transmission electron microscopy analysis of retinal sections from wild-type Balb/c (WT) and Abca4−/− mice injected with either dual AAV hybrid AK vectors (Abca4−/− AK-ABCA4) or with AAV normal size EGFP (Abca4−/−

EGFP) as control. The black arrows indicate lipofuscin granules. The scale bar (1.6 μm) is depicted in the figure. (B) Quantification of the mean number of lipofuscin granules counted in at least 30 fields (25 $\mu m^2$) for each sample. WT: Balb/c mice; Abca4−/− EGFP/5'/3': Abca4−/− mice injected with either AAV normal size EGFP or the 5' or 3' half vector of the dual AAV hybrid AK, as control; Abca4−/− AK-ABCA4: mice injected with dual AAV hybrid AK vectors; Abca4−/− TS-ABCA4: mice injected with dual AAV trans-splicing vectors. The number (n) of eyes analysed is depicted. The mean value is depicted above the corresponding bar. Error bars: mean±s.e.m. (standard error of the mean). * p ANOVA<0.05

Figure 8:
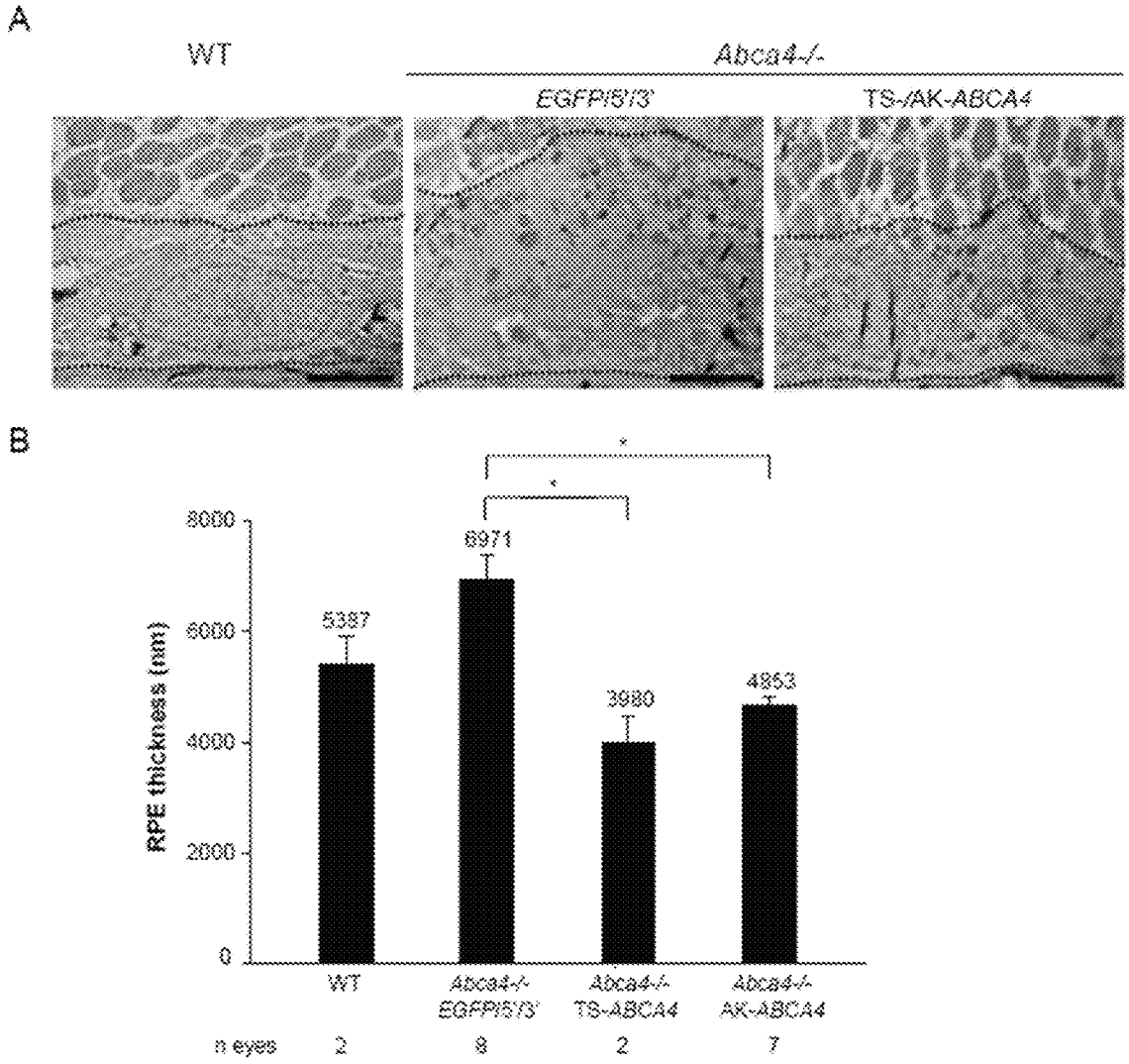

FIG. 8. Subretinal injections of dual AAV hybrid AK vectors reduces the thickness of Abca4−/− RPE.

(A) Representative pictures of transmission electron microscopy analysis of retinal sections from wild-type Balb/c (WT) and Abca4−/− mice injected with either dual AAV trans-splicing (TS-ABCA4) and hybrid AK vectors (AK-ABCA4) or with AAV normal size EGFP (EGFP) and 5' or 3' half of the dual hybrid AK vectors (5'/3') as control. The dotted lines indicate the edges of RPE cells. The scale bar (3.8 μm) is depicted in the figure. (B) Quantification of the mean RPE thickness counted in at least 30 fields for each sample. The number (n) of eyes analysed is depicted. The mean value is depicted above the corresponding bar. Error bars: mean±s.e.m (standard error of the mean). s.d.m: WT: ±716; TS-ABCA4: ±698.

Figure 9:
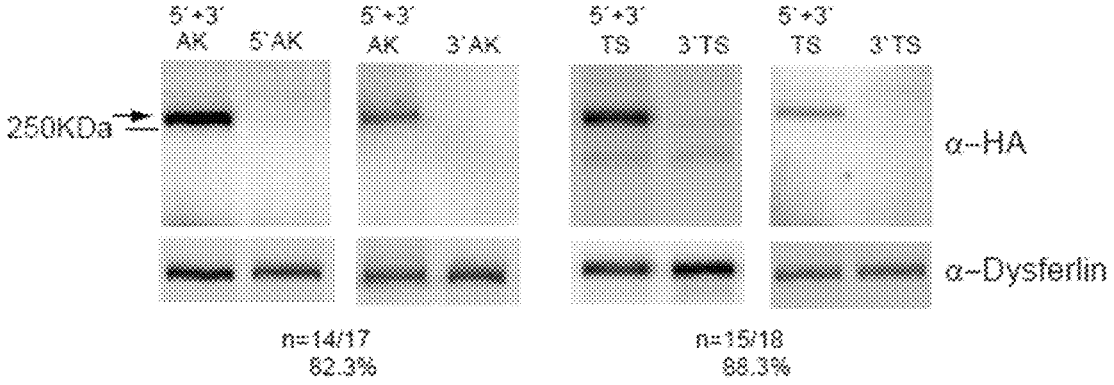

FIG. 9. Subretinal administration of dual AAV trans-splicing and hybrid AK vectors results in robust MYO7A expression in mice.

Western blot analysis of C57BL/6 eyecups one month following the injection of dual AAV trans-splicing (TS) and hybrid AK (AK) vectors encoding for MYO7A-HA under the control of the ubiquitous chicken beta-actin (CBA) promoter. The arrow indicates full-length proteins, the molecular weight ladder is depicted on the left, 100 micrograms of proteins were loaded in each lane. The number (n) and percentage of MYO7A-positive eyecups out of total retinas analyzed is depicted. 5'+3': eyes co-injected with 5'- and 3'-half vectors; 5': eyes injected with 5'-half vectors; 3': eyes injected with 3'-half vectors; α-HA: anti-hemagglutinin (HA) antibody; α-Dysferlin: anti-Dysferlin antibody.

Figure 10:
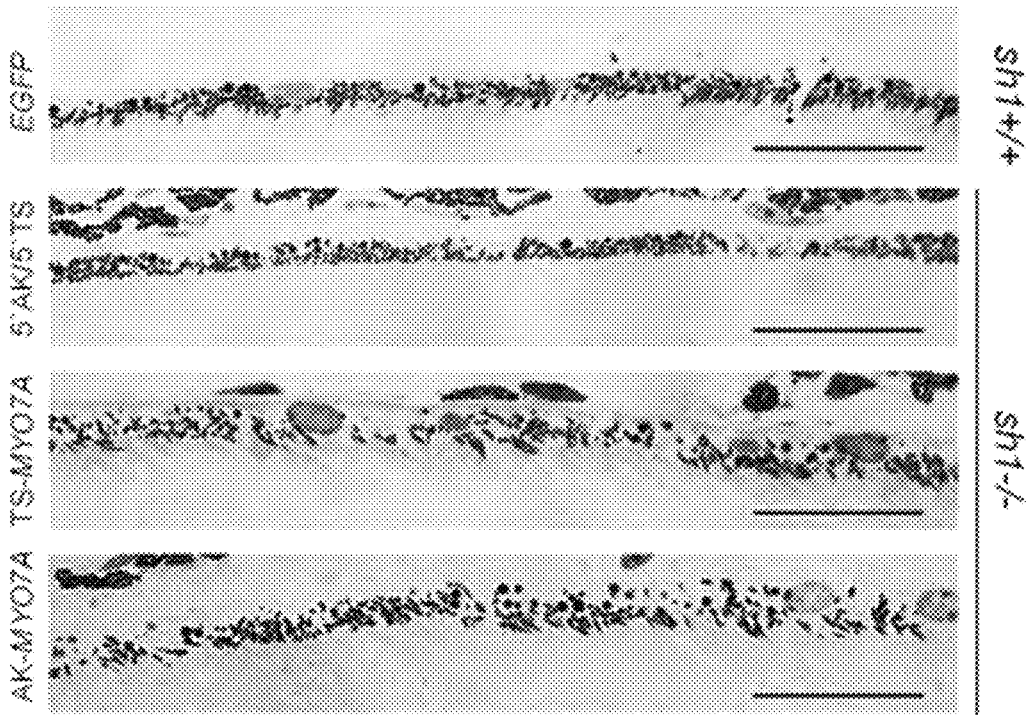
Figure 10:
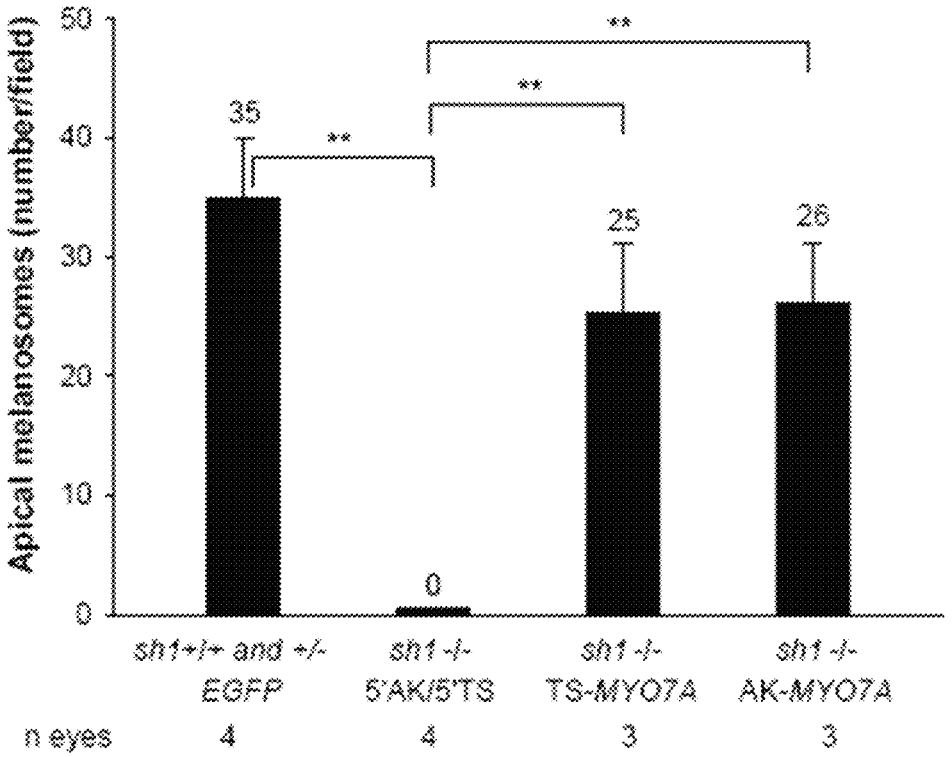

FIG. 10. Subretinal administration of dual AAV trans-splicing and hybrid AK vectors rescues melanosome localization in sh1−/− RPE.

(A) Representative semi-thin retinal sections stained with Epoxy tissue stain of sh1+/+ and sh1+/− eyes injected with AAV normal size EGFP (EGFP, n=4 eyes), and of sh1−/− eyes injected with dual AAV trans-splicing (TS-MYO7A, n=3 eyes), hybrid AK (AK-MYO7A; n=3 eyes) or 5'-half vectors (5'TS/5'AK, n=4 eyes), as control. The scale bar (10 μm) is depicted in the figure. (B) Quantification of melanosome localization in the RPE villi of sh1 mice two months following subretinal delivery of dual AAV vectors. The quantification is depicted as the mean number of apical melanosomes/field, the mean value is depicted above the corresponding bar. Error bars: mean±s.e.m. (standard error of the mean). * p ANOVA<0.05, ** p ANOVA<0.001.

Figure 11:
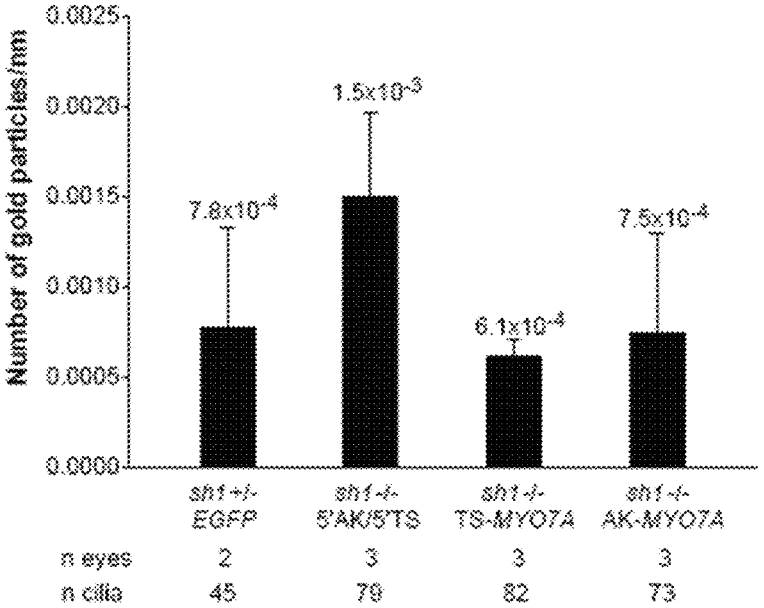

FIG. 11. Subretinal administration of dual AAV trans-splicing and hybrid AK vectors reduces rhodopsin accumulation at sh1−/− PR connecting cilia.

Quantification of the number of rhodopsin gold particles at the PR connecting cilium of sh1 mice two months following subretinal delivery of dual AAV vectors. The quantification is depicted as the mean number of gold particles per length of connecting cilia (nm), the mean value is depicted above the corresponding bar. Error bars: mean±s.e.m. (standard error of the mean).

Figure 12:
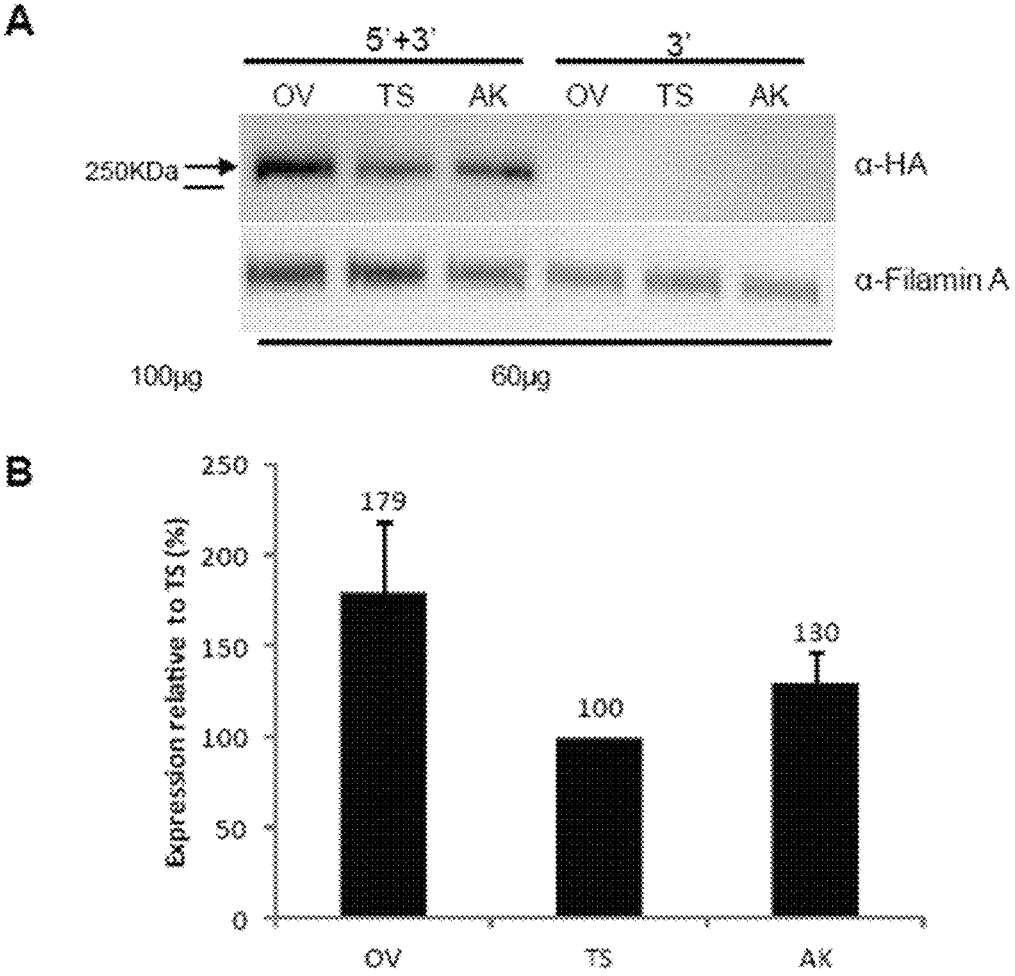

FIG. 12. Dual AAV trans-splicing and hybrid AK vectors efficiently transduce the large gene CEP290 in vitro.

Western blot of HEK293 cells infected with AAV2/2 vectors encoding for CEP290 tagged at its C-terminus with the hemagglutinin (HA) tag (A-B). (A) The arrow indicate the full-length protein, 60 micrograms of proteins were loaded for each lane, the molecular weight ladder is depicted on the left. (B) Quantification of CEP290 protein bands. The intensity of the CEP290 bands was divided by the intensity of the Filamin A bands. The histogram shows the expression of proteins as a percentage relative to dual AAV trans-splicing (TS) vectors, the mean value is depicted above the corresponding bar. Error bars: mean±s.e.m. (standard error of the mean). The Western blot image is representative of and the quantification is from n=5 independent experiments. OV: dual AAV overlapping; TS: dual AAV trans-splicing; AK: dual AAV hybrid AK; 5'+3': cells co-infected with 5'- and 3'-half vectors; 3': control cells infected with the 3'-half only; α-HA: anti-HA antibody; α-Filamin A: anti-filamin A antibody.

Figure 13:
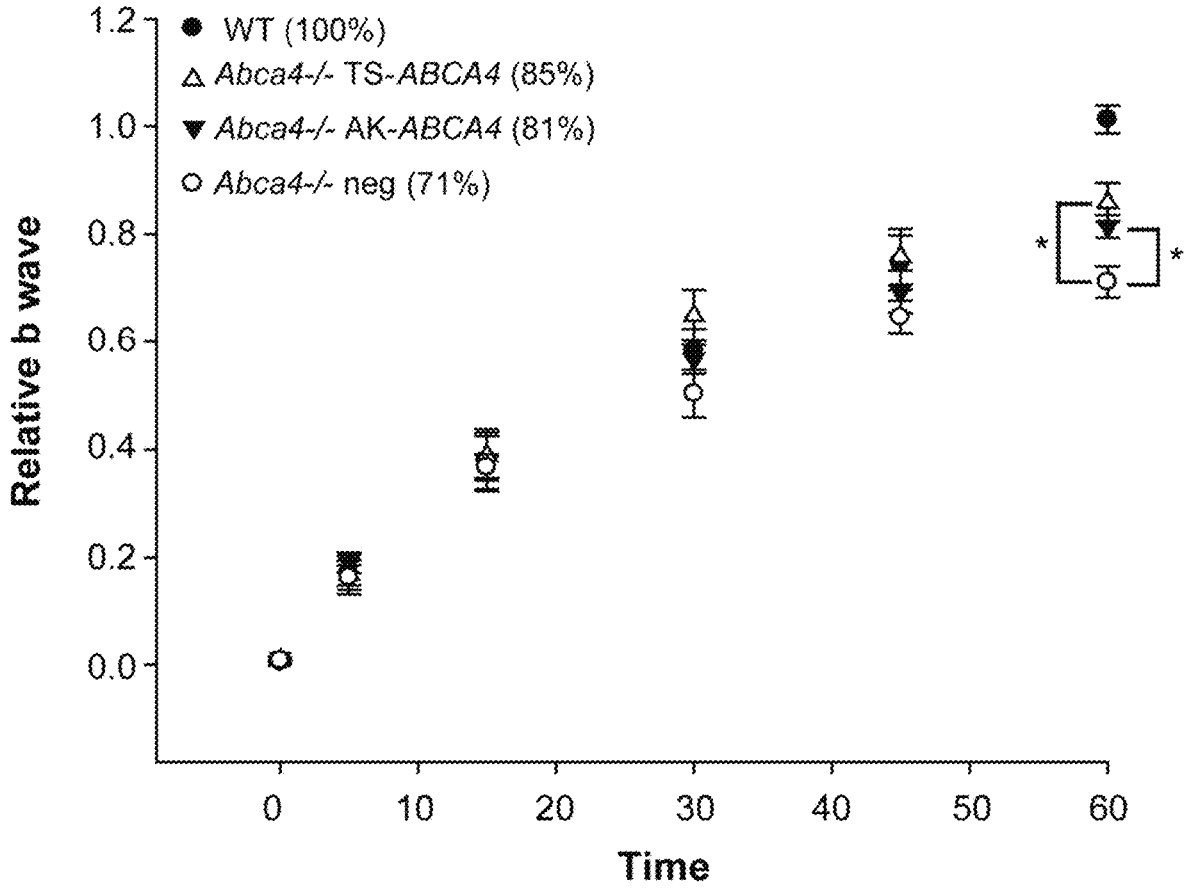

FIG. 13. Improved recovery from light desensitization in 3 months old Abca4−/− mice treated with dual AAV trans-splicing and hybrid AK vectors Recovery from light desensitization in Abca4−/− and Balb/c mice at 6 weeks post-injection. The relative b-wave is the ratio between the post- and the pre-desensitization b-wave amplitudes (μV) both evoked by 1 cd s/$m^2$. The time (minutes) refers to the time post-desensitization. The mean recovery (%) at 60 minutes is depicted. p ANOVA Abca4−/− AK-ABCA4 vs Abca4−/− uninjected/5': 0.05; p ANOVA Abca4−/− TS-ABCA4 vs Abca4−/− uninjected/5': 0.009; p ANOVA Abca4−/− AK-ABCA4 vs WT: 0.002; p ANOVA Abca4−/− TS-ABCA4 vs WT: 0.02; p ANOVA WT vs Abca4−/− uninjected/5': 0.00001. WT: Balb/c mice (n=4); Abca4−/− TS-ABCA4: mice injected with dual AAV trans-splicing vectors (n=5); Abca4−/− AK-ABCA4: mice injected with dual AAV hybrid AK vectors (n=5); Abca4−/− uninjected/5': Abca4−/− mice either not injected (n=2) or injected with the 5' half of the dual AAV TS or hybrid AK vectors (n=5). Data are depicted as mean±s.e.m (standard error of the mean). * p ANOVA<0.05.

Figure 14:
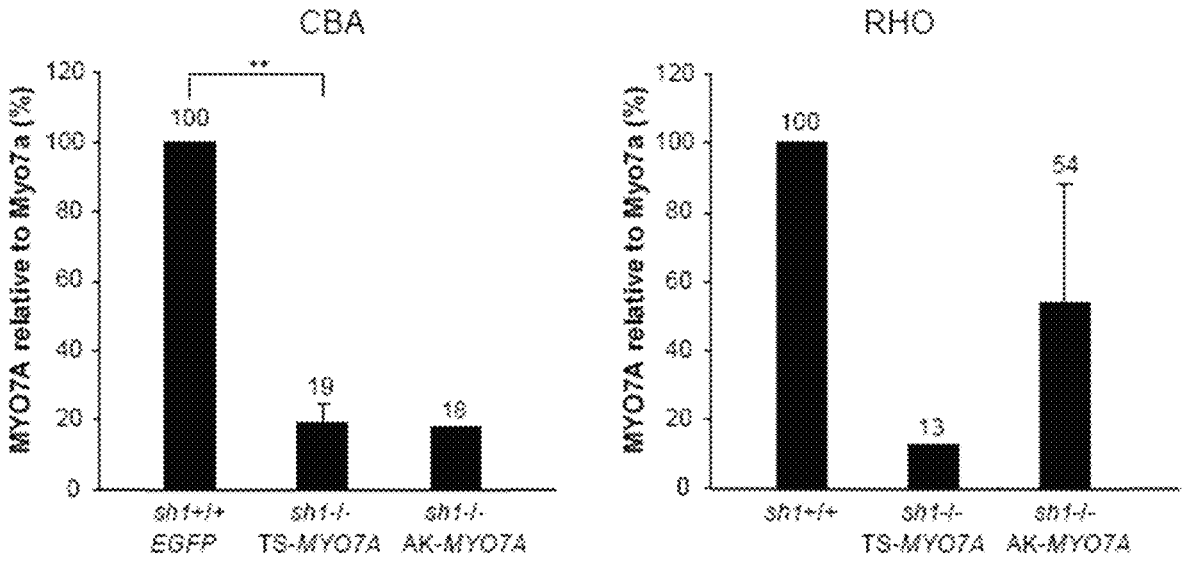

FIG. 14. Dual AAV hybrid AK vectors induce stronger MYO7A expression than dual AAV trans-splicing vectors in sh1−/− photoreceptors.

Quantification of MYO7A levels from dual AAV vectors in sh1−/− eyes relative to endogenous Myo7a expressed in sh1+/+ eyes. Sh1−/− eyes were injected with dual AAV TS and hybrid AK vectors encoding MYO7A under the control of either the CBA (left panel) or RHO (right panel) promoters. The histograms show the expression of MYO7A protein as percentage relative to sh1+/+Myo7a; the mean value is depicted above the corresponding bar. The quantification was performed by Western blot analysis using the anti-MYO7A antibody and measurements of MYO7A and Myo7a band intensities normalized to Dysferlin (data not shown). Error bars: mean±s.d.m. (standard deviation of the mean). The quantification is representative of: i. left panel: n=2 sh1+/+ eyecups, and n=5 or n=1 sh1−/− eyecups treated with either TS-MYO7A or AK-MYO7A, respectively; ii. right panel: n=2 sh1+/+ retinas, and n=1 or n=3 sh1−/− retinas treated with either TS-MYO7A or AK-MYO7A, respectively. ** p Student's t-test<0.001.

Figure 15:
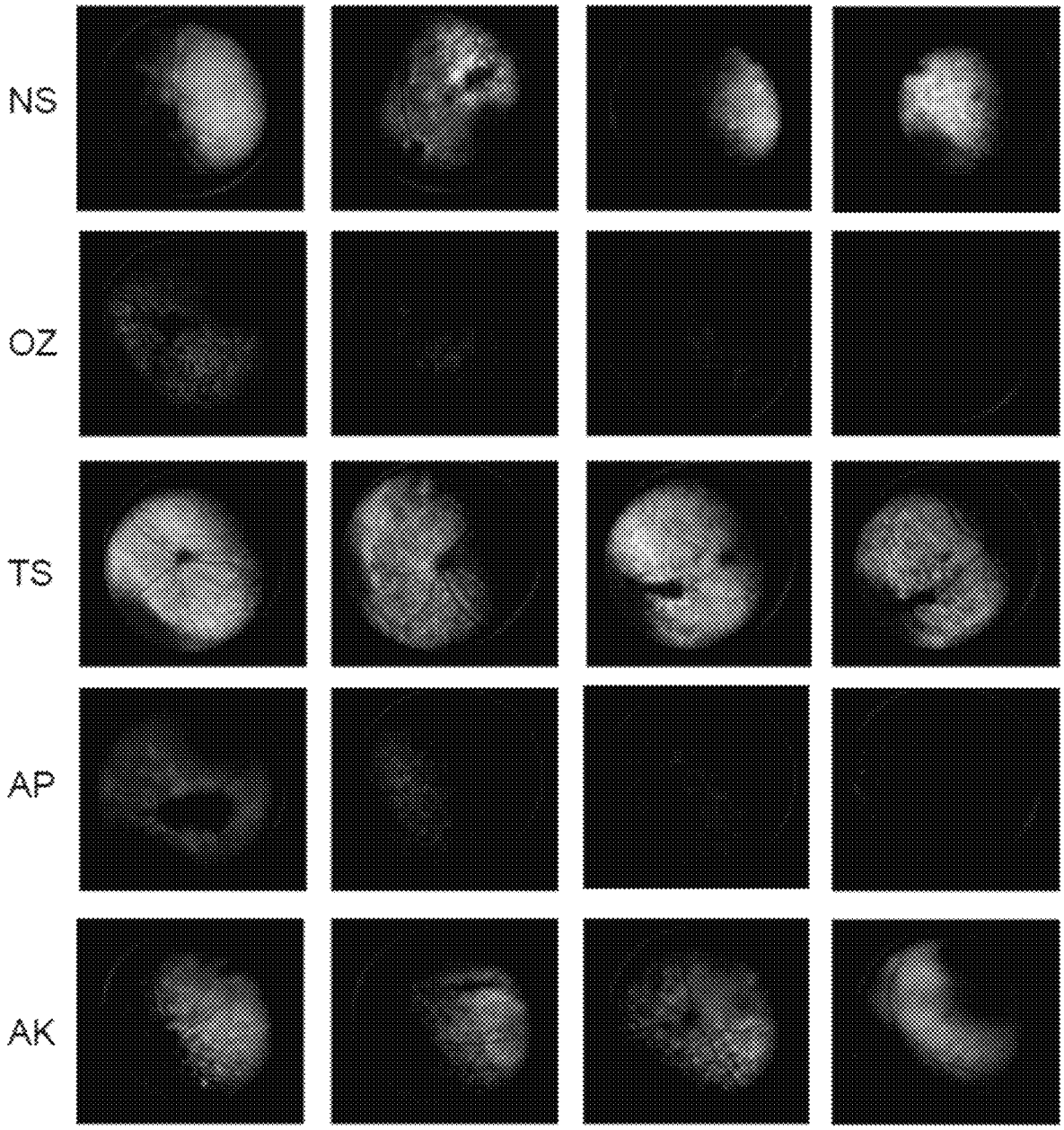

FIG. 15. AAV normal size, dual AAV trans-splicing and hybrid AK vectors provide the most robust transduction following subretinal delivery in mice.

Live-imaging fundus fluorescence of C57BL/6 eyes one month following subretinal injection of AAV2/8 vectors encoding for EGFP. NZ: Normal Size; OZ: AAV oversize; TS: dual AAV trans-splicing; AP: dual AAV hybrid AP; AK: dual AAV hybrid AK. Each panel shows a different eye.

Figure 16:
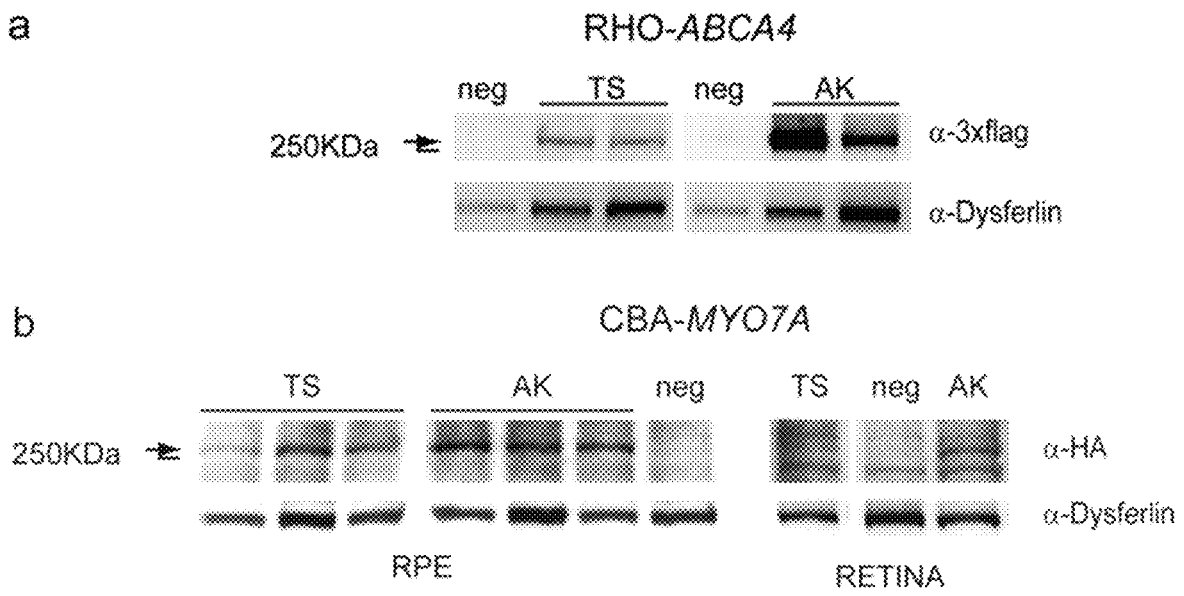

FIG. 16. Robust ABCA4 and MYO7A expression following delivery of dual AAV trans-splicing and hybrid AK vectors to the pig retina. (a) Western blot analysis of large white pig retinal lysates 1 month following injection of dual AAV2/8 trans-splicing (TS; n=2) and hybrid AK (AK; n=3) vectors encoding for ABCA4-3×flag or AAV2/8 vectors encoding for NS EGFP (neg), as negative control, under the control of the photoreceptor-specific rhodopsin (RHO) promoter. (b) Western blot analysis of large white pig retinal lysates one month following injection of dual AAV2/8 trans-splicing (TS: n=5 RPE; n=3 retina) and hybrid AK (AK: n=5 RPE, n=5 retina) vectors encoding for MYO7A-HA under the control of the ubiquitous chicken beta actin (CBA) promoter or single 3'-half of dual AAV-MYO7A-HA (neg), as negative control. (a-b) The arrows indicate full-length proteins, the molecular weight ladder is depicted on the left, 150-180 μg of proteins were loaded in each lane. α-3×flag, anti-3×flag antibody; α-HA, anti-hemagglutinin antibody; α-dysferlin, anti-dysferlin antibody.

Figure 17:
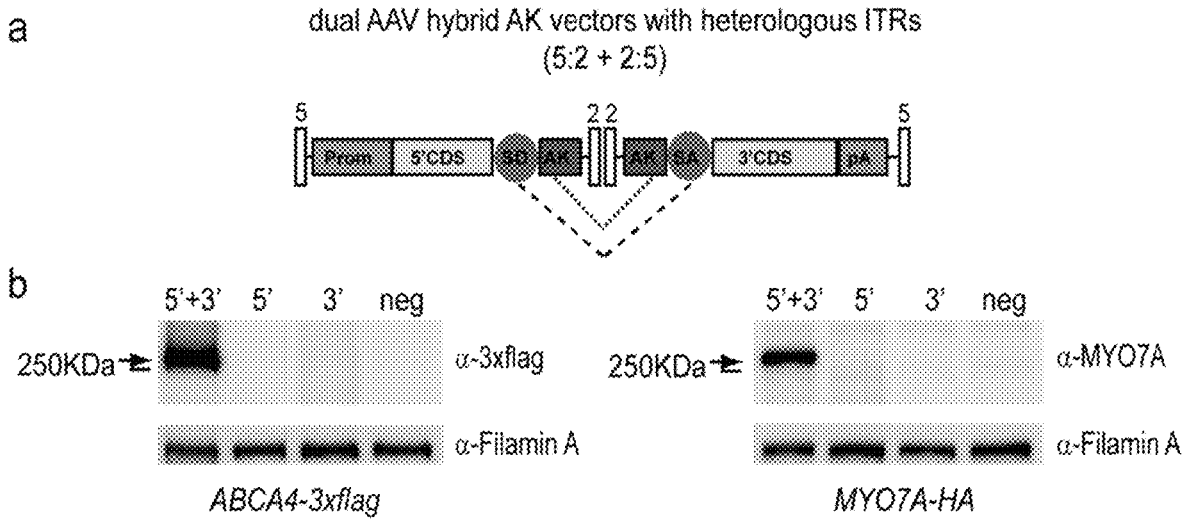

FIG. 17. Dual AAV hybrid AK vectors with heterologous ITRs transduce large genes in vitro. (a) Design of dual AAV hybrid AK vectors with heterologous ITR2 and ITR5. (b) Western blot analysis of HEK293 cells infected with dual AAV hybrid AK vectors with heterologous ITRs encoding for ABCA4 (left panel) and MYO7A (right panel). The arrows indicate full-length proteins, 50 micrograms of proteins were loaded, the molecular weight ladder is depicted on the left. 5'+3': cells co-infected with 5'- and 3'-half vectors; 5': control cells infected with the 5'-half vector only; 3': control cells infected with the 3'-half vector only; neg: cells infected with AAV2/8 vectors encoding for EGFP. α-3×flag: anti-3×flag antibody; α-MYO7A: anti-MYO7A antibody; α-Filamin: anti-filamin A antibody. (a) Prom: promoter; CDS: coding sequence; pA: poly-adenylation signal; SD: splicing donor signal; SA: splicing acceptor signal; Pointed lines show overlapping regions available for homologous recombination, dotted lines show the splicing occurring between SD and SA. The position of the heterologous ITR2 and ITR5 is depicted.

DETAILED DESCRIPTION OF THE INVENTION

Materials and Methods

Generation of AAV Vector Plasmids

The plasmids used for AAV vector production were derived from either the pZac2.1 (52) or pAAV2.1 (53) plasmids that contain the inverted terminal repeats (ITRs) of AAV serotype 2 (Table 1).

TABLE 1

Plasmids for AAV vector production.

| | Plasmid | Size ITR- ITR (bp) | AAV serotype 2/2 | AAV serotype 2/8 |
|---|---|---|---|---|
| Normal Size (NS) | pZac2.1-CMV-EGFP-SV40 | 3006 | X | X |
| | pZac2.1-RHO-EGFP-SV40 | 2900 | | X |
| Oversize (OZ) | pAAV2.1-CMV-EGFP-9.9-BGH | 9951 | X | X |
| | pZac2.1-CMV-ABCA4_3xflag-SV40 | 8619 | X | |
| | pAAV2.1-CBA-MYO7A_HA-BGH | 8220 | X | |
| Overlapping (OV) | pZac2.1-CMV-ABCA4_5' | 4900 | X | X |
| | pZac2.1-RHO-ABCA4_5' | 4805 | | X |
| | pZac2.1-RHOK-ABCA4_5' | 4169 | | X |
| | pZac2.1-VMD2-ABCA4_5' | 4658 | | X |
| | pAAV2.1-CBA-MYO7A_5' | 4708 | X | X |
| | pAAV2.1-RHO-MYO7A_5' | 4699 | | X |
| | pZac2.1-ABCA4_3'_3xflag_SV40 | 4740 | X | X |
| | pAAV2.1-MYO7A_3'_HA_BGH | 4655 | X | X |
| Trans-splicing (TS) | pZac2.1-CMV-ABCA4 _5'TS | 4431 | X | |
| | pZac2.1-RHO-ABCA4_ 5'TS | 4321 | | X |
| | pZac2.1-ABCA4 _3'TS_3xflag_SV40 | 4587 | X | X |
| | pAAV2.1-CBA-MYO7A _5'TS | 4468 | X | X |
| | pAAV2.1-RHO-MYO7A _5'TS | 4459 | | X |
| | pAAV2.1-MYO7A_3'TS_HA_BGH | 4298 | X | X |
| | pZac2.1-CMV-EGFP_5'TS | 1906 | X | X |
| | pZac2.1-RHO-EGFP_5'TS | 1802 | | X |
| | pZac2.1-EGFP_3'TS_SV40 | 1510 | X | X |
| Hybrid AP (AP) | pZac2.1-CMV-ABCA4_5'AP | 4708 | X | |
| | pZac2.1-ABCA4 _3'AP_3xflag_SV40 | 4871 | X | |
| | pAAV2.1-CBA-MYO7A_5'AP | 4746 | X | |
| | pAAV2.1-MYO7A_3'AP_HA_BGH | 4576 | X | |
| | pZac2.1-CMV-EGFP_5'AP | 2183 | X | X |
| | pZac2.1-EGFP_3'AP_SV40 | 1783 | X | X |
| Hybrid AK (AK) | pZac2.1-CMV-ABCA4 _5'AK | 4540 | X | |
| | pZac2.1 (ITR5:2)-CMV-ABCA4_5'AK | 4604 | X | |
| | pZac2.1-RHO-ABCA4_ 5'AK | 4436 | | X |
| | pZac2.1-ABCA4 _3'AK_3xflag_SV40 | 4702 | X | X |
| | pZac2.1 (ITR2:5)- ABCA4 _3'AK_3xflag_SV40 | 5192 | X | |
| | pZac2.1-ABCA4_ 3'AK_HA_SV40 | 4663 | | X |
| | pAAV2.1-CBA-MYO7A_5'AK | 4577 | X | X |
| | pAAV2.1 (ITR5:2)-CBA-MYO7A_5'AK | 4503 | X | |
| | pAAV2.1-RHO-MYO7A _5'AK | 4568 | | X |

TABLE 1-continued

Plasmids for AAV vector production.

| Plasmid | Size ITR- ITR (bp) | AAV serotype 2/2 | 2/8 |
|---|---|---|---|
| pAAV2.1-MYO7A_3'AK_HA_BGH | 4421 | X | X |
| pAAV2.1 (ITR2:5)-MYO7A_3'AK_HA_BGH | 4386 | X | |
| pZac2.1-CMV-EGFP_5'AK | 2015 | X | X |
| pZac2.1-RHO-EGFP_5'AK | 1911 | | X |
| pZac2.1-EGFP_3'AK_SV40 | 1614 | X | X |

N.B. CMV: cytomegalovirus promoter; CBA: chicken beta-actin; RHO: human Rhodopsin promoter; RHOK: human Rhodopsin kinase promoter; Vmd2: vitelliform macular dystrophy 2 promoter; EGFP: enhanced green fluorescent protein; ABCA4: human ATP-binding cassette, sub-family A, member 4; MYO7A: human MYOSIN VIIA; SV40: simian virus 40 poly-adenilation signal; BGH: bovine growth hormone poly-adenilation signal; 3xflag: 3xflag tag; HA: hemagglutinin tag; AP: alkaline phosphatase recombinogenic region; AK: F1 phage recombinogenic region; TS: trans-splicing; ITR5:2: plasmid with the left ITR from AAV serotype 5 and the right ITR from AAV serotype 2; ITR2:5: plasmid with the left ITR from AAV serotype 2 and the right ITR from AAV serotype 5. When not specified the left and right ITR are from AAV serotype 2.

Normal size and oversize AAV vector plasmids contained full length expression cassettes including the promoter, the full-length transgene CDS and the poly-adenilation signal (pA) (Table 1). The two separate AAV vector plasmids (5' and 3') required to generate dual AAV vectors contained either the promoter followed by the N-terminal portion of the transgene CDS (5' plasmid) or the C-terminal portion of the transgene CDS followed by the pA signal (3' plasmid, Table 1). Normal size EGFP plasmids were generated by cloning the EGFP CDS of pAAV2.1-CMV-EGFP plasmid (720 bp) (53) in pZac2.1 (52); oversize EGFP was generated from pAAV2.1-CMV-EGFP (53) by inserting a DNA stuffer sequence of 3632 bp from human ABCA4 (NM_000350.2, bp 1960-5591) upstream of the CMV promoter and a second DNA stuffer sequence of 3621 bp, composed of: murine ABCA4 (NM 007378.1, 1066-1 and 7124-6046 bp; 2145 total bp) and human Harmonin (NM153676.3 131-1606 bp; 1476 total bp), downstream of the pA signal (This construct was used in the experiments of FIG. 1a, d, FIG. 4 and FIG. 15). To generate dual AAV vector plasmids, the EGFP CDS (720 bp) was split into two constructs: one containing the N-terminal CDS (PMID: 9759496, bp 1-393) and the other containing the C-terminal CDS (PMID: 9759496, bp 394-720).

The oversize ABCA4 plasmids contained the full-length human ABCA4 CDS (GeneNM_000350.2, bp 105-6926), while the oversize MYO7A plasmids contained the full-length human MYO7A CDS from isoform 1 (NM_000260.3, bp 273-6920). To generate plasmids for dual AAV OV vectors the ABCA4 and MYO7A CDS were split into two constructs, one containing N-terminal CDS (ABCA4: NM_000350.2, bp 105-3588; MYO7A: NM_000350.2, bp 273-3782) and the other containing C-terminal CDS (ABCA4: NM_000350.2, bp 2819-6926; MYO7A: NM_000350.2, bp 2913-6920). Therefore, the region of homology shared by overlapping vector plasmids was 770 bp for ABCA4 and 870 bp for MYO7A. To generate plasmids for dual AAV OV vectors the human CEP290 CDS was split into two constructs, one containing N-terminal CDS (CEP290: NM_025114, bp 345-4076) and the other containing C-terminal CDS (CEP290: NM_025114, bp 3575-7784). Therefore, the region of homology shared by overlapping vector plasmids was 502 bp.

To generate trans-splicing and hybrid vector plasmids the ABCA4 and MYO7A CDS were split at a natural exon-exon junction. ABCA4 was split between exons 19-20 (5' half: NM_000350.2, 105-3022 bp; 3' half: NM_000350.2, bp 3023-6926) and MYO7A was split between exons 24-25 (5' half: NM_000350.2, bp 273-3380; 3' half: NM_000350.2, bp 3381-6926). The ABCA4 and MYO7A proteins were both tagged at their C-terminus: ABCA4 with either the 3×flag (gactacaaagaccatgacggtgattataaagatcatgacatcgactacaaggatgacgatgacaag) (*SEQ ID NO: 30*) or hemagglutinin (HA) tag (tatccgtatgatgtgccggattatgcg) (*SEQ ID NO:32*) ; MYO7A with the HA tag only. To generate trans-splicing and hybrid vector plasmids the CEP290 CDS was split at a natural exon-exon junction: between exons 29-30 (5' half: NM_025114, 345-3805; 3' half: NM_025114, 3806-7784). The CEP290 protein was tagged at its C-terminus with the hemagglutinin (HA) tag. The splice donor (SD) and splice acceptor (SA) signals contained in trans-splicing and hybrid dual AAV vector plasmids are as follows:

5'GTAAGTATCAAGGTTACAAGACAGGTTTAAGGAGACCAATAGAAACTG GGCTTGTCGAGACAGAGAAGACTCTTGCGTTTCT-3' (SD) SEQ ID No. 1;

5'GATAGGCACCTATTGGTCTTACTGACATCCACTTTGCCTTTCTCTCCA CAG-3' (SA), SEQ ID No. 2.

The recombinogenic sequence contained in hybrid AP vector plasmids (present in both first and second plasmids) were derived from alkaline phosphate (AP) genes (NM_001632, bp 823-1100), as previously described (39). The recombinogenic sequence contained in hybrid AK vector plasmids (present in both first and second plasmids) were derived from the phage F1 genome (Gene Bank accession number: J02448.1; bp 5850-5926). The AK sequence is:

5'GGGATTTTGCCGATTTCGGCCTATTGGT-TAAAAAATGAGCTGATTTAACAAAAATT-TAACGCGAATTTTAACAAAAT-3', SEQ ID No. 3.

The ubiquitous CMV promoter is that contained in pZac2.1 (52) or pAAV2.1-CMV-EGFP (53); the ubiquitous CBA promoter was derived from pAAV2.1-CBA-EGFP (11), the PR-specific human RHO and RHOK promoters were derived from pAAV2.1-RHO-EGFP and pAAV2.1RHOK-EGFP, respectively (10); the RPE-specific Vmd2 promoter (NG_009033.1, 4870-5470 bp) corresponds to the previously described EcoRI-XcmI promoter fragment (41) and was amplified by human genomic DNA.

To generate dual AAV hybrid AK vectors with heterologous ITRs from AAV serotype 2 and 5 we exchanged the left ITR2 of the 5'-half plasmid and the right ITR2 of the 3'-half plasmid with the ITR5 (as depicted in FIG. 17a). The plasmids for the production of AAV2 vectors with heterologous ITRs are the following: pZac5:2-CMV-5'ABCA4-SD- AK, pZac2:5-AK-SD-3'ABCA4-3×flag, pAAV5:2-CBA-5'MYO7A-SD-AK and pAAV2:5-AK-SD-3'MYO7A-HA (Table 1).

For the purposes of this invention, a coding sequence of ABCA4, MYO7A and CEP290 which are preferably respectively selected from the sequences herein enclosed, or sequences encoding the same amino acid sequence due to the degeneracy of the genetic code, is functionally linked to a promoter sequence able to regulate the expression thereof in a mammalian retinal cell, particularly in photoreceptor cells. Suitable promoters that can be used according to the invention include the cytomegalovirus promoter, Rhodopsin promoter, Rhodopsin kinase promoter, Interphotoreceptor retinoid binding protein promoter, vitelliform macular dystrophy 2 promoter, fragments and variants thereof retaining a transcription promoter activity.

Viral delivery systems include but are not limited to adenoviral vectors, adeno-associated viral (AAV) vectors, pseudotyped AAV vectors, herpes viral vectors, retroviral vectors, lentiviral vectors, baculoviral vectors. Pseudotyped AAV vectors are those which contain the genome of one AAV serotype in the capsid of a second AAV serotype; for example an AAV2/8 vector contains the AAV8 capsid and the AAV 2 genome (Auricchio et al. (2001) Hum. Mol. Genet. 10(26):3075-81). Such vectors are also known as chimeric vectors. Other examples of delivery systems include ex vivo delivery systems, which include but are not limited to DNA transfection methods such as electroporation, DNA biolistics, lipid-mediated transfection, compacted DNA-mediated transfection.

The construction of an AAV vector can be carried out following procedures and using techniques which are known to a person skilled in the art. The theory and practice for adeno-associated viral vector construction and use in therapy are illustrated in several scientific and patent publications (the following bibliography is herein incorporated by reference: Flotte T R. Adeno-associated virus-based gene therapy for inherited disorders. Pediatr Res. 2005 December; 58(6):1143-7; Goncalves M A. Adeno-associated virus: from defective virus to effective vector, Virol J. 2005 May 6; 2:43; Surace E M, Auricchio A. Adeno-associated viral vectors for retinal gene transfer. Prog Retin Eye Res. 2003 November; 22(6):705-19; Mandel R J, Manfredsson F P, Foust K D, Rising A, Reimsnider S, Nash K, Burger C. Recombinant adeno-associated viral vectors as therapeutic agents to treat neurological disorders. Mol Ther. 2006 March; 13(3):463-83).

Suitable administration forms of a pharmaceutical composition containing AAV vectors include, but are not limited to, injectable solutions or suspensions, eye lotions and ophthalmic ointment. In a preferred embodiment, the AAV vector is administered by subretinal injection, e.g. by injection in the subretinal space, in the anterior chamber or in the retrobulbar space. Preferably the viral vectors are delivered via subretinal approach (as described in Bennicelli J, et al Mol Ther. 2008 Jan. 22; Reversal of Blindness in Animal Models of Leber Congenital Amaurosis Using Optimized AAV2-mediated Gene Transfer).

The doses of virus for use in therapy shall be determined on a case by case basis, depending on the administration route, the severity of the disease, the general conditions of the patients, and other clinical parameters. In general, suitable dosages will vary from $10^8$ to $10^{13}$ vg (vector genomes)/eye.

AAV Vector Production

AAV vectors were produced by the TIGEM AAV Vector Core by triple transfection of HEK293 cells followed by two rounds of CsCl2 purification (54). For each viral preparation, physical titers [genome copies (GC)/ml] were determined by averaging the titer achieved by dot-blot analysis (55) and by PCR quantification using TaqMan (54) (Applied Biosystems, Carlsbad, Calif.).

AAV Infection of HEK293 Cells

HEK293 cells were maintained in Dulbecco's modified Eagle's medium (DMEM) containing 10% fetal bovine serum and 2 mM L-glutamine (GIBCO, Invitrogen S.R.L., Milan, Italy). Cells were plated in six-well plates at a density of $2\times10^6$ cells/well and transfected 16 hours later with 1.3 μg of pDeltaF6 helper plasmid which contains the Ad helper genes (56) using the calcium phosphate method. After 5 hours, cells were washed once with DMEM and incubated with AAV2/2 vectors (m.o.i: $10^5$ GC/cell of each vector; 1:1 co-infection with dual AAV vectors resulted in of $2\times10^5$ total GC/cell) in a final volume of 700 μL serum-free DMEM. Two hours later 2 ml of complete DMEM was added to the cells. Cells were harvested 72 hours following infection for Western blot analysis.

Animal Models

This study was carried out in accordance with the NIH Guide for the Care and Use of Laboratory Animals, the Association for Research in Vision and Ophthalmology Statement for the Use of Animals in Ophthalmic and Vision Research, and the Italian Ministry of Health regulation for animal procedures. Mice were housed at the Institute of Genetics and Biophysics animal house (Naples, Italy) and maintained under a 12-hour light/dark cycle (10-50 lux exposure during the light phase). C57BL/6 and BALB/c mice were purchased from Harlan Italy SRL (Udine, Italy). Albino Abca4−/− mice were generated through successive crosses and backcrosses with BALB/c mice (homozygous for Rpe65 Leu450) (57) and maintained inbred. Breeding was performed crossing homozygous mice. Pigmented sh14626SB/4626SB (referred to as sh1−/−) mice were imported from the Wellcome Trust Sanger Institute (Cambridge, UK, a kind gift of Dr. Karen Steel) and back-crossed twice with CBA/Ca mice purchased from Harlan Italy SRL (Udine, Italy) to obtain heterozygous sh1+/4626SB (referred to as sh1+/−) mice to expand the colony. The mice were maintained intercrossed; breeding was performed crossing heterozygous females with heterozygous males. The pigmented sh1 mice used in this study were either Usher 1B affected (sh1−/−) or unaffected (sh1+/− and sh1+/+). The genotype for the $MYO7A^{4626SB}$ allele was performed by PCR analysis of genomic DNA (extracted from the mouse tail tip) followed by DNA sequencing. The primers used for the PCR amplification are as follows: Fw1 (GTGGAGCTTGACATCTACTTGACC) (*SEQ ID NO: 33*) and Rev3 (AGCTGACCCTCATGACTCTGC) (*SEQ ID NO: 34*), which generate a product of 712 bp that was sequenced with the Fw1 primer. The Large White Female pigs used in this study were registered as purebred in the LWHerd Book of the Italian National Pig Breeders' Association (Azienda Agricola Pasotti, Imola, Italy).

Subretinal Injection of AAV Vectors in Mice and Pigs

Mice (4-5 weeks-old) were anesthetized with an intraperitoneal injection of 2 ml/100 g body weight of avertin [1.25% w/v of 2,2,2-tribromoethanol and 2.5% v/v of 2-methyl-2-butanol (Sigma-Aldrich, Milan, Italy)] (58), then AAV2/8 vectors were delivered subretinally via a trans-scleral transchoroidal approach as described by Liang et al (59). All eyes were treated with 1 μL of vector solution. The AAV2/8 doses (GC/eye) delivered vary across the different mouse experiments as it is described in the "RESULTS" section. AAV2/1-CMV-human Tyrosinase (60)

(dose: $2\times10^8$ GC/eye) or AAV2/5-CMV-EGFP (encoding normal size EGFP, dose: $4\times10^8$ GC/eye) was added to the AAV2/8 vector solution that was subretinally delivered to albino (Abca4−/− and BALB/c) (FIG. 6B, 7-8) or pigmented sh1 mice (FIG. 10-11), respectively. This allowed us to mark the RPE within the transduced part of the eyecup, which was subsequently dissected and analyzed. (FIG. 6B, 7-8, 10-11). Subretinal delivery of AAV vectors to the pig retina was performed as previously described (11). All eyes were treated with 100 μL of AAV2/8 vector solution. The AAV2/8 dose was $1\times10^{10}$ (FIG. 3B) or $1\times10^{11}$ GC of each vector/eye (FIGS. 5B and 16) and co-injection of dual AAV vectors resulted in a total dose of $2\times10^{10}$ GC/eye or $2\times10^{11}$ GC/eye, respectively.

Western Blot Analysis

Samples (HEK293 cells, retinas or eyecups) for Western blot analysis were lysed in RIPA buffer (50 mM Tris-Hcl pH 8.0, 150 mM NaCl, 1% NP40, 0.5% Na-Deoxycholate, 1 mM EDTA pH 8.0, 0.1% SDS) to extract EGFP and MYO7A proteins, or in SIE buffer (250 mM sucrose, 3 mM imidazole pH 7.4, 1% ethanol, and 1% NP-40) to extract ABCA4 protein.

Pig samples (the treated areas of the retina as well as whole RPE sheets) were lysed in RIPA buffer to extract MYO7A from RPE sheets, and in SIE buffer to extract MYO7A and ABCA4 from retinas.

Lysis buffers were supplemented with protease inhibitors (Complete Protease inhibitor cocktail tablets, Roche, Milan, Italy) and 1 mM phenylmethylsulfonyl. After lysis EGFP and MYO7A samples were denatured at 99° C. for 5 minutes in 1× Laemli Sample buffer; ABCA4 samples were denatured at 37° C. for 15 minutes in 1× Laemli sample buffer supplemented with 4M urea. Lysates were separated by 7% (ABCA4 and MYO7A samples) or 12% (EGFP samples) SDS-polyacrylamide gel electrophoresis. The antibodies used for immuno-blotting are as follows: anti EGFP (sc-8334, Santa Cruz, Dallas, Tex., USA, 1:500); anti-3×flag (A8592, Sigma-Aldrich, 1:1000); anti-Myo7a (polyclonal, Primm Srl, Milan, Italy, 1:500) generated using a peptide corresponding to aminoacids 941-1070 of the human MYO7A protein; anti-HA antibody (PRB-101P-200, HA.11, Covance, Princeton, N.J., USA, 1:2000); anti-β Tubulin (T5201, Sigma Aldrich, 1:10000); anti-Filamin A (catalog#4762, Cell Signaling Technology, Danvers, Mass., USA, 1:1000); anti-Dysferlin (Dysferlin, clone Ham1/7B6, MONX10795, Tebu-bio, Le Perray-en-Yveline, France, 1:500). The quantification of EGFP, ABCA4 and MYO7A bands detected by Western blot was performed using ImageJ software (free download is available at http://rsbweb.nih.gov/ij/). ABCA4 and MYO7A expression was normalized to Filamin A or Dysferlin for the in vitro and in vivo experiments, respectively. EGFP expression was normalized to β-Tubulin or μg of proteins for in vitro and in vivo experiments, respectively. Different proteins were used for normalization based on the similarity of their molecular weight to those of the different transgene products.

Fundus Photography

The fundus live-imaging was performed by dilating the eye of C57BL/6 with a drop of tropicamide 1% (Visufarma, Rome, Italy) and subsequent eye stimulation with a 300 W flash. Fundus photographs were taken using a Topcon TRC-50IX retinal camera connected to a charge-coupled-device Nikon D1H digital camera (Topcon Medical System, Oakland, N.J., USA).

Histology, Light and Fluorescence Microscopy

To evaluate EGFP expression in histological sections, eyes from C57BL/6 mice or Large White pigs (11) were enucleated one month after AAV2/8 injection. Mouse eyes were fixed in 4% paraformaldehyde over-night and infiltrated with 30% sucrose over-night; the cornea and the lens were then dissected and the eyecups were embedded in optimal cutting temperature compound (O.C.T. matrix, Kaltek, Padua, Italy). Pig eyes were fixed in 4% paraformaldehyde for 48 hours, infiltrated with 10% sucrose for 4 hours, 20% sucrose for 4 hours and finally 30% sucrose overnight. Then, the cornea, the lens, and the vitreous body were dissected and the EGFP-positive portions of the eyecups were embedded in optimal cutting temperature compound (O.C.T. matrix, Kaltek). Serial cryosections (10 μm thick) were cut along the horizontal meridian and progressively distributed on slides. Retinal histology pictures were captured using a Zeiss Axiocam (Carl Zeiss, Oberkochen, Germany). To analyze melanosome localization in the RPE of pigmented sh1 mice, eyes were enucleated 2 months following the AAV injection, fixed in 2% glutaraldehyde-2% paraformaldehyde in 0.1M phosphate buffer over-night, rinsed in 0.1M phosphate buffer, and dissected under a florescence microscope. The EGFP-positive portions of the eyecups were embedded in Araldite 502/EMbed 812 (catalog #13940, Araldite 502/EMbed 812 KIT, Electron Microscopy Sciences, Hatfield, Pa., USA). Semi-thin (0.5-μm) sections were transversally cut on a Leica Ultratome RM2235 (Leica Microsystems, Bannockburn, Ill., USA), mounted on slides, and stained with Epoxy tissue stain (catalog #14950, Electron Microscopy Sciences). Melanosomes were counted by a masked operator analyzing 10 different fields/eye under a light microscope at 100× magnification. Retinal pictures were captured using a Zeiss Axiocam (Carl Zeiss).

Electron Microscopy and Immuno-Gold Labelling

For electron microscopy analyses eyes were harvested from Abca4−/− or sh1 mice at 3 and 2 months after AAV injection, respectively. Eyes were fixed in 0.2% glutaraldehyde-2% paraformaldehyde in 0.1M PHEM buffer pH 6.9 (240 mM PIPES, 100 mM HEPES, 8 mM $MgCl_2$, 40 mM EGTA) for 2 hours and then rinsed in 0.1 M PHEM buffer. Eyes were then dissected under light or fluorescence microscope to select the Tyrosinase- or EGFP-positive portions of the eyecups of albino (Abca4−/− and BALB/c) and pigmented sh1 mice, respectively. The transduced portion of the eyecups were subsequently embedded in 12% gelatin, infused with 2.3M sucrose and frozen in liquid nitrogen. Cryosections (50 nm) were cut using a Leica Ultramicrotome EM FC7 (Leica Microsystems) and extreme care was taken to align PR connecting cilia longitudinally. Measurements of RPE thickness and counts of lipofuscin granules in Abca4−/− eyes were performed by a masked operator (Roman Polishchuk) using the iTEM software (Olympus SYS, Hamburg, Germany). Briefly, RPE thickness was measured in at least 30 different areas along the specimen length using the "Arbitrary Line" tool of iTEM software. The "Touch count" module of the iTEM software was utilized to count the number of lipofuscin granules in the 25 $\mu m^2$ areas distributed randomly across the RPE layer. The granule density was expressed as number of granules per 25 $\mu m^2$. The immuno-gold analysis aimed at testing the expression of ABCA4-HA in Abca4−/− samples after AAV vector delivery was performed by incubating cryosections successively with monoclonal anti-HA antibody (MMS-101P-50, Covance, 1:50), rabbit anti-mouse IgG, and 10-nm gold particle-conjugated protein A. To quantify rhodopsin localization to the connecting cilium of sh1 PR, cryosections of sh1 mice were successively incubated with anti-rhodopsin antibody (1D4, ab5417, Abcam, Cambridge, UK, 1:100), rabbit anti-mouse IgG, and 10-nm gold particle-conjugated protein A. The quantification of gold density of rhodospin in the connecting cilia was performed by a masked operator using iTEM software (Olympus SYS). Briefly, the "Touch count" module of the iTEM software was used to count the number of gold particles per cilium that were normalized to the cilium perimeter (nm) that was measured using the "Closed polygon tool". Gold density was expressed as gold particles/nm. Immunogold labelled cryosections were analyzed under FEI Tecnai-12 (FEI, Eindhoven, The Netherlands) electron microscope equipped with a Veletta CCD camera for digital image acquisition.

Electrophysiological Analyses

To assess the recovery from light desensitization eyes were stimulated with 3 light flashes of 1 cd s/m2 and then desensitized by exposure to constant light (300 cd/m2) for 3 minutes. Then, eyes were stimulated over time using the pre-desensitization flash (1 cd s/m2) at 0, 5, 15, 30, 45 and 60 minutes post-desensitization. The recovery of rod activity was evaluated by performing the ratio between the b-wave generated post-desensitization (at the different time points) and that generated pre-desensitization. The recovery from light desensitization was evaluated in 2-month-old Abca4−/− mice at 6 weeks post treatment (FIG. 13).

Statistical Analysis

Data are presented as mean±standard error of the mean (s.e.m.). Statistical p values<0.05 were considered significant. One-way ANOVA with post-hoc Multiple Comparison Procedure was used to compare data depicted in: FIG. 2 (p ANOVA: A. 0.0002; B. 0.0015; C. $2\times10^{-7}$); FIG. 8B (p ANOVA: 0.076); FIG. 11B (p ANOVA: 0.5). As lipofuscin granules (FIG. 7B) and melanosomes (FIG. 10B) were counted, counts were analyzed by deviance from a Negative Binomial generalized linear models (61) (FIG. 7B: p value analysis of deviance 0.03794; FIG. 10B: p value analysis of deviance$<<2\times10^{-10}$). The statistically significant differences between groups determined with the post-hoc Multiple Comparison Procedure are marked by asterisks in the Figures.

Results

Generation of Normal Size, Oversize and Dual AAV Vectors.

The inventors generated oversize (OZ), dual AAV trans-splicing (TS), and hybrid vectors that included either the reporter EGFP, the therapeutic ABCA4-3×flag or the MYO7A-HA coding sequences. The inventors also generated dual AAV trans-splicing (TS), and hybrid vectors that included the therapeutic CEP290 tagged at its C-terminus with HA tag. The recombinogenic sequences included in the dual AAV hybrid vectors were based on either a previously reported region of the alkaline phosphatase transgene (AP, dual AAV hybrid AP) (39) or a 77 bp sequence from the F1 phage genome (AK, dual AAV hybrid AK) that the inventors found to be recombinogenic in previous experiments (Colella and Auricchio, unpublished data). The inventors also generated dual AAV overlapping (OV) vectors for ABCA4, MYO7A and CEP290. The inventors did not generate dual AAV OV vectors for EGFP because the efficiency of this approach relies on transgene-specific overlaps for reconstitution (38) and therefore cannot be extrapolated from one gene to another. Instead, for EGFP the inventors generated single AAV vectors of normal size (NS) to compare levels of transgene expression from the various strategies. The constructs generated for production of all AAV vectors used in this study are listed in Table 1 and a schematic representation of the various approaches is depicted in FIG. 1.

The inventors used AAV2/2 vectors for the in vitro experiments, with the ubiquitous cytomegalovirus (CMV) or chicken beta-actin (CBA) promoters, which efficiently transduce HEK293 cells (40). In addition, since the use of heterologous ITRs from AAV serotypes 2 and 5 can increase the productive reassembly of dual AAV vectors (51), the inventors also generated dual AAV AK vectors with heterologous ITRs (FIG. 17a) encoding ABCA4 and MYO7A. AAV vectors with heterologous ITRs were packaged in AAV capsids from serotype 2 and tested in vitro.

In the experiments performed in vivo in the retina, The inventors used AAV2/8 vectors, which efficiently transduce RPE and PR (10-12) but poorly infect HEK293 cells, and either the ubiquitous CBA and CMV promoters (11), or the RPE-specific vitelliform macular dystrophy 2 (VMD2) (41) or the PR-specific Rhodopsin (RHO) and Rhodopsin kinase (RHOK) promoters (10) (Table 1).

Dual AAV Vectors Allow High Levels of Transduction In Vitro.

The inventors initially compared the efficiency of the various OZ, dual AAV OV, TS and hybrid AP and AK strategies for AAV-mediated large gene transduction in vitro by infecting HEK293 cells with the AAV2/2 vectors [multiplicity of infection, m.o.i.: $10^5$ genome copies (GC)/cell of each vector] with ubiquitous promoters (CMV for EGFP, ABCA4-3×flag, and CEP290-HA, and CBA for MYO7A-HA).

Cell lysates were analyzed by Western blot with anti-EGFP (FIG. 2A), -3×flag (to detect ABCA4-3×flag, FIG. 2B), -MYO7A (FIG. 2C) and -HA (to detect CEP290-HA) (FIG. 12A) antibodies. Representative Western blots are shown in FIGS. 2A-C and 12A. All strategies resulted in the expression of proteins of the expected size. As predicted, no bands of the expected size were observed when only one of the dual AAV vectors was used for infection (FIGS. 2A-C and 12A). Quantification of transgene expression (FIG. 2D-F) showed that the dual AAV hybrid AP approach resulted in the lowest levels of transgene expression, while the dual AAV OV, TS and hybrid AK approaches were more efficient than the AAV OZ approach. Dual AAV TS and hybrid AK approaches confirmed their ability to efficiently express large genes also in the case of CEP290 (FIG. 12B). In addition, the use of dual AAV AK vectors with heterologous ITRs resulted in expression of full-length ABCA4 and MYO7A proteins in vitro (FIG. 17).

Dual AAV TS and Hybrid AK but not OV Vectors Transduce Mouse and Pig Photoreceptors.

The inventors then evaluated each of the AAV-based systems for large gene transduction in the mouse retina. To test the dual AAV OV, which was transgene-specific, The inventors used the therapeutic ABCA4 and MYO7A genes (FIG. 3). The inventors used EGFP to evaluate the AAV OZ and the dual AAV TS, hybrid AP and AK approaches (FIG. 4). Western blot analysis on retinal lysates, one month after subretinal delivery in C57BL/6 mice of the dual AAV OV vectors (dose of each vector/eye: $1.3\times10^9$ GC), encoding ABCA4-3×flag from the ubiquitous CMV promoter, revealed robust protein expression (FIG. 3A). To determine which cell type in the retina expressed ABCA4, The inventors used dual AAV OV vectors that contained either the PR-specific RHO and RHOK, or the RPE-specific VMD2 (dose of each vector/eye: $1\times10^9$ GC) promoters. The inventors detected ABCA4 protein expression in retinas injected with the VMD2 but not in those containing the RHO and RHOK promoters (FIG. 3A). These results were also confirmed in the Large White pig retina. The pig retina is an excellent model to evaluate vector efficiency because of its size, which is similar to the human retina, and because it is enriched with cones that are concentrated in a streak-like region whose cone density is comparable to that of the primate macula (11). The inventors injected Large White pig subretinally with dual AAV OV vectors encoding ABCA4-3×flag (dose of each vector/eye: $1\times10^{10}$ GC), and observed ABCA4 protein expression with the CMV but not the RHO promoter (FIG. 3B). Similarly, subretinal administration of dual AAV OV vectors encoding MYO7A-HA resulted in weak MYO7A protein expression in the mouse retina with the ubiquitous CBA (dose of each vector/eye: $2.5\times10^{9}$ GC) and no detectable expression with the RHO (dose of each vector/eye: $3.2\times10^{9}$ GC) promoter (FIG. 3C). Overall, these data suggested that the dual AAV OV approach was more efficient for large gene transfer to RPE than to PR, which are a major target of gene therapy for IRDs, such as STGD and USH1B.

To find an AAV-based strategy that efficiently transduces large genes in PR, the inventors evaluated the retinal transduction properties of the AAV OZ and dual AAV TS, hybrid AP, and AK approaches. The inventors initially used EGFP, which allowed us to easily localize transgene expression in the various retinal cell types including PR as well as to properly compare the levels of AAV-based large transgene transduction to those of a single AAV NS vector. C57BL/6 mice were subretinally injected with AAV NS, OZ and dual AAV TS, and hybrid AP and AK vectors (dose of each vector/eye: $1.7\times10^{9}$ GC), all encoding EGFP under the transcriptional control of the CMV promoter. One month later, fundus photographs showed that the highest levels of fluorescence were obtained with the AAV NS, and dual AAV TS and hybrid AK approaches (FIG. 15). Fluorescence microscope analysis of retinal cryosections showed that detectable levels of RPE or PR transduction could be observed in: 77% (10/13) retinas injected with AAV NS and OZ vectors; 92% (12/13) retinas injected with dual AAV TS, hybrid AP and AK vectors. FIG. 4 shows the best transduced retinas from each of these groups. The most robust levels of PR transduction were obtained with the AAV NS and dual AAV TS and hybrid AK approaches.

The inventors then assessed PR-specific transduction levels in C57BL/6 mice following subretinal administration of dual AAV TS and hybrid AK vectors, which appears the most promising for large gene reconstitution in PR, as well as AAV NS vectors for comparison (dose of each vector/eye: $2.4\times10^{9}$ GC). All vectors encoded EGFP under the transcriptional control of the PR-specific RHO promoter. One month after vector administration retinas were cryosectioned and analyzed under a fluorescence microscope (FIG. 5A). All approaches resulted in high levels of PR transduction, which seemed more consistent with the single AAV NS vector. The inventors found PR transduction in: 100% (6/6) of the retinas injected with AAV NS; 60% (9/15) of the retinas injected with dual AAV TS; 71% (10/14) of the retinas injected with dual AAV hybrid AK. FIG. 5A shows the best transduced retinas from each of these groups. Thus, the inventors conclude that dual AAV TS and hybrid AK strategies allow efficient mouse PR transduction although at levels which are lower than those obtained with a NS AAV. The inventors then confirmed that subretinal administration of dual AAV TS and hybrid AK vectors (dose of each vector/eye: $1\times10^{11}$ GC; EGFP-positive retinas out of total injected: 2/2 dual AAV TS; 2/2 dual AAV hybrid AK) transduced PR of White Large pigs (FIG. 5B).

In addition, subretinal delivery to the pig retina of dual AAV TS and hybrid AK vectors (dose of each vector/eye: $1\times10^{11}$) resulted in efficient expression of both full-length ABCA4-3×flag specifically in PRs (FIG. 16a) and full-length MYO7A-HA in RPE and PRs (FIG. 16b) Interestingly, dual AAV hybrid AK vectors resulted in more consistent expression of the large ABCA4 and MYO7A proteins in PRs, compared with dual AAV TS vectors (FIG. 16).

Dual AAV Vectors Improve the Retinal Phenotype of STGD and USH1B Mouse Models.

To understand whether the levels of PR transduction obtained with the dual AAV TS and hybrid AK approaches may be therapeutically relevant, the inventors investigated them in the retina of two mouse models of IRDs, STGD and USH1B caused by mutations in the large ABCA4 and MYO7A genes, respectively.

Although the Abca4−/− mouse model does not undergo severe PR degeneration (42), the absence of the ABCA4-encoded all-trans retinal transporter in PR outer segments (43-44) causes an accumulation of lipofuscin in PR as well as in RPE, as result of PR phagocytosis by RPE (45). As a consequence, both the number of lipofuscin granules in the RPE and the thickness of RPE cells are greater in Abca4−/− mice than in control mice (45). Moreover the Abca4−/− mouse model is characterized by delayed dark adaptation (57, 62). Since ABCA4 is expressed specifically in PR, the inventors generated dual AAV TS and hybrid AK vectors encoding ABCA4-3×flag under the transcriptional control of the RHO promoter. These vectors were subretinally injected in wild-type C57BL/6 mice (dose of each vector/eye: $3\text{-}5\times10^{9}$ GC) and one month later retinas were lysed and analyzed by Western blot with anti-3×flag antibodies. Both approaches resulted in robust yet variable levels of ABCA4-3×flag expression. ABCA4-3×flag expression levels were more consistent in retina treated with the dual AAV hybrid AK vectors (FIG. 6A). These results were confirmed in Large White pigs (data not shown). In addition, one month-old albino Abca4−/− mice were injected subretinally with the dual AAV hybrid AK RHO-ABCA4-HA vectors (dose of each vector/eye: $1\text{-}3\times10^{9}$ GC). Three months later, eyes were harvested and immuno-electron microscopy analysis with anti-hemagglutinin (HA) antibodies of retinal sections confirmed that immunogold particles were correctly localized in PR outer segments only in animals that were injected with the combination of 5' and 3' dual AAV hybrid AK vectors (FIG. 6B). To assess the functionality of the ABCA4 protein expressed by the dual vectors, the inventors also performed transmission electron microscopy to assess the presence and number of RPE lipofuscin granules (FIG. 7) and RPE thickness (FIG. 8). Both were greater in the retina of Abca4−/− mice injected with control vectors than in the retina of wild-type, age-matched Balb/C controls, and were reduced or normalized in the eyes injected with the therapeutic dual AAV TS or hybrid AK vectors (FIGS. 7B and 8B). In addition, the ability of Abca4−/− photoreceptors to recover from light desensitization was significantly improved in the retinas treated with the therapeutic vectors when compared to control retinas (FIG. 13).

The inventors then tested PR transduction levels and efficacy of dual AAV-mediated MYO7A gene transfer in the retina of sh1 mice, the most commonly used model of USH1B (23-24, 46-48). In sh1 mice, a deficiency in the motor Myo7a causes the mis-localization of RPE melanosomes (47), which do not enter into the RPE microvilli, and the accumulation of rhodopsin at the PR connecting cilium (48). Since MYO7A is expressed in both RPE and PR (22-23), the inventors then used dual AAV TS and hybrid AK vectors expressing MYO7A-HA under the transcriptional control of the ubiquitous CBA promoter. One month-old wild-type C57BL/6 mice were injected with the dual AAV vectors (dose of each vector/eye: $1.7\times10^9$ GC) and eyecup lysates were evaluated one month later using Western blot analysis with anti-HA antibodies. Results showed similarly robust and consistent levels of MYO7A expression in retinas treated with both approaches (FIG. 9). Taking advantage of our anti-MYO7A antibody able to recognize both murine and human MYO7A, we compared the levels of MYO7A achieved following delivery of dual AAV vectors to the sh1−/− eye to those expressed endogenously in the sh1+/+ eye (FIG. 14). We used both the CBA (FIG. 14, left panel, dose of each vector/eye: $1\text{-}6\times10^9$GC) and the RHO promoters (FIG. 14, right panel, dose of each vector/eye: $2\times10^9$GC) to distinguish MYO7A expression achieved in both PR and RPE from that in PR alone: the former is about 20% (FIG. 14, left panel) and the latter up to about 50% of endogenous Myo7a (FIG. 14, right panel). Our analysis additionally shows that the levels of MYO7A expression achieved in PR by dual AAV hybrid AK are higher than those obtained with the dual AAV TS vectors despite the number of transduced retinas is similar (TS-MYO7A: 3 retinas positive out of 8 injected; AK-MYO7A: 4 retinas positive out of 8 treated; FIG. 14, right panel).

To test the ability of MYO7A expressed from dual AAV vectors to rescue the defects of the sh1−/− retina, the inventors then subretinally injected the CBA sets of dual AAV TS and hybrid AK vectors (dose of each vector/eye: $2.5\times10^9$ GC) in one month-old sh1 mice. The inventors assessed RPE melanosome (FIG. 10) and rhodopsin localization (FIG. 11) by analysis of semi-thin retinal section and by immuno-electron microscopy, respectively. Unlike unaffected sh1+/−, the sh1−/− melanosomes do not enter the RPE microvilli after delivery of control vectors (each single 5' half of the dual-AAV strategies, FIG. 10). The number of RPE melanosomes correctly localized apically was significantly improved after the delivery of either dual AAV TS or hybrid AK vectors encoding MYO7A (FIG. 10B). Remarkably, the inventors also found that the MYO7A expression mediated by dual AAV TS and hybrid AK vectors reduced the accumulation of rhodopsin at the connecting cilium of sh1−/− PR (FIG. 11).

Discussion

While AAV-mediated gene therapy is effective in animal models and in patients with inherited blinding conditions (5-9, 49), its application to diseases affecting the retina and requiring a transfer of genes larger than 5 kb (referred to as large genes) is inhibited by AAV limited cargo capacity. To overcome this, the inventors compared the efficiency of various AAV-based strategies for large gene transduction including: AAV OZ and dual AAV OV, TS and hybrid approaches in vitro and in mouse and pig retina. In previous experiments, inventors selected a 77 bp sequence from the F1 phage genome that the inventors identified for its recombinogenic properties and used in the dual hybrid approach (AK, dual AAV hybrid AK).

The inventors' in vitro and in vivo results show that the dual AAV hybrid AK surprisingly outperforms the dual AAV hybrid AP and that all dual AAV strategies the inventors tested (with the exception of the dual AAV hybrid AP) outperform AAV OZ vectors in terms of transduction levels. This may be explained by the homogenous size of the dual AAV genome population when compared to OZ genomes, which may favor the generation of transcriptionally active large transgene expression cassettes.

The dual AAV OV approach seems particularly interesting when compared to the TS or hybrid AK approaches as dual AAV OV vectors only contain sequences belonging to the therapeutic transgene expression cassette. However, when the inventors administered dual AAV OV vectors to the subretinal space of adult mice and pigs, the inventors were only able to detect expression of the large ABCA4 protein when the ubiquitous or the RPE-specific promoters, but not the PR-specific promoters, were used. This may suggest that the homologous recombination required for dual AAV OV reconstitution is more efficient in RPE than PR. This is consistent with the low levels of homologous recombination reported in post-mitotic neurons (50) and may partially explain the lack of dual AAV OV-mediated MYO7A transduction recently reported by other groups (30). The inventors conclude that subretinal administration of dual AAV OV vectors should not be used for large gene transfer to PR, although the inventors cannot exclude that sequences that are more recombinogenic than those included in the inventors' dual AAV OV ABCA4 and MYO7A vectors may allow efficient homologous recombination in PR.

Dual AAV TS and hybrid AK approaches efficiently transduce mouse and pig PR, differently from what the inventors observed with dual AAV OV. This is consistent with the knowledge that the mechanism of large gene reconstitution mediated by dual AAV TS and hybrid AK approaches may be via ITR-mediated head-to-tail rejoining (32, 35, 51) rather than homologous recombination.

The levels of mouse PR transduction the inventors achieved with dual AAV TS and hybrid AK is lower and less consistent than with single NS vectors. However, dual AAV may be effective for treating inherited blinding conditions that require relatively low levels of transgene expression, i.e. diseases inherited as autosomal recessive. Indeed, the inventors show that subretinal delivery of dual AAV TS and hybrid AK improves and even normalizes the retinal defects of two animal models of inherited retinal diseases, STGD and USH1B, which are due to mutations in large genes and are attractive targets of gene therapy.

The genome size of dual AAV vectors is homogenous, which means identity and safety issues related to their use should be less considerable than those related to AAV OZ vectors, which have heterogeneous genome sizes. In contrast, the inventors detected neither ERG or retinal histological abnormalities in the mice that the inventors followed up to 1-2 months after dual AAV vector delivery (data not shown).

In conclusion, the inventors identified a new recombinogenic sequence (AK) that strikingly improves the performance of the AAV dual hybrid vector system. In fact they found that dual AAV vectors are efficient both in vitro and in the retina in vivo. While dual AAV OV vectors efficiently transduce RPE, they do not transduce PR, whereas dual AAV TS and hybrid AK approaches drive efficient large gene reconstitution in both cell types. Administration of dual AAV TS and hybrid AK approaches improved the retinal phenotype of mouse models of STGD and USH1B, providing evidence of the efficacy of these strategies for gene therapy for these and other blinding conditions, which require large gene transfer to retinal PR as well as RPE. These findings will greatly broaden the application of AAV vectors for gene therapies not only to eyes, but also to muscle as well as to other organs and tissues. Diseases other than IRD caused by defective genes larger than 5 kb include non-limiting examples of muscular dystrophies, dysferlin deficiencies (limb-girdle muscular dystrophy type 2B and Miyoshi myopathy), Cystic Fibrosis, Hemophilia.

REFERENCES

1. M. M. Sohocki, et al. Hum. Mutat. 17, 42-51 (2001).
2. T. Dryja, in The Online Metabolic & Molecular Bases of Inherited Diseases C. Scriver, A. Beaudet, W. Sly, D. Valle, Eds. (McGraw-Hill, New York, N.Y., 2001), vol 4, pp. 5903-5933.
3. P. Colella, et al. Trends Mol. Med. 15, 23-31 (2009).
4. L. H. Vandenberghe, A. Auricchio, Gene Ther. 19, 162-168 (2012).
5. J. W. Bainbridge, et al. N. Engl. J. Med. 358, 2231-2239 (2008).
6. A. V. Cideciyan, et al. N. Engl. J. Med. 361, 725-727 (2009).
7. A. M. Maguire, et al. N. Engl. J. Med. 358, 2240-2248 (2008).
8. A. M. Maguire, et al. Lancet 374, 1597-1605 (2009).
9. F. Simonelli, et al. Mol. Ther. 18, 643-650 (2010).
10. M. Allocca, et al. J. Virol. 81, 11372-11380 (2007).
11. C. Mussolino, et al. Gene Ther. 18, 637-645 (2011).
12. L. H. Vandenberghe, et al. Sci. Transl. Med. 3, 88ra54 (2011).
13. A. Auricchio, Hum. Gene Ther. 22, 1169-1170 (2011).
14. M. Natkunarajah, et al. Gene Ther. 15, 463-467 (2008).
15. B. Dong, et al. Mol. Ther. 18, 87-92 (2010).
16. Y. Lai, et al. Mol. Ther. 18, 75-79 (2010).
17. Z. Wu, et al. Mol. Ther. 18, 80-86 (2010).
18. Y. Wang, et al. Hum. Gene Ther. Methods 23, 225-233 (2012).
19. P. L. Hermonat, et al. FEBS Lett. 407, 78-84 (1997).
20. R. Allikmets, Nat. Genet. 17, 122 (1997).
21. J. M. Millan, et al. J. Ophthalmol. 2011, 417217 (2011).
22. T. Hasson, et al. Proc. Natl. Acad. Sci. USA 92, 9815-9819 (1995).
23. X. Liu, et al. Cell. Motif. Cytoskeleton 37, 240-252 (1997).
24. D. Gibbs, et al. Invest. Ophthalmol. Vis. Sci. 51, 1130-1135 (2010).
25. J. C. Grieger, et al. J. Virol. 79, 9933-9944 (2005).
26. J. Wu, et al. Hum. Gene Ther. 18, 171-182 (2007).
27. M. Allocca, et al. J. Clin. Invest. 118, 1955-1964 (2008).
28. P. E. Monahan, et al. Mol. Ther. 18, 1907-1916 (2010).
29. W. E. Grose, et al. PLoS One 7, e39233 (2012).
30. V. S. Lopes, et al. Gene Ther. (2013).
31. M. L. Hirsch, et al. Mol. Ther. 18, 6-8 (2010).
32. D. Duan, et al. J. Virol. 72, 8568-8577 (1998).
33. Z. Yan, et al. Proc. Natl. Acad. Sci. USA 97, 6716-6721 (2000).
34. D. Duan, et al. Mol. Ther. 4, 383-391 (2001).
35. A. Ghosh, et al. Mol. Ther. 16, 124-130 (2008).
36. Y. Lai, et al. Nat. Biotechnol. 23, 1435-1439 (2005).
37. S. J. Reich, et al. Hum. Gene. Ther. 14, 37-44 (2003).
38. A. Ghosh, et al. J. Gene Med. 8, 298-305 (2006).
39. A. Ghosh, et al. Hum. Gene Ther. 22, 77-83 (2011).
40. X. Dong, et al. PLoS One 5, e13479 (2010).
41. N. Esumi, et al. J. Biol. Chem. 279, 19064-19073 (2004).
42. L. Wu, et al. Adv. Exp. Med. Biol. 664, 533-539 (2010).
43. M. Illing, et al. J. Biol. Chem. 272, 10303-10310 (1997).
44. H. Sun, et al. Nat. Genet. 17, 15-16 (1997).
45. N. L. Mata, et al. Invest. Ophthalmol. Vis. Sci. 42, 1685-1690 (2001).
46. C. Lillo, et al. Adv. Exp. Med. Biol. 533, 143-150 (2003).
47. X. Liu, et al. Nat. Genet. 19, 117-118 (1998).
48. X. Liu, et al. J. Neurosci. 19, 6267-6274 (1999).
49. S. G. Jacobson, et al. Mol. Ther. 13, 1074-1084 (2006).
50. M. L. Fishel, et al. Mutat. Res. 614, 24-36 (2007).
51. Z. Yan, et al. J. Virol. 79, 364-379 (2005).
52. G. Gao, et al. Hum. Gene Ther. 11, 2079-2091 (2000).
53. A. Auricchio, et al. Hum. Gene Ther. 12, 71-76 (2001).
54. C. Mueller, et al. Curr. Protoc. Microbiol. Chapter 14, Unit 14D 11 (2012).
55. L. Drittanti, et al. Gene Ther. 7, 924-929 (2000).
56. Y. Zhang, et al. J. Virol. 74, 8003-8010 (2000).
57. R. A. Radu, et al. Proc. Natl. Acad. Sci. USA 101, 5928-5933 (2004).
58. V. E. Papaioannou, J. G. Fox, Lab. Anim. Sci. 43, 189-192 (1993).
59. F. Q. Liang, et al. in Methods in Molecular Medicine: Vision Research Protocols, P. E. Rakoczy, Ed. (Humana Press Inc, Totowa, N.J., 2000), vol. 47, pp. 125-139.
60. A. Gargiulo, et al. Mol. Ther. 17, 1347-1354 (2009).
61. V. N. Venables, B. D. Ripley, Modern Applied Statistics with S, S. J. Chambers, W. Eddy, W. Hardle, Sheater S, L. Tierney, Eds., (Springer Science+Business Media, New York, USA, 2002). [fourth edition].
Weng, J., et al. I Cell 98, 13-23 (1999).

SEQUENCE LISTING

```
<160> NUMBER OF SEQ ID NOS: 34

<210> SEQ ID NO 1
<211> LENGTH: 82
<212> TYPE: DNA
<213> ORGANISM: Artificial Sequence
<220> FEATURE:
<223> OTHER INFORMATION: synthetic

<400> SEQUENCE: 1

gtaagtatca aggttacaag acaggtttaa ggagaccaat agaaactggg cttgtcgaga     60

cagagaagac tcttgcgttt ct                                              82


<210> SEQ ID NO 2
<211> LENGTH: 51
<212> TYPE: DNA
<213> ORGANISM: Artificial Sequence
<220> FEATURE:
<223> OTHER INFORMATION: synthetic
```

<400> SEQUENCE: 2 gataggcacc tattggtctt actgacatcc actttgcctt tctctccaca g 51

<210> SEQ ID NO 3
<211> LENGTH: 77
<212> TYPE: DNA
<213> ORGANISM: Artificial Sequence
<220> FEATURE:
<223> OTHER INFORMATION: synthetic

<400> SEQUENCE: 3 gggattttgc cgatttcggc ctattggtta aaaaatgagc tgatttaaca aaaatttaac 60 gcgaatttta acaaaat 77

<210> SEQ ID NO 4
<211> LENGTH: 130
<212> TYPE: DNA
<213> ORGANISM: Artificial Sequence
<220> FEATURE:
<223> OTHER INFORMATION: synthetic

<400> SEQUENCE: 4 ctgcgcgctc gctcgctcac tgaggccgcc cgggcaaagc ccgggcgtcg ggcgaccttt 60 ggtcgcccgg cctcagtgag cgagcgagcg cgcagagagg gagtggccaa ctccatcact 120 aggggttcct 130

<210> SEQ ID NO 5
<211> LENGTH: 175
<212> TYPE: DNA
<213> ORGANISM: Artificial Sequence
<220> FEATURE:
<223> OTHER INFORMATION: synthetic

<400> SEQUENCE: 5 ctctcccccc tgtcgcgttc gctcgctcgc tggctcgttt gggggggtgg cagctcaaag 60 agctgccaga cgacggccct ctggccgtcg ccccccccaaa cgagccagcg agcgagcgaa 120 cgcgacaggg gggagagtgc cacactctca agcaaggggg ttttgtaagc agtga 175

<210> SEQ ID NO 6
<211> LENGTH: 153
<212> TYPE: DNA
<213> ORGANISM: Artificial Sequence
<220> FEATURE:
<223> OTHER INFORMATION: synthetic

<400> SEQUENCE: 6 tcaatattgg ccattagcca tattattcat tggttatata gcataaatca atattggcta 60 ttggccattg catacgttgt atctatatca taatatgtac atttatattg gctcatgtcc 120 aatatgaccg ccatgttggc attgattatt gac 153

<210> SEQ ID NO 7
<211> LENGTH: 583
<212> TYPE: DNA
<213> ORGANISM: Artificial Sequence
<220> FEATURE:
<223> OTHER INFORMATION: synthetic

<400> SEQUENCE: 7 tagttattaa tagtaatcaa ttacggggtc attagttcat agcccatata tggagttccg 60 cgttacataa cttacggtaa atggcccgcc tggctgaccg cccaacgacc cccgcccatt 120 gacgtcaata atgacgtatg ttcccatagt aacgccaata gggactttcc attgacgtca 180 atgggtggag tatttacggt aaactgccca cttggcagta catcaagtgt atcatatgcc 240 aagtccgccc cctattgacg tcaatgacgg taaatggccc gcctggcatt atgcccagta 300 catgacctta cgggactttc ctacttggca gtacatctac gtattagtca tcgctattac 360 catggtgatg cggttttggc agtacaccaa tgggcgtgga tagcggtttg actcacgggg 420 atttccaagt ctccacccca ttgacgtcaa tgggagtttg ttttggcacc aaaatcaacg 480 ggactttcca aaatgtcgta ataaccccgc cccgttgacg caaatgggcg gtaggcgtgt 540 acggtgggag gtctatataa gcagagctcg tttagtgaac cgt 583

<210> SEQ ID NO 8
<211> LENGTH: 133
<212> TYPE: DNA
<213> ORGANISM: Artificial Sequence
<220> FEATURE:
<223> OTHER INFORMATION: synthetic

<400> SEQUENCE: 8 gtaagtatca aggttacaag acaggtttaa ggagaccaat agaaactggg cttgtcgaga 60 cagagaagac tcttgcgttt ctgataggca cctattggtc ttactgacat ccactttgcc 120 tttctctcca cag 133

<210> SEQ ID NO 9
<211> LENGTH: 2918
<212> TYPE: DNA
<213> ORGANISM: Artificial Sequence
<220> FEATURE:
<223> OTHER INFORMATION: synthetic

<400> SEQUENCE: 9 atgggcttcg tgagacagat acagcttttg ctctggaaga actggaccct gcggaaaagg 60 caaaagattc gctttgtggt ggaactcgtg tggcctttat ctttatttct ggtcttgatc 120 tggttaagga atgccaaccc gctctacagc catcatgaat gccatttccc caacaaggcg 180 atgccctcag caggaatgct gccgtggctc caggggatct tctgcaatgt gaacaatccc 240 tgttttcaaa gccccacccc aggagaatct cctggaattg tgtcaaacta taacaactcc 300 atcttggcaa gggtatatcg agattttcaa gaactcctca tgaatgcacc agagagccag 360 caccttggcc gtatttggac agagctacac atcttgtccc aattcatgga caccctccgg 420 actcacccgg agagaattgc aggaagagga attcgaataa gggatatctt gaaagatgaa 480 gaaacactga cactatttct cattaaaaac atcggcctgt ctgactcagt ggtctacctt 540 ctgatcaact ctcaagtccg tccagagcag ttcgctcatg gagtcccgga cctggcgctg 600 aaggacatcg cctgcagcga ggccctcctg gagcgcttca tcatcttcag ccagagacgc 660 ggggcaaaga cggtgcgcta tgccctgtgc tccctctccc agggcaccct acagtggata 720 gaagacactc tgtatgccaa cgtggacttc ttcaagctct tccgtgtgct tcccacactc 780 ctagacagcc gttctcaagg tatcaatctg agatcttggg gaggaatatt atctgatatg 840 tcaccaagaa ttcaagagtt tatccatcgg ccgagtatgc aggacttgct gtgggtgacc 900 aggcccctca tgcagaatgg tggtccagag acctttacaa agctgatggg catcctgtct 960 gacctcctgt gtggctaccc cgagggaggt ggctctcggg tgctctcctt caactggtat 1020 gaagacaata actataaggc ctttctgggg attgactcca caaggaagga tcctatctat 1080 tcttatgaca gaagaacaac atccttttgt aatgcattga tccagagcct ggagtcaaat 1140 cctttaacca aaatcgcttg gagggcggca aagcctttgc tgatgggaaa aatcctgtac 1200 actcctgatt cacctgcagc acgaaggata ctgaagaatg ccaactcaac ttttgaagaa 1260 ctggaacacg ttaggaagtt ggtcaaagcc tgggaagaag tagggcccca gatctggtac 1320 ttctttgaca acagcacaca gatgaacatg atcagagata ccctggggaa cccaacagta 1380 aaagactttt tgaataggca gcttggtgaa gaaggtatta ctgctgaagc catcctaaac 1440 ttcctctaca agggccctcg ggaaagccag gctgacgaca tggccaactt cgactggagg 1500 gacatattta acatcactga tcgcaccctc cgccttgtca atcaatacct ggagtgcttg 1560 gtcctggata agtttgaaag ctacaatgat gaaactcagc tcacccaacg tgccctctct 1620 ctactggagg aaaacatgtt ctgggccgga gtggtattcc ctgacatgta tccctggacc 1680 agctctctac caccccacgt gaagtataag atccgaatgg acatagacgt ggtggagaaa 1740 accaataaga ttaaagacag gtattgggat tctggtccca gagctgatcc cgtggaagat 1800 ttccggtaca tctggggcgg gtttgcctat ctgcaggaca tggttgaaca ggggatcaca 1860 aggagccagg tgcaggcgga ggctccagtt ggaatctacc tccagcagat gccctacccc 1920 tgcttcgtgg acgattcttt catgatcatc ctgaaccgct gtttccctat cttcatggtg 1980 ctggcatgga tctactctgt ctccatgact gtgaagagca tcgtcttgga gaaggagttg 2040 cgactgaagg agaccttgaa aaatcagggt gtctccaatg cagtgatttg gtgtacctgg 2100 ttcctggaca gcttctccat catgtcgatg agcatcttcc tcctgacgat attcatcatg 2160 catggaagaa tcctacatta cagcgaccca ttcatcctct tcctgttctt gttggctttc 2220 tccactgcca ccatcatgct gtgctttctg ctcagcacct tcttctccaa ggccagtctg 2280 gcagcagcct gtagtggtgt catctatttc accctctacc tgccacacat cctgtgcttc 2340 gcctggcagg accgcatgac cgctgagctg aagaaggctg tgagcttact gtctccggtg 2400 gcatttggat ttggcactga gtacctggtt cgctttgaag agcaaggcct ggggctgcag 2460 tggagcaaca tcgggaacag tcccacggaa ggggacgaat tcagcttcct gctgtccatg 2520 cagatgatgc tccttgatgc tgctgtctat ggcttactcg cttggtacct tgatcaggtg 2580 tttccaggag actatggaac cccacttcct tggtactttc ttctacaaga gtcgtattgg 2640 cttggcggtg aagggtgttc aaccagagaa gaaagagccc tggaaaagac cgagccccta 2700 acagaggaaa cggaggatcc agagcaccca gaaggaatac acgactcctt ctttgaacgt 2760 gagcatccag ggtgggttcc tggggtatgc gtgaagaatc tggtaaagat ttttgagccc 2820 tgtggccggc cagctgtgga ccgtctgaac atcaccttct acgagaacca gatcaccgca 2880 ttcctgggcc acaatggagc tgggaaaacc accacctt 2918

<210> SEQ ID NO 10
<211> LENGTH: 130
<212> TYPE: DNA
<213> ORGANISM: Artificial Sequence
<220> FEATURE:
<223> OTHER INFORMATION: synthetic

<400> SEQUENCE: 10 aggaacccct agtgatggag ttggccactc cctctctgcg cgctcgctcg ctcactgagg 60 ccgggcgacc aaaggtcgcc cgacgcccgg gctttgcccg ggcggcctca gtgagcgagc 120 gagcgcgcag 130

<210> SEQ ID NO 11
<211> LENGTH: 4540
<212> TYPE: DNA
<213> ORGANISM: Artificial Sequence
<220> FEATURE:
<223> OTHER INFORMATION: synthetic

<400> SEQUENCE: 11 ctgcgcgctc gctcgctcac tgaggccgcc cgggcaaagc ccgggcgtcg ggcgaccttt 60 ggtcgcccgg cctcagtgag cgagcgagcg cgcagagagg gagtggccaa ctccatcact 120 aggggttcct tgtagttaat gattaacccg ccatgctact tatctacgta gccatgctct 180 aggaagatct tcaatattgg ccattagcca tattattcat tggttatata gcataaatca 240 atattggcta ttggccattg catacgttgt atctatatca taatatgtac atttatattg 300 gctcatgtcc aatatgaccg ccatgttggc attgattatt gactagttat taatagtaat 360 caattacggg gtcattagtt catagcccat atatggagtt ccgcgttaca taacttacgg 420 taaatggccc gcctggctga ccgcccaacg acccccgccc attgacgtca ataatgacgt 480 atgttcccat agtaacgcca atagggactt tccattgacg tcaatgggtg gagtatttac 540 ggtaaactgc ccacttggca gtacatcaag tgtatcatat gccaagtccg ccccctattg 600 acgtcaatga cggtaaatgg cccgcctggc attatgccca gtacatgacc ttacgggact 660 ttcctacttg gcagtacatc tacgtattag tcatcgctat taccatggtg atgcggtttt 720 ggcagtacac caatgggcgt ggatagcggt ttgactcacg gggatttcca agtctccacc 780 ccattgacgt caatgggagt ttgttttggc accaaaatca acgggacttt ccaaaatgtc 840 gtaataaccc cgccccgttg acgcaaatgg gcggtaggcg tgtacggtgg gaggtctata 900 taagcagagc tcgtttagtg aaccgtcaga tcactagaag ctttattgcg gtagtttatc 960 acagttaaat tgctaacgca gtcagtgctt ctgacacaac agtctcgaac ttaagctgca 1020 gaagttggtc gtgaggcact gggcaggtaa gtatcaaggt tacaagacag gtttaaggag 1080 accaatagaa actgggcttg tcgagacaga gaagactctt gcgtttctga taggcaccta 1140 ttggtcttac tgacatccac tttgcctttc tctccacagg tgtccactcc cagttcaatt 1200 acagctctta aggctagagt acttaatacg actcactata ggctagcctc gagaattcac 1260 gcgtggtacc tctagagtcg acccgggcgg ccgccatggg cttcgtgaga cagatacagc 1320 ttttgctctg gaagaactgg accctgcgga aaaggcaaaa gattcgcttt gtggtggaac 1380 tcgtgtggcc tttatcttta tttctggtct tgatctggtt aaggaatgcc aacccgctct 1440 acagccatca tgaatgccat ttccccaaca aggcgatgcc ctcagcagga atgctgccgt 1500 ggctccaggg gatcttctgc aatgtgaaca atccctgttt tcaaagcccc accccaggag 1560 aatctcctgg aattgtgtca aactataaca actccatctt ggcaagggta tatcgagatt 1620 ttcaagaact cctcatgaat gcaccagaga gccagcacct tggccgtatt tggacagagc 1680 tacacatctt gtcccaattc atggacaccc tccggactca cccggagaga attgcaggaa 1740 gaggaattcg aataagggat atcttgaaag atgaagaaac actgacacta tttctcatta 1800 aaaacatcgg cctgtctgac tcagtggtct accttctgat caactctcaa gtccgtccag 1860 agcagttcgc tcatggagtc ccggacctgg cgctgaagga catcgcctgc agcgaggccc 1920 tcctggagcg cttcatcatc ttcagccaga gacgcggggc aaagacggtg cgctatgccc 1980 tgtgctccct ctcccagggc accctacagt ggatagaaga cactctgtat gccaacgtgg 2040 acttcttcaa gctcttccgt gtgcttccca cactcctaga cagccgttct caaggtatca 2100

-continued

```
atctgagatc ttggggagga atattatctg atatgtcacc aagaattcaa gagtttatcc   2160
atcggccgag tatgcaggac ttgctgtggg tgaccaggcc cctcatgcag aatggtggtc   2220
cagagacctt tacaaagctg atgggcatcc tgtctgacct cctgtgtggc taccccgagg   2280
gaggtggctc tcgggtgctc tccttcaact ggtatgaaga caataactat aaggcctttc   2340
tggggattga ctccacaagg aaggatccta tctattctta tgacagaaga acaacatcct   2400
tttgtaatgc attgatccag agcctggagt caaatccttt aaccaaaatc gcttggaggg   2460
cggcaaagcc tttgctgatg ggaaaaatcc tgtacactcc tgattcacct gcagcacgaa   2520
ggatactgaa gaatgccaac tcaacttttg aagaactgga acacgttagg aagttggtca   2580
aagcctggga agaagtaggg ccccagatct ggtacttctt tgacaacagc acacagatga   2640
acatgatcag agataccctg gggaacccaa cagtaaaaga ctttttgaat aggcagcttg   2700
gtgaagaagg tattactgct gaagccatcc taaacttcct ctacaagggc cctcgggaaa   2760
gccaggctga cgacatggcc aacttcgact ggagggacat atttaacatc actgatcgca   2820
ccctccgcct tgtcaatcaa tacctggagt gcttggtcct ggataagttt gaaagctaca   2880
atgatgaaac tcagctcacc caacgtgccc tctctctact ggaggaaaac atgttctggg   2940
ccggagtggt attccctgac atgtatccct ggaccagctc tctaccaccc cacgtgaagt   3000
ataagatccg aatggacata gacgtggtgg agaaaaccaa taagattaaa gacaggtatt   3060
gggattctgg tcccagagct gatcccgtgg aagatttccg gtacatctgg ggcgggtttg   3120
cctatctgca ggacatggtt gaacagggga tcacaaggag ccaggtgcag gcggaggctc   3180
cagttggaat ctacctccag cagatgccct acccctgctt cgtggacgat tctttcatga   3240
tcatcctgaa ccgctgtttc cctatcttca tggtgctggc atggatctac tctgtctcca   3300
tgactgtgaa gagcatcgtc ttggagaagg agttgcgact gaaggagacc ttgaaaaatc   3360
agggtgtctc caatgcagtg atttggtgta cctggttcct ggacagcttc tccatcatgt   3420
cgatgagcat cttcctcctg acgatattca tcatgcatgg aagaatccta cattacagcg   3480
acccattcat cctcttcctg ttcttgttgg ctttctccac tgccaccatc atgctgtgct   3540
ttctgctcag caccttcttc tccaaggcca gtctggcagc agcctgtagt ggtgtcatct   3600
atttcaccct ctacctgcca cacatcctgt gcttcgcctg gcaggaccgc atgaccgctg   3660
agctgaagaa ggctgtgagc ttactgtctc cggtggcatt tggatttggc actgagtacc   3720
tggttcgctt tgaagagcaa ggcctggggc tgcagtggag caacatcggg aacagtccca   3780
cggaagggga cgaattcagc ttcctgctgt ccatgcagat gatgctcctt gatgctgctg   3840
tctatggctt actcgcttgg taccttgatc aggtgtttcc aggagactat ggaaccccac   3900
ttccttggta ctttcttcta caagagtcgt attggcttgg cggtgaaggg tgttcaacca   3960
gagaagaaag agccctggaa aagaccgagc ccctaacaga ggaaacggag gatccagagc   4020
acccagaagg aatacacgac tccttctttg aacgtgagca tccagggtgg gttcctgggg   4080
tatgcgtgaa gaatctggta aagatttttg agccctgtgg ccggccagct gtggaccgtc   4140
tgaacatcac cttctacgag aaccagatca ccgcattcct gggccacaat ggagctggga   4200
aaaccaccac cttgtaagta tcaaggttac aagacaggtt taaggagacc aatagaaact   4260
gggcttgtcg agacagagaa gactcttgcg tttctgggat tttgccgatt tcggcctatt   4320
ggttaaaaaa tgagctgatt taacaaaaat ttaacgcgaa ttttaacaaa atattaacgt   4380
ttataatttc aggtggcatc tttccaattg aggaacccct agtgatggag ttggccactc   4440
cctctctgcg cgctcgctcg ctcactgagg ccgggcgacc aaaggtcgcc cgacgcccgg   4500
```

gctttgcccg ggcggcctca gtgagcgagc gagcgcgcag 4540

<210> SEQ ID NO 12
<211> LENGTH: 3978
<212> TYPE: DNA
<213> ORGANISM: Artificial Sequence
<220> FEATURE:
<223> OTHER INFORMATION: synthetic

<400> SEQUENCE: 12 gtccatcctg acgggtctgt tgccaccaac ctctgggact gtgctcgttg ggggaaggga 60 cattgaaacc agcctggatg cagtccggca gagccttggc atgtgtccac agcacaacat 120 cctgttccac cacctcacgg tggctgagca catgctgttc tatgcccagc tgaaaggaaa 180 gtcccaggag gaggcccagc tggagatgga agccatgttg gaggacacag gcctccacca 240 caagcggaat gaagaggctc aggacctatc aggtggcatg cagagaaagc tgtcggttgc 300 cattgccttt gtgggagatg ccaaggtggt gattctggac gaacccacct ctggggtgga 360 cccttactcg agacgctcaa tctgggatct gctcctgaag tatcgctcag gcagaaccat 420 catcatgtcc actcaccaca tggacgaggc cgacctcctt ggggaccgca ttgccatcat 480 tgcccaggga aggctctact gctcaggcac cccactcttc ctgaagaact gctttggcac 540 aggcttgtac ttaaccttgg tgcgcaagat gaaaaacatc cagagccaaa ggaaaggcag 600 tgaggggacc tgcagctgct cgtctaaggg tttctccacc acgtgtccag cccacgtcga 660 tgacctaact ccagaacaag tcctggatgg ggatgtaaat gagctgatgg atgtagttct 720 ccaccatgtt ccagaggcaa agctggtgga gtgcattggt caagaactta tcttccttct 780 tccaaataag aacttcaagc acagagcata tgccagcctt ttcagagagc tggaggagac 840 gctggctgac cttggtctca gcagttttgg aatttctgac actcccctgg aagagatttt 900 tctgaaggtc acggaggatt ctgattcagg acctctgttt gcgggtggcg ctcagcagaa 960 aagagaaaac gtcaaccccc gacacccctg cttgggtccc agagagaagg ctggacagac 1020 accccaggac tccaatgtct gctccccagg ggcgccggct gctcacccag agggccagcc 1080 tcccccagag ccagagtgcc caggcccgca gctcaacacg gggacacagc tggtcctcca 1140 gcatgtgcag gcgctgctgg tcaagagatt ccaacacacc atccgcagcc acaaggactt 1200 cctggcgcag atcgtgctcc cggctacctt tgtgtttttg gctctgatgc tttctattgt 1260 tatccctcct tttggcgaat accccgcttt gacccttcac ccctggatat atgggcagca 1320 gtacaccttc ttcagcatgg atgaaccagg cagtgagcag ttcacggtac ttgcagacgt 1380 cctcctgaat aagccaggct ttggcaaccg ctgcctgaag gaagggtggc ttccggagta 1440 cccctgtggc aactcaacac cctggaagac tccttctgtg tccccaaaca tcacccagct 1500 gttccagaag cagaaatgga cacaggtcaa cccttcacca tcctgcaggt gcagcaccag 1560 ggagaagctc accatgctgc cagagtgccc cgagggtgcc gggggcctcc cgcccccccca 1620 gagaacacag cgcagcacgg aaattctaca agacctgacg gacaggaaca tctccgactt 1680 cttggtaaaa acgtatcctg ctcttataag aagcagctta aagagcaaat tctgggtcaa 1740 tgaacagagg tatggaggaa tttccattgg aggaaagctc ccagtcgtcc ccatcacggg 1800 ggaagcactt gttgggtttt taagcgacct tggccggatc atgaatgtga gcgggggccc 1860 tatcactaga gaggcctcta aagaaatacc tgatttcctt aaacatctag aaactgaaga 1920 caacattaag gtgtggttta ataacaaagg ctggcatgcc ctggtcagct ttctcaatgt 1980

```
ggcccacaac gccatcttac gggccagcct gcctaaggac agaagccccg aggagtatgg   2040
aatcaccgtc attagccaac ccctgaacct gaccaaggag cagctctcag agattacagt   2100
gctgaccact tcagtggatg ctgtggttgc catctgcgtg attttctcca tgtccttcgt   2160
cccagccagc tttgtccttt atttgatcca ggagcgggtg aacaaatcca agcacctcca   2220
gtttatcagt ggagtgagcc ccaccaccta ctgggtaacc aacttcctct gggacatcat   2280
gaattattcc gtgagtgctg ggctggtggt gggcatcttc atcgggtttc agaagaaagc   2340
ctacacttct ccagaaaacc ttcctgccct tgtggcactg ctcctgctgt atggatgggc   2400
ggtcattccc atgatgtacc cagcatcctt cctgtttgat gtccccagca cagcctatgt   2460
ggctttatct tgtgctaatc tgttcatcgg catcaacagc agtgctatta ccttcatctt   2520
ggaattattt gagaataacc ggacgctgct caggttcaac gccgtgctga ggaagctgct   2580
cattgtcttc ccccacttct gcctgggccg gggcctcatt gaccttgcac tgagccaggc   2640
tgtgacagat gtctatgccc ggtttggtga ggagcactct gcaaatccgt tccactggga   2700
cctgattggg aagaacctgt ttgccatggt ggtggaaggg gtggtgtact tcctcctgac   2760
cctgctggtc cagcgccact tcttcctctc ccaatggatt gccgagccca ctaaggagcc   2820
cattgttgat gaagatgatg atgtggctga agaaagacaa agaattatta ctggtggaaa   2880
taaaactgac atcttaaggc tacatgaact aaccaagatt tatccaggca cctccagccc   2940
agcagtggac aggctgtgtg tcggagttcg ccctggagag tgctttggcc tcctgggagt   3000
gaatggtgcc ggcaaaacaa ccacattcaa gatgctcact ggggacacca cagtgacctc   3060
aggggatgcc accgtagcag gcaagagtat tttaaccaat atttctgaag tccatcaaaa   3120
tatgggctac tgtcctcagt ttgatgcaat cgatgagctg ctcacaggac gagaacatct   3180
ttacctttat gcccggcttc gaggtgtacc agcagaagaa atcgaaaagg ttgcaaactg   3240
gagtattaag agcctgggcc tgactgtcta cgccgactgc ctggctggca cgtacagtgg   3300
gggcaacaag cggaaactct ccacagccat cgcactcatt ggctgcccac cgctggtgct   3360
gctggatgag cccaccacag ggatggaccc ccaggcacgc cgcatgctgt ggaacgtcat   3420
cgtgagcatc atcagagaag ggagggctgt ggtcctcaca tcccacagca tggaagaatg   3480
tgaggcactg tgtacccggc tggccatcat ggtaaagggc gcctttcgat gtatgggcac   3540
cattcagcat ctcaagtcca aatttggaga tggctatatc gtcacaatga agatcaaatc   3600
cccgaaggac gacctgcttc ctgacctgaa ccctgtggag cagttcttcc aggggaactt   3660
cccaggcagt gtgcagaggg agaggcacta caacatgctc cagttccagg tctcctcctc   3720
ctccctggcg aggatcttcc agctcctcct ctcccacaag gacagcctgc tcatcgagga   3780
gtactcagtc acacagacca cactggacca ggtgtttgta aattttgcta aacagcagac   3840
tgaaagtcat gacctccctc tgcaccctcg agctgctgga gccagtcgac aagcccagga   3900
cgactacaaa gaccatgacg gtgattataa agatcatgac atcgactaca aggatgacga   3960
tgacaagtga gcggccgc                                                 3978
```

<210> SEQ ID NO 13
<211> LENGTH: 261
<212> TYPE: DNA
<213> ORGANISM: Artificial Sequence
<220> FEATURE:
<223> OTHER INFORMATION: synthetic

<400> SEQUENCE: 13

```
ttcgagcaga catgataaga tacattgatg agtttggaca aaccacaact agaatgcagt     60
```

gaaaaaaatg ctttatttgt gaaatttgtg atgctattgc tttatttgta accattataa 120 gctgcaataa acaagttaac aacaacaatt gcattcattt tatgtttcag gttcaggggg 180 agatgtggga ggtttttaa agcaagtaaa acctctacaa atgtggtaaa atcgataagg 240 atcttcctag agcatggcta c 261

<210> SEQ ID NO 14
<211> LENGTH: 175
<212> TYPE: DNA
<213> ORGANISM: Artificial Sequence
<220> FEATURE:
<223> OTHER INFORMATION: synthetic

<400> SEQUENCE: 14 tcactgctta caaaaccccc ttgcttgaga gtgtggcact ctcccccctg tcgcgttcgc 60 tcgctcgctg gctcgtttgg gggggcgacg gccagagggc cgtcgtctgg cagctctttg 120 agctgccacc cccccaaacg agccagcgag cgagcgaacg cgacaggggg gagag 175

<210> SEQ ID NO 15
<211> LENGTH: 4636
<212> TYPE: DNA
<213> ORGANISM: Artificial Sequence
<220> FEATURE:
<223> OTHER INFORMATION: synthetic

<400> SEQUENCE: 15 ctgcgcgctc gctcgctcac tgaggccgcc cgggcaaagc ccgggcgtcg ggcgaccttt 60 ggtcgcccgg cctcagtgag cgagcgagcg cgcagagagg gagtggccaa ctccatcact 120 aggggttcct ggatccggga ttttgccgat ttcggcctat tggttaaaaa atgagctgat 180 ttaacaaaaa tttaacgcga attttaacaa aatattaacg tttataattt caggtggcat 240 ctttcgatag gcacctattg gtcttactga catccacttt gcctttctct ccacaggtcc 300 atcctgacgg gtctgttgcc accaacctct gggactgtgc tcgttggggg aagggacatt 360 gaaaccagcc tggatgcagt ccggcagagc cttggcatgt gtccacagca caacatcctg 420 ttccaccacc tcacggtggc tgagcacatg ctgttctatg cccagctgaa aggaaagtcc 480 caggaggagg cccagctgga gatggaagcc atgttggagg acacaggcct ccaccacaag 540 cggaatgaag aggctcagga cctatcaggt ggcatgcaga gaaagctgtc ggttgccatt 600 gcctttgtgg gagatgccaa ggtggtgatt ctggacgaac ccacctctgg ggtggaccct 660 tactcgagac gctcaatctg ggatctgctc ctgaagtatc gctcaggcag aaccatcatc 720 atgtccactc accacatgga cgaggccgac ctccttgggg accgcattgc catcattgcc 780 cagggaaggc tctactgctc aggcacccca ctcttcctga agaactgctt tggcacaggc 840 ttgtacttaa ccttggtgcg caagatgaaa aacatccaga gccaaaggaa aggcagtgag 900 gggacctgca gctgctcgtc taagggtttc tccaccacgt gtccagccca cgtcgatgac 960 ctaactccag aacaagtcct ggatggggat gtaaatgagc tgatggatgt agttctccac 1020 catgttccag aggcaaagct ggtggagtgc attggtcaag aacttatctt ccttcttcca 1080 aataagaact tcaagcacag agcatatgcc agccttttca gagagctgga ggagacgctg 1140 gctgaccttg gtctcagcag ttttggaatt tctgacactc ccctggaaga gatttttctg 1200 aaggtcacgg aggattctga ttcaggacct ctgtttgcgg gtggcgctca gcagaaaaga 1260 gaaaacgtca acccccgaca cccctgcttg ggtcccagag agaaggctgg acagacaccc 1320

-continued

```
caggactcca atgtctgctc cccaggggcg ccggctgctc acccagaggg ccagcctccc   1380
ccagagccag agtgcccagg cccgcagctc aacacgggga cacagctggt cctccagcat   1440
gtgcaggcgc tgctggtcaa gagattccaa cacaccatcc gcagccacaa ggacttcctg   1500
gcgcagatcg tgctcccggc tacctttgtg tttttggctc tgatgctttc tattgttatc   1560
cctccttttg gcgaataccc cgctttgacc cttcacccct ggatatatgg gcagcagtac   1620
accttcttca gcatggatga accaggcagt gagcagttca cggtacttgc agacgtcctc   1680
ctgaataagc caggctttgg caaccgctgc ctgaaggaag ggtggcttcc ggagtacccc   1740
tgtggcaact caacaccctg gaagactcct tctgtgtccc caaacatcac ccagctgttc   1800
cagaagcaga aatggacaca ggtcaaccct tcaccatcct gcaggtgcag caccagggag   1860
aagctcacca tgctgccaga gtgccccgag ggtgccgggg gcctcccgcc cccccagaga   1920
acacagcgca gcacggaaat tctacaagac ctgacggaca ggaacatctc cgacttcttg   1980
gtaaaaacgt atcctgctct tataagaagc agcttaaaga gcaaattctg ggtcaatgaa   2040
cagaggtatg gaggaatttc cattggagga aagctcccag tcgtccccat cacgggggaa   2100
gcacttgttg ggtttttaag cgaccttggc cggatcatga atgtgagcgg gggccctatc   2160
actagagagg cctctaaaga aatacctgat ttccttaaac atctagaaac tgaagacaac   2220
attaaggtgt ggtttaataa caaaggctgg catgccctgg tcagctttct caatgtggcc   2280
cacaacgcca tcttacgggc cagcctgcct aaggacagaa gccccgagga gtatggaatc   2340
accgtcatta gccaacccct gaacctgacc aaggagcagc tctcagagat tacagtgctg   2400
accacttcag tggatgctgt ggttgccatc tgcgtgattt tctccatgtc cttcgtccca   2460
gccagctttg tcctttattt gatccaggag cgggtgaaca aatccaagca cctccagttt   2520
atcagtggag tgagccccac cacctactgg gtaaccaact tcctctggga catcatgaat   2580
tattccgtga gtgctgggct ggtggtgggc atcttcatcg ggtttcagaa gaaagcctac   2640
acttctccag aaaaccttcc tgcccttgtg gcactgctcc tgctgtatgg atgggcggtc   2700
attcccatga tgtacccagc atccttcctg tttgatgtcc ccagcacagc ctatgtggct   2760
ttatcttgtg ctaatctgtt catcggcatc aacagcagtg ctattacctt catcttggaa   2820
ttatttgaga ataaccggac gctgctcagg ttcaacgccg tgctgaggaa gctgctcatt   2880
gtcttccccc acttctgcct gggccggggc ctcattgacc ttgcactgag ccaggctgtg   2940
acagatgtct atgcccggtt tggtgaggag cactctgcaa atccgttcca ctgggacctg   3000
attgggaaga acctgtttgc catggtggtg gaaggggtgg tgtacttcct cctgaccctg   3060
ctggtccagc gccacttctt cctctcccaa tggattgccg agcccactaa ggagcccatt   3120
gttgatgaag atgatgatgt ggctgaagaa agacaaagaa ttattactgg tggaaataaa   3180
actgacatct taaggctaca tgaactaacc aagatttatc caggcacctc cagcccagca   3240
gtggacaggc tgtgtgtcgg agttcgccct ggagagtgct ttggcctcct gggagtgaat   3300
ggtgccggca aaacaaccac attcaagatg ctcactgggg acaccacagt gacctcaggg   3360
gatgccaccg tagcaggcaa gagtatttta accaatattt ctgaagtcca tcaaaatatg   3420
ggctactgtc ctcagtttga tgcaatcgat gagctgctca caggacgaga acatctttac   3480
ctttatgccc ggcttcgagg tgtaccagca gaagaaatcg aaaaggttgc aaactggagt   3540
attaagagcc tgggcctgac tgtctacgcc gactgcctgg ctggcacgta cagtgggggc   3600
aacaagcgga aactctccac agccatcgca ctcattggct gcccaccgct ggtgctgctg   3660
gatgagccca ccacagggat ggacccccag gcacgccgca tgctgtggaa cgtcatcgtg   3720
```

agcatcatca gagaagggag ggctgtggtc ctcacatccc acagcatgga agaatgtgag 3780 gcactgtgta cccggctggc catcatggta aagggcgcct ttcgatgtat gggcaccatt 3840 cagcatctca agtccaaatt tggagatggc tatatcgtca caatgaagat caaatccccg 3900 aaggacgacc tgcttcctga cctgaaccct gtggagcagt tcttccaggg gaacttccca 3960 ggcagtgtgc agagggagag gcactacaac atgctccagt tccaggtctc ctcctcctcc 4020 ctggcgagga tcttccagct cctcctctcc cacaaggaca gcctgctcat cgaggagtac 4080 tcagtcacac agaccacact ggaccaggtg tttgtaaatt ttgctaaaca gcagactgaa 4140 agtcatgacc tccctctgca ccctcgagct gctggagcca gtcgacaagc ccaggactga 4200 gcggccgctt cgagcagaca tgataagata cattgatgag tttggacaaa ccacaactag 4260 aatgcagtga aaaaaatgct ttatttgtga aatttgtgat gctattgctt tatttgtaac 4320 cattataagc tgcaataaac aagttaacaa caacaattgc attcatttta tgtttcaggt 4380 tcagggggag atgtgggagg ttttttaaag caagtaaaac ctctacaaat gtggtaaaat 4440 cgataaggat cttcctagag catggctacg tagataagta gcatggcggg ttaatcatta 4500 actacaagga acccctagtg atggagttgg ccactccctc tctgcgcgct cgctcgctca 4560 ctgaggccgg gcgaccaaag gtcgcccgac gcccgggctt tgcccgggcg gcctcagtga 4620 gcgagcgagc gcgcag 4636

<210> SEQ ID NO 16
<211> LENGTH: 4431
<212> TYPE: DNA
<213> ORGANISM: Artificial Sequence
<220> FEATURE:
<223> OTHER INFORMATION: synthetic

<400> SEQUENCE: 16 ctgcgcgctc gctcgctcac tgaggccgcc cgggcaaagc ccgggcgtcg ggcgaccttt 60 ggtcgcccgg cctcagtgag cgagcgagcg cgcagagagg gagtggccaa ctccatcact 120 aggggttcct tgtagttaat gattaacccg ccatgctact tatctacgta gccatgctct 180 aggaagatct tcaatattgg ccattagcca tattattcat tggttatata gcataaatca 240 atattggcta ttggccattg catacgttgt atctatatca taatatgtac atttatattg 300 gctcatgtcc aatatgaccg ccatgttggc attgattatt gactagttat taatagtaat 360 caattacggg gtcattagtt catagcccat atatggagtt ccgcgttaca taacttacgg 420 taaatggccc gcctggctga ccgcccaacg acccccgccc attgacgtca ataatgacgt 480 atgttcccat agtaacgcca atagggactt tccattgacg tcaatgggtg gagtatttac 540 ggtaaactgc ccacttggca gtacatcaag tgtatcatat gccaagtccg ccccctattg 600 acgtcaatga cggtaaatgg cccgcctggc attatgccca gtacatgacc ttacgggact 660 ttcctacttg gcagtacatc tacgtattag tcatcgctat taccatggtg atgcggtttt 720 ggcagtacac caatgggcgt ggatagcggt ttgactcacg gggatttcca agtctccacc 780 ccattgacgt caatgggagt ttgttttggc accaaaatca acgggacttt ccaaaatgtc 840 gtaataaccc cgccccgttg acgcaaatgg gcggtaggcg tgtacggtgg gaggtctata 900 taagcagagc tcgtttagtg aaccgtcaga tcactagaag ctttattgcg gtagtttatc 960 acagttaaat tgctaacgca gtcagtgctt ctgacacaac agtctcgaac ttaagctgca 1020 gaagttggtc gtgaggcact gggcaggtaa gtatcaaggt tacaagacag gtttaaggag 1080

```
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcctc gagaattcac   1260
gcgtggtacc tctagagtcg acccgggcgg ccgccatggg cttcgtgaga cagatacagc   1320
ttttgctctg gaagaactgg accctgcgga aaaggcaaaa gattcgcttt gtggtggaac   1380
tcgtgtggcc tttatcttta tttctggtct tgatctggtt aaggaatgcc aacccgctct   1440
acagccatca tgaatgccat ttccccaaca aggcgatgcc ctcagcagga atgctgccgt   1500
ggctccaggg gatcttctgc aatgtgaaca atccctgttt tcaaagcccc accccaggag   1560
aatctcctgg aattgtgtca aactataaca actccatctt ggcaagggta tatcgagatt   1620
ttcaagaact cctcatgaat gcaccagaga gccagcacct tggccgtatt tggacagagc   1680
tacacatctt gtcccaattc atggacaccc tccggactca cccggagaga attgcaggaa   1740
gaggaattcg aataagggat atcttgaaag atgaagaaac actgacacta tttctcatta   1800
aaaacatcgg cctgtctgac tcagtggtct accttctgat caactctcaa gtccgtccag   1860
agcagttcgc tcatggagtc ccggacctgg cgctgaagga catcgcctgc agcgaggccc   1920
tcctggagcg cttcatcatc ttcagccaga gacgcggggc aaagacggtg cgctatgccc   1980
tgtgctccct ctcccagggc accctacagt ggatagaaga cactctgtat gccaacgtgg   2040
acttcttcaa gctcttccgt gtgcttccca cactcctaga cagccgttct caaggtatca   2100
atctgagatc ttggggagga atattatctg atatgtcacc aagaattcaa gagtttatcc   2160
atcggccgag tatgcaggac ttgctgtggg tgaccaggcc cctcatgcag aatggtggtc   2220
cagagacctt tacaaagctg atgggcatcc tgtctgacct cctgtgtggc taccccgagg   2280
gaggtggctc tcgggtgctc tccttcaact ggtatgaaga caataactat aaggcctttc   2340
tggggattga ctccacaagg aaggatccta tctattctta tgacagaaga acaacatcct   2400
tttgtaatgc attgatccag agcctggagt caaatccttt aaccaaaatc gcttggaggg   2460
cggcaaagcc tttgctgatg ggaaaaatcc tgtacactcc tgattcacct gcagcacgaa   2520
ggatactgaa gaatgccaac tcaacttttg aagaactgga acacgttagg aagttggtca   2580
aagcctggga agaagtaggg ccccagatct ggtacttctt tgacaacagc acacagatga   2640
acatgatcag agataccctg gggaacccaa cagtaaaaga ctttttgaat aggcagcttg   2700
gtgaagaagg tattactgct gaagccatcc taaacttcct ctacaagggc cctcgggaaa   2760
gccaggctga cgacatggcc aacttcgact ggagggacat atttaacatc actgatcgca   2820
ccctccgcct tgtcaatcaa tacctggagt gcttggtcct ggataagttt gaaagctaca   2880
atgatgaaac tcagctcacc caacgtgccc tctctctact ggaggaaaac atgttctggg   2940
ccggagtggt attccctgac atgtatccct ggaccagctc tctaccaccc cacgtgaagt   3000
ataagatccg aatggacata gacgtggtgg agaaaaccaa taagattaaa gacaggtatt   3060
gggattctgg tcccagagct gatcccgtgg aagatttccg gtacatctgg ggcgggtttg   3120
cctatctgca ggacatggtt gaacagggga tcacaaggag ccaggtgcag gcggaggctc   3180
cagttggaat ctacctccag cagatgccct acccctgctt cgtggacgat tctttcatga   3240
tcatcctgaa ccgctgtttc cctatcttca tggtgctggc atggatctac tctgtctcca   3300
tgactgtgaa gagcatcgtc ttggagaagg agttgcgact gaaggagacc ttgaaaaatc   3360
agggtgtctc caatgcagtg atttggtgta cctggttcct ggacagcttc tccatcatgt   3420
cgatgagcat cttcctcctg acgatattca tcatgcatgg aagaatccta cattacagcg   3480
```

```
acccattcat cctcttcctg ttcttgttgg ctttctccac tgccaccatc atgctgtgct   3540

ttctgctcag caccttcttc tccaaggcca gtctggcagc agcctgtagt ggtgtcatct   3600

atttcaccct ctacctgcca cacatcctgt gcttcgcctg gcaggaccgc atgaccgctg   3660

agctgaagaa ggctgtgagc ttactgtctc cggtggcatt tggatttggc actgagtacc   3720

tggttcgctt tgaagagcaa ggcctggggc tgcagtggag caacatcggg aacagtccca   3780

cggaagggga cgaattcagc ttcctgctgt ccatgcagat gatgctcctt gatgctgctg   3840

tctatggctt actcgcttgg taccttgatc aggtgtttcc aggagactat ggaaccccac   3900

ttccttggta ctttcttcta caagagtcgt attggcttgg cggtgaaggg tgttcaacca   3960

gagaagaaag agccctggaa aagaccgagc ccctaacaga ggaaacggag gatccagagc   4020

acccagaagg aatacacgac tccttctttg aacgtgagca tccagggtgg gttcctgggg   4080

tatgcgtgaa gaatctggta aagatttttg agccctgtgg ccggccagct gtggaccgtc   4140

tgaacatcac cttctacgag aaccagatca ccgcattcct gggccacaat ggagctggga   4200

aaaccaccac cttgtaagta tcaaggttac aagacaggtt taaggagacc aatagaaact   4260

gggcttgtcg agacagagaa gactcttgcg tttctcaatt gaggaacccc tagtgatgga   4320

gttggccact ccctctctgc gcgctcgctc gctcactgag gccgggcgac caaaggtcgc   4380

ccgacgcccg ggctttgccc gggcggcctc agtgagcgag cgagcgcgca g            4431
```

<210> SEQ ID NO 17
<211> LENGTH: 4521
<212> TYPE: DNA
<213> ORGANISM: Artificial Sequence
<220> FEATURE:
<223> OTHER INFORMATION: synthetic

<400> SEQUENCE: 17

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct gataggcacc tattggtctt actgacatcc actttgcctt tctctccaca    180

ggtccatcct gacgggtctg ttgccaccaa cctctgggac tgtgctcgtt gggggaaggg    240

acattgaaac cagcctggat gcagtccggc agagccttgg catgtgtcca cagcacaaca    300

tcctgttcca ccacctcacg gtggctgagc acatgctgtt ctatgcccag ctgaaaggaa    360

agtcccagga ggaggcccag ctggagatgg aagccatgtt ggaggacaca ggcctccacc    420

acaagcggaa tgaagaggct caggacctat caggtggcat gcagagaaag ctgtcggttg    480

ccattgcctt tgtgggagat gccaaggtgg tgattctgga cgaacccacc tctggggtgg    540

acccttactc gagacgctca atctgggatc tgctcctgaa gtatcgctca ggcagaacca    600

tcatcatgtc cactcaccac atggacgagg ccgacctcct tggggaccgc attgccatca    660

ttgcccaggg aaggctctac tgctcaggca ccccactctt cctgaagaac tgctttggca    720

caggcttgta cttaaccttg gtgcgcaaga tgaaaaacat ccagagccaa aggaaaggca    780

gtgaggggac ctgcagctgc tcgtctaagg gtttctccac cacgtgtcca gcccacgtcg    840

atgacctaac tccagaacaa gtcctggatg gggatgtaaa tgagctgatg gatgtagttc    900

tccaccatgt tccagaggca aagctggtgg agtgcattgg tcaagaactt atcttccttc    960

ttccaaataa gaacttcaag cacagagcat atgccagcct tttcagagag ctggaggaga   1020

cgctggctga ccttggtctc agcagttttg gaatttctga cactcccctg gaagagattt   1080
```

-continued

```
ttctgaaggt cacggaggat tctgattcag gacctctgtt tgcgggtggc gctcagcaga   1140
aaagagaaaa cgtcaacccc cgacacccct gcttgggtcc cagagagaag gctggacaga   1200
caccccagga ctccaatgtc tgctccccag gggcgccggc tgctcaccca gagggccagc   1260
ctcccccaga gccagagtgc ccaggcccgc agctcaacac ggggacacag ctggtcctcc   1320
agcatgtgca ggcgctgctg gtcaagagat tccaacacac catccgcagc cacaaggact   1380
tcctggcgca gatcgtgctc ccggctacct ttgtgttttt ggctctgatg ctttctattg   1440
ttatccctcc ttttggcgaa taccccgctt tgacccttca cccctggata tatgggcagc   1500
agtacacctt cttcagcatg gatgaaccag gcagtgagca gttcacggta cttgcagacg   1560
tcctcctgaa taagccaggc tttggcaacc gctgcctgaa ggaagggtgg cttccggagt   1620
acccctgtgg caactcaaca ccctggaaga ctccttctgt gtccccaaac atcacccagc   1680
tgttccagaa gcagaaatgg acacaggtca acccttcacc atcctgcagg tgcagcacca   1740
gggagaagct caccatgctg ccagagtgcc ccgagggtgc cgggggcctc ccgccccccc   1800
agagaacaca gcgcagcacg gaaattctac aagacctgac ggacaggaac atctccgact   1860
tcttggtaaa aacgtatcct gctcttataa gaagcagctt aaagagcaaa ttctgggtca   1920
atgaacagag gtatggagga atttccattg gaggaaagct cccagtcgtc cccatcacgg   1980
gggaagcact tgttgggttt ttaagcgacc ttggccggat catgaatgtg agcgggggcc   2040
ctatcactag agaggcctct aaagaaatac ctgatttcct taaacatcta gaaactgaag   2100
acaacattaa ggtgtggttt aataacaaag gctggcatgc cctggtcagc tttctcaatg   2160
tggcccacaa cgccatctta cgggccagcc tgcctaagga cagaagcccc gaggagtatg   2220
gaatcaccgt cattagccaa cccctgaacc tgaccaagga gcagctctca gagattacag   2280
tgctgaccac ttcagtggat gctgtggttg ccatctgcgt gattttctcc atgtccttcg   2340
tcccagccag ctttgtcctt tatttgatcc aggagcgggt gaacaaatcc aagcacctcc   2400
agtttatcag tggagtgagc cccaccacct actgggtaac caacttcctc tgggacatca   2460
tgaattattc cgtgagtgct gggctggtgg tgggcatctt catcgggttt cagaagaaag   2520
cctacacttc tccagaaaac cttcctgccc ttgtggcact gctcctgctg tatggatggg   2580
cggtcattcc catgatgtac ccagcatcct tcctgtttga tgtccccagc acagcctatg   2640
tggctttatc ttgtgctaat ctgttcatcg gcatcaacag cagtgctatt accttcatct   2700
tggaattatt tgagaataac cggacgctgc tcaggttcaa cgccgtgctg aggaagctgc   2760
tcattgtctt cccccacttc tgcctgggcc ggggcctcat tgaccttgca ctgagccagg   2820
ctgtgacaga tgtctatgcc cggtttggtg aggagcactc tgcaaatccg ttccactggg   2880
acctgattgg gaagaacctg tttgccatgg tggtggaagg ggtggtgtac ttcctcctga   2940
ccctgctggt ccagcgccac ttcttcctct cccaatggat tgccgagccc actaaggagc   3000
ccattgttga tgaagatgat gatgtggctg aagaaagaca aagaattatt actggtggaa   3060
ataaaactga catcttaagg ctacatgaac taaccaagat ttatccaggc acctccagcc   3120
cagcagtgga caggctgtgt gtcggagttc gccctggaga gtgctttggc ctcctgggag   3180
tgaatggtgc cggcaaaaca accacattca agatgctcac tggggacacc acagtgacct   3240
caggggatgc caccgtagca ggcaagagta ttttaaccaa tatttctgaa gtccatcaaa   3300
atatgggcta ctgtcctcag tttgatgcaa tcgatgagct gctcacagga cgagaacatc   3360
tttaccttta tgcccggctt cgaggtgtac cagcagaaga aatcgaaaag gttgcaaact   3420
ggagtattaa gagcctgggc ctgactgtct acgccgactg cctggctggc acgtacagtg   3480
```

```
ggggcaacaa gcggaaactc tccacagcca tcgcactcat tggctgccca ccgctggtgc   3540

tgctggatga gcccaccaca gggatggacc cccaggcacg ccgcatgctg tggaacgtca   3600

tcgtgagcat catcagagaa gggagggctg tggtcctcac atcccacagc atggaagaat   3660

gtgaggcact gtgtacccgg ctggccatca tggtaaaggg cgcctttcga tgtatgggca   3720

ccattcagca tctcaagtcc aaatttggag atggctatat cgtcacaatg aagatcaaat   3780

ccccgaagga cgacctgctt cctgacctga accctgtgga gcagttcttc caggggaact   3840

tcccaggcag tgtgcagagg gagaggcact acaacatgct ccagttccag gtctcctcct   3900

cctccctggc gaggatcttc cagctcctcc tctcccacaa ggacagcctg ctcatcgagg   3960

agtactcagt cacacagacc acactggacc aggtgtttgt aaattttgct aaacagcaga   4020

ctgaaagtca tgacctccct ctgcaccctc gagctgctgg agccagtcga caagcccagg   4080

actgagcggc cgcttcgagc agacatgata agatacattg atgagtttgg acaaaccaca   4140

actagaatgc agtgaaaaaa atgctttatt tgtgaaattt gtgatgctat tgctttattt   4200

gtaaccatta taagctgcaa taaacaagtt aacaacaaca attgcattca ttttatgttt   4260

caggttcagg gggagatgtg ggaggttttt taaagcaagt aaaacctcta caaatgtggt   4320

aaaatcgata aggatcttcc tagagcatgg ctacgtagat aagtagcatg gcgggttaat   4380

cattaactac aaggaacccc tagtgatgga gttggccact ccctctctgc gcgctcgctc   4440

gctcactgag gccgggcgac caaaggtcgc ccgacgcccg ggctttgccc gggcggcctc   4500

agtgagcgag cgagcgcgca g                                             4521
```

<210> SEQ ID NO 18
<211> LENGTH: 175
<212> TYPE: DNA
<213> ORGANISM: Artificial Sequence
<220> FEATURE:
<223> OTHER INFORMATION: synthetic

<400> SEQUENCE: 18

```
ctctcccccc tgtcgcgttc gctcgctcgc tggctcgttt ggggggggtgg cagctcaaag     60

agctgccaga cgacggccct ctggccgtcg ccccccccaaa cgagccagcg agcgagcgaa    120

cgcgacaggg gggagagtgc cacactctca agcaaggggg ttttgtaagc agtga         175
```

<210> SEQ ID NO 19
<211> LENGTH: 400
<212> TYPE: DNA
<213> ORGANISM: Artificial Sequence
<220> FEATURE:
<223> OTHER INFORMATION: synthetic

<400> SEQUENCE: 19

```
gctagcgtgc cacctggtcg acattgatta ttgactagtt attaatagta atcaattacg     60

gggtcattag ttcatagccc atatatggag ttccgcgtta cataacttac ggtaaatggc    120

ccgcctggct gaccgcccaa cgacccccgc ccattgacgt caataatgac gtatgttccc    180

atagtaacgc caatagggac tttccattga cgtcaatggg tggactattt acggtaaact    240

gcccacttgg cagtacatca agtgtatcat atgccaagta cgccccctat tgacgtcaat    300

gacggtaaat ggcccgcctg gcattatgcc cagtacatga ccttatggga ctttcctact    360

tggcagtaca tctacgtatt agtcatcgct attaccatgg                          400
```

<210> SEQ ID NO 20

<211> LENGTH: 277
<212> TYPE: DNA
<213> ORGANISM: Artificial Sequence
<220> FEATURE:
<223> OTHER INFORMATION: synthetic

<400> SEQUENCE: 20 tcgaggtgag ccccacgttc tgcttcactc tccccatctc ccccccctcc ccacccccaa 60 ttttgtattt atttattttt taattatttt gtgcagcgat gggggcgggg gggggggggg 120 cgcgcgccag gcggggcggg gcggggcgag gggcggggcg gggcgaggcg gagaggtgcg 180 gcggcagcca atcagagcgg cgcgctccga aagtttcctt ttatggcgag gcggcggcgg 240 cggcggccct ataaaaagcg aagcgcgcgg cgggcgg 277

<210> SEQ ID NO 21
<211> LENGTH: 133
<212> TYPE: DNA
<213> ORGANISM: Artificial Sequence
<220> FEATURE:
<223> OTHER INFORMATION: synthetic

<400> SEQUENCE: 21 gtaagtatca aggttacaag acaggtttaa ggagaccaat agaaactggg cttgtcgaga 60 cagagaagac tcttgcgttt ctgataggca cctattggtc ttactgacat ccactttgcc 120 tttctctcca cag 133

<210> SEQ ID NO 22
<211> LENGTH: 3108
<212> TYPE: DNA
<213> ORGANISM: Artificial Sequence
<220> FEATURE:
<223> OTHER INFORMATION: synthetic

<400> SEQUENCE: 22 atggtgattc ttcagcaggg ggaccatgtg tggatggacc tgagattggg gcaggagttc 60 gacgtgccca tcggggcggt ggtgaagctc tgcgactctg ggcaggtcca ggtggtggat 120 gatgaagaca atgaacactg gatctctccg cagaacgcaa cgcacatcaa gcctatgcac 180 cccacgtcgg tccacggcgt ggaggacatg atccgcctgg gggacctcaa cgaggcgggc 240 atcttgcgca acctgcttat ccgctaccgg gaccacctca tctacacgta tacgggctcc 300 atcctggtgg ctgtgaaccc ctaccagctg ctctccatct actcgccaga gcacatccgc 360 cagtatacca acaagaagat tggggagatg cccccccaca tctttgccat tgctgacaac 420 tgctacttca acatgaaacg caacagccga gaccagtgct gcatcatcag tggggaatct 480 ggggccggga agacggagag cacaaagctg atcctgcagt tcctggcagc catcagtggg 540 cagcactcgt ggattgagca gcaggtcttg gaggccaccc ccattctgga agcatttggg 600 aatgccaaga ccatccgcaa tgacaactca agccgtttcg gaaagtacat cgacatccac 660 ttcaacaagc ggggcgccat cgagggcgcg aagattgagc agtacctgct ggaaaagtca 720 cgtgtctgtc gccaggccct ggatgaaagg aactaccacg tgttctactg catgctggag 780 ggcatgagtg aggatcagaa gaagaagctg ggcttgggcc aggcctctga ctacaactac 840 ttggccatgg gtaactgcat aacctgtgag ggccgggtgg acagccagga gtacgccaac 900 atccgctccg ccatgaaggt gctcatgttc actgacaccg agaactggga gatctcgaag 960 ctcctggctg ccatcctgca cctgggcaac ctgcagtatg aggcacgcac atttgaaaac 1020 ctggatgcct gtgaggttct cttctcccca tcgctggcca cagctgcatc cctgcttgag 1080

```
gtgaaccccc cagacctgat gagctgcctg actagccgca ccctcatcac ccgcggggag   1140
acggtgtcca ccccactgag cagggaacag gcactggacg tgcgcgacgc cttcgtaaag   1200
gggatctacg ggcggctgtt cgtgtggatt gtggacaaga tcaacgcagc aatttacaag   1260
cctccctccc aggatgtgaa gaactctcgc aggtccatcg gcctcctgga catctttggg   1320
tttgagaact ttgctgtgaa cagctttgag cagctctgca tcaacttcgc caatgagcac   1380
ctgcagcagt tctttgtgcg gcacgtgttc aagctggagc aggaggaata tgacctggag   1440
agcattgact ggctgcacat cgagttcact gacaaccagg atgccctgga catgattgcc   1500
aacaagccca tgaacatcat ctccctcatc gatgaggaga gcaagttccc caagggcaca   1560
gacaccacca tgttacacaa gctgaactcc cagcacaagc tcaacgccaa ctacatcccc   1620
cccaagaaca accatgagac ccagtttggc atcaaccatt ttgcaggcat cgtctactat   1680
gagacccaag gcttcctgga gaagaaccga gacaccctgc atggggacat tatccagctg   1740
gtccactcct ccaggaacaa gttcatcaag cagatcttcc aggccgatgt cgccatgggc   1800
gccgagacca ggaagcgctc gcccacactt agcagccagt tcaagcggtc actggagctg   1860
ctgatgcgca cgctgggtgc ctgccagccc ttctttgtgc gatgcatcaa gcccaatgag   1920
ttcaagaagc ccatgctgtt cgaccggcac ctgtgcgtgc gccagctgcg gtactcagga   1980
atgatggaga ccatccgaat ccgccgagct ggctacccca tccgctacag cttcgtagag   2040
tttgtggagc ggtaccgtgt gctgctgcca ggtgtgaagc cggcctacaa gcagggcgac   2100
ctccgcggga cttgccagcg catggctgag gctgtgctgg gcacccacga tgactggcag   2160
ataggcaaaa ccaagatctt tctgaaggac caccatgaca tgctgctgga agtggagcgg   2220
gacaaagcca tcaccgacag agtcatcctc cttcagaaag tcatccgggg attcaaagac   2280
aggtctaact ttctgaagct gaagaacgct gccacactga tccagaggca ctggcggggt   2340
cacaactgta ggaagaacta cgggctgatg cgtctgggct tcctgcggct gcaggccctg   2400
caccgctccc ggaagctgca ccagcagtac cgcctggccc gccagcgcat catccagttc   2460
caggcccgct gccgcgccta tctggtgcgc aaggccttcc gccaccgcct ctgggctgtg   2520
ctcaccgtgc aggcctatgc ccggggcatg atcgcccgca ggctgcacca acgcctcagg   2580
gctgagtatc tgtggcgcct cgaggctgag aaaatgcggc tggcggagga agagaagctt   2640
cggaaggaga tgagcgccaa gaaggccaag gaggaggccg agcgcaagca tcaggagcgc   2700
ctggcccagc tggctcgtga ggacgctgag cgggagctga aggagaagga ggccgctcgg   2760
cggaagaagg agctcctgga gcagatggaa agggcccgcc atgagcctgt caatcactca   2820
gacatggtgg acaagatgtt tggcttcctg gggacttcag gtggcctgcc aggccaggag   2880
ggccaggcac ctagtggctt tgaggacctg gagcgagggc ggagggagat ggtggaggag   2940
gacctggatg cagccctgcc cctgcctgac gaggatgagg aggacctctc tgagtataaa   3000
tttgccaagt tcgcggccac ctacttccag gggacaacta cgcactccta cacccggcgg   3060
ccactcaaac agccactgct ctaccatgac gacgagggtg accagctg                3108
```

<210> SEQ ID NO 23
<211> LENGTH: 4577
<212> TYPE: DNA
<213> ORGANISM: Artificial Sequence
<220> FEATURE:
<223> OTHER INFORMATION: synthetic

<400> SEQUENCE: 23

-continued

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcc taatcgggaa ttcgccctta agctagcgtg ccacctggtc gacattgatt    240
attgactagt tattaatagt aatcaattac ggggtcatta gttcatagcc catatatgga    300
gttccgcgtt acataactta cggtaaatgg cccgcctggc tgaccgccca acgacccccg    360
cccattgacg tcaataatga cgtatgttcc catagtaacg ccaataggga ctttccattg    420
acgtcaatgg gtggactatt tacggtaaac tgcccacttg gcagtacatc aagtgtatca    480
tatgccaagt acgcccccta ttgacgtcaa tgacggtaaa tggcccgcct ggcattatgc    540
ccagtacatg accttatggg actttcctac ttggcagtac atctacgtat tagtcatcgc    600
tattaccatg ggtcgaggtg agccccacgt tctgcttcac tctccccatc tcccccccct    660
ccccaccccc aattttgtat ttatttattt tttaattatt ttgtgcagcg atgggggcgg    720
gggggggggg ggcgcgcgcc aggcggggcg gggcggggcg aggggcgggg cggggcgagg    780
cggagaggtg cggcggcagc caatcagagc ggcgcgctcc gaaagtttcc ttttatggcg    840
aggcggcggc ggcggcggcc ctataaaaag cgaagcgcgc ggcgggcggc tgcagaagtt    900
ggtcgtgagg cactgggcag gtaagtatca aggttacaag acaggtttaa ggagaccaat    960
agaaactggg cttgtcgaga cagagaagac tcttgcgttt ctgataggca cctattggtc   1020
ttactgacat ccactttgcc tttctctcca caggtgtcca ggcggccgcc atggtgattc   1080
ttcagcaggg ggaccatgtg tggatggacc tgagattggg gcaggagttc gacgtgccca   1140
tcggggcggt ggtgaagctc tgcgactctg ggcaggtcca ggtggtggat gatgaagaca   1200
atgaacactg gatctctccg cagaacgcaa cgcacatcaa gcctatgcac cccacgtcgg   1260
tccacggcgt ggaggacatg atccgcctgg gggacctcaa cgaggcgggc atcttgcgca   1320
acctgcttat ccgctaccgg gaccacctca tctacacgta tacgggctcc atcctggtgg   1380
ctgtgaaccc ctaccagctg ctctccatct actcgccaga gcacatccgc cagtatacca   1440
acaagaagat tggggagatg cccccccaca tctttgccat tgctgacaac tgctacttca   1500
acatgaaacg caacagccga gaccagtgct gcatcatcag tggggaatct ggggccggga   1560
agacggagag cacaaagctg atcctgcagt tcctggcagc catcagtggg cagcactcgt   1620
ggattgagca gcaggtcttg gaggccaccc ccattctgga agcatttggg aatgccaaga   1680
ccatccgcaa tgacaactca agccgtttcg gaaagtacat cgacatccac ttcaacaagc   1740
ggggcgccat cgagggcgcg aagattgagc agtacctgct ggaaaagtca cgtgtctgtc   1800
gccaggccct ggatgaaagg aactaccacg tgttctactg catgctggag ggcatgagtg   1860
aggatcagaa gaagaagctg ggcttgggcc aggcctctga ctacaactac ttggccatgg   1920
gtaactgcat aacctgtgag ggccgggtgg acagccagga gtacgccaac atccgctccg   1980
ccatgaaggt gctcatgttc actgacaccg agaactggga gatctcgaag ctcctggctg   2040
ccatcctgca cctgggcaac ctgcagtatg aggcacgcac atttgaaaac ctggatgcct   2100
gtgaggttct cttctcccca tcgctggcca cagctgcatc cctgcttgag gtgaaccccc   2160
cagacctgat gagctgcctg actagccgca ccctcatcac ccgcggggag acggtgtcca   2220
ccccactgag cagggaacag gcactggacg tgcgcgacgc cttcgtaaag gggatctacg   2280
ggcggctgtt cgtgtggatt gtggacaaga tcaacgcagc aatttacaag cctccctccc   2340
aggatgtgaa gaactctcgc aggtccatcg gcctcctgga catctttggg tttgagaact   2400
```

```
ttgctgtgaa cagctttgag cagctctgca tcaacttcgc caatgagcac ctgcagcagt   2460
tctttgtgcg gcacgtgttc aagctggagc aggaggaata tgacctggag agcattgact   2520
ggctgcacat cgagttcact gacaaccagg atgccctgga catgattgcc aacaagccca   2580
tgaacatcat ctccctcatc gatgaggaga gcaagttccc caagggcaca gacaccacca   2640
tgttacacaa gctgaactcc cagcacaagc tcaacgccaa ctacatcccc cccaagaaca   2700
accatgagac ccagtttggc atcaaccatt ttgcaggcat cgtctactat gagacccaag   2760
gcttcctgga gaagaaccga gacaccctgc atggggacat tatccagctg gtccactcct   2820
ccaggaacaa gttcatcaag cagatcttcc aggccgatgt cgccatgggc gccgagacca   2880
ggaagcgctc gcccacactt agcagccagt tcaagcggtc actggagctg ctgatgcgca   2940
cgctgggtgc ctgccagccc ttctttgtgc gatgcatcaa gcccaatgag ttcaagaagc   3000
ccatgctgtt cgaccggcac ctgtgcgtgc gccagctgcg gtactcagga atgatggaga   3060
ccatccgaat ccgccgagct ggctacccca tccgctacag cttcgtagag tttgtggagc   3120
ggtaccgtgt gctgctgcca ggtgtgaagc cggcctacaa gcagggcgac ctccgcggga   3180
cttgccagcg catggctgag gctgtgctgg gcacccacga tgactggcag ataggcaaaa   3240
ccaagatctt tctgaaggac caccatgaca tgctgctgga agtggagcgg gacaaagcca   3300
tcaccgacag agtcatcctc cttcagaaag tcatccgggg attcaaagac aggtctaact   3360
ttctgaagct gaagaacgct gccacactga tccagaggca ctggcggggt cacaactgta   3420
ggaagaacta cgggctgatg cgtctgggct tcctgcggct gcaggccctg caccgctccc   3480
ggaagctgca ccagcagtac cgcctggccc gccagcgcat catccagttc caggcccgct   3540
gccgcgccta tctggtgcgc aaggccttcc gccaccgcct ctgggctgtg ctcaccgtgc   3600
aggcctatgc ccggggcatg atcgcccgca ggctgcacca acgcctcagg gctgagtatc   3660
tgtggcgcct cgaggctgag aaaatgcggc tggcggagga agagaagctt cggaaggaga   3720
tgagcgccaa gaaggccaag gaggaggccg agcgcaagca tcaggagcgc ctggcccagc   3780
tggctcgtga ggacgctgag cgggagctga aggagaagga ggccgctcgg cggaagaagg   3840
agctcctgga gcagatggaa agggcccgcc atgagcctgt caatcactca gacatggtgg   3900
acaagatgtt tggcttcctg gggacttcag gtggcctgcc aggccaggag ggccaggcac   3960
ctagtggctt tgaggacctg gagcgagggc ggagggagat ggtggaggag gacctggatg   4020
cagccctgcc cctgcctgac gaggatgagg aggacctctc tgagtataaa tttgccaagt   4080
tcgcggccac ctacttccag gggacaacta cgcactccta cacccggcgg ccactcaaac   4140
agccactgct ctaccatgac gacgagggtg accagctggt aagtatcaag gttacaagac   4200
aggtttaagg agaccaatag aaactgggct tgtcgagaca gagaagactc ttgcgtttct   4260
gggattttgc cgatttcggc ctattggtta aaaaatgagc tgatttaaca aaaatttaac   4320
gcgaatttta acaaaatatt aacgtttata atttcaggtg gcatctttcc aattgaaggg   4380
cgaattccga tcttcctaga gcatggctac gtagataagt agcatggcgg gttaatcatt   4440
aactacaagg aacccctagt gatggagttg gccactccct ctctgcgcgc tcgctcgctc   4500
actgaggccg ggcgaccaaa ggtcgcccga cgcccgggct ttgcccgggc ggcctcagtg   4560
agcgagcgag cgcgcag                                                  4577
```

<210> SEQ ID NO 24
<211> LENGTH: 3540
<212> TYPE: DNA

<213> ORGANISM: Artificial Sequence
<220> FEATURE:
<223> OTHER INFORMATION: synthetic

<400> SEQUENCE: 24 gcagccctgg cggtctggat caccatcctc cgcttcatgg gggacctccc tgagcccaag 60 taccacacag ccatgagtga tggcagtgag aagatccctg tgatgaccaa gatttatgag 120 accctgggca agaagacgta caagagggag ctgcaggccc tgcagggcga gggcgaggcc 180 cagctccccg agggccagaa gaagagcagt gtgaggcaca agctggtgca tttgactctg 240 aaaaagaagt ccaagctcac agaggaggtg accaagaggc tgcatgacgg ggagtccaca 300 gtgcagggca acagcatgct ggaggaccgg cccacctcca acctggagaa gctgcacttc 360 atcatcggca atggcatcct gcggccagca ctccgggacg agatctactg ccagatcagc 420 aagcagctga cccacaaccc ctccaagagc agctatgccc ggggctggat tctcgtgtct 480 ctctgcgtgg gctgtttcgc cccctccgag aagtttgtca agtacctgcg gaacttcatc 540 cacgggggcc cgcccggcta cgccccgtac tgtgaggagc gcctgagaag gacctttgtc 600 aatgggacac ggacacagcc gcccagctgg ctggagctgc aggccaccaa gtccaagaag 660 ccaatcatgt tgcccgtgac attcatggat gggaccacca agaccctgct gacggactcg 720 gcaaccacgg ccaaggagct ctgcaacgcg ctggccgaca agatctctct caaggaccgg 780 ttcgggttct ccctctacat tgccctgttt gacaaggtgt cctccctggg cagcggcagt 840 gaccacgtca tggacgccat ctcccagtgc gagcagtacg ccaaggagca gggcgcccag 900 gagcgcaacg ccccctggag gctcttcttc cgcaaagagg tcttcacgcc ctggcacagc 960 ccctccgagg acaacgtggc caccaacctc atctaccagc aggtggtgcg aggagtcaag 1020 tttggggagt acaggtgtga gaaggaggac gacctggctg agctggcctc ccagcagtac 1080 tttgtagact atggctctga gatgatcctg gagcgcctcc tgaacctcgt gcccacctac 1140 atccccgacc gcgagatcac gcccctgaag acgctggaga agtgggccca gctggccatc 1200 gccgcccaca agaaggggat ttatgcccag aggagaactg atgcccagaa ggtcaaagag 1260 gatgtggtca gttatgcccg cttcaagtgg cccttgctct tctccaggtt ttatgaagcc 1320 tacaaattct caggccccag tctccccaag aacgacgtca tcgtggccgt caactggacg 1380 ggtgtgtact ttgtggatga gcaggagcag gtacttctgg agctgtcctt cccagagatc 1440 atggccgtgt ccagcagcag ggagtgccgt gtctggctct cactgggctg ctctgatctt 1500 ggctgtgctg cgcctcactc aggctgggca ggactgaccc cggcggggcc ctgttctccg 1560 tgttggtcct gcaggggagc gaaaacgacg gcccccagct tcacgctggc caccatcaag 1620 ggggacgaat acaccttcac ctccagtaat gctgaggaca ttcgtgacct ggtggtcacc 1680 ttcctagagg ggctccggaa gagatctaag tatgttgtgg ccctgcagga taaccccaac 1740 cccgcaggcg aggagtcagg cttcctcagc tttgccaagg gagacctcat catcctggac 1800 catgacacgg gcgagcaggt catgaactcg ggctgggcca acggcatcaa tgagaggacc 1860 aagcagcgtg gggacttccc caccgactgt gtgtacgtca tgcccactgt caccatgcca 1920 cctcgtgaga ttgtggccct ggtcaccatg actcccgatc agaggcagga cgttgtccgg 1980 ctcttgcagc tgcgaacggc ggagcccgag gtgcgtgcca agccctacac gctggaggag 2040 ttttcctatg actacttcag gcccccaccc aagcacacgc tgagccgtgt catggtgtcc 2100 aaggcccgag gcaaggaccg gctgtggagc cacacgcggg aaccgctcaa gcaggcgctg 2160 ctcaagaagc tcctgggcag tgaggagctc tcgcaggagg cctgcctggc cttcattgct 2220 gtgctcaagt acatgggcga ctacccgtcc aagaggacac gctccgtcaa tgagctcacc 2280 gaccagatct ttgagggtcc cctgaaagcc gagcccctga aggacgaggc atatgtgcag 2340 atcctgaagc agctgaccga caaccacatc aggtacagcg aggagcgggg ttgggagctg 2400 ctctggctgt gcacgggcct tttcccaccc agcaacatcc tcctgcccca cgtgcagcgc 2460 ttcctgcagt cccgaaagca ctgcccactc gccatcgact gcctgcaacg gctccagaaa 2520 gccctgagaa acgggtcccg gaagtaccct ccgcacctgg tggaggtgga ggccatccag 2580 cacaagacca cccagatttt ccacaaggtc tacttccctg atgacactga cgaggccttc 2640 gaagtggagt ccagcaccaa ggccaaggac ttctgccaga acatcgccac caggctgctc 2700 ctcaagtcct cagagggatt cagcctcttt gtcaaaattg cagacaaggt catcagcgtt 2760 cctgagaatg acttcttctt tgactttgtt cgacacttga cagactggat aaagaaagct 2820 cggcccatca aggacggaat tgtgccctca ctcacctacc aggtgttctt catgaagaag 2880 ctgtggacca ccacggtgcc agggaaggat cccatggccg attccatctt ccactattac 2940 caggagttgc ccaagtatct ccgaggctac cacaagtgca cgcgggagga ggtgctgcag 3000 ctgggggcgc tgatctacag ggtcaagttc gaggaggaca agtcctactt ccccagcatc 3060 cccaagctgc tgcgggagct ggtgccccag gaccttatcc ggcaggtctc acctgatgac 3120 tggaagcggt ccatcgtcgc ctacttcaac aagcacgcag ggaagtccaa ggaggaggcc 3180 aagctggcct tcctgaagct catcttcaag tggcccacct ttggctcagc cttcttcgag 3240 gtgaagcaaa ctacggagcc aaacttccct gagatcctcc taattgccat caacaagtat 3300 ggggtcagcc tcatcgatcc caaaacgaag gatatcctca ccactcatcc cttcaccaag 3360 atctccaact ggagcagcgg caacacctac ttccacatca ccattgggaa cttggtgcgc 3420 gggagcaaac tgctctgcga gacgtcactg ggctacaaga tggatgacct cctgacttcc 3480 tacattagcc agatgctcac agccatgagc aaacagcggg gctccaggag cggcaagtga 3540

<210> SEQ ID NO 25
<211> LENGTH: 215
<212> TYPE: DNA
<213> ORGANISM: Artificial Sequence
<220> FEATURE:
<223> OTHER INFORMATION: synthetic

<400> SEQUENCE: 25 gcctcgactg tgccttctag ttgccagcca tctgttgttt gcccctcccc cgtgccttcc 60 ttgaccctgg aaggtgccac tcccactgtc ctttcctaat aaaatgagga aattgcatcg 120 cattgtctga gtaggtgtca ttctattctg gggggtgggg tggggcagga cagcaagggg 180 gaggattggg aagacaatag caggcatgct gggga 215

<210> SEQ ID NO 26
<211> LENGTH: 4389
<212> TYPE: DNA
<213> ORGANISM: Artificial Sequence
<220> FEATURE:
<223> OTHER INFORMATION: synthetic

<400> SEQUENCE: 26 ctgcgcgctc gctcgctcac tgaggccgcc cgggcaaagc ccgggcgtcg ggcgaccttt 60 ggtcgcccgg cctcagtgag cgagcgagcg cgcagagagg gagtggccaa ctccatcact 120 aggggttcct tgtagttaat gattaacccg ccatgctact tatctacgta gccatgctct 180

```
aggaagatcg gaattcgccc tttgatcagg gattttgccg atttcggcct attggttaaa    240
aaatgagctg atttaacaaa aatttaacgc gaattttaac aaaatattaa cgtttataat    300
ttcaggtggc atctttcgat aggcacctat tggtcttact gacatccact ttgcctttct    360
ctccacaggc agccctggcg gtctggatca ccatcctccg cttcatgggg gacctccctg    420
agcccaagta ccacacagcc atgagtgatg gcagtgagaa gatccctgtg atgaccaaga    480
tttatgagac cctgggcaag aagacgtaca agagggagct gcaggccctg cagggcgagg    540
gcgaggccca gctccccgag ggccagaaga agagcagtgt gaggcacaag ctggtgcatt    600
tgactctgaa aaagaagtcc aagctcacag aggaggtgac caagaggctg catgacgggg    660
agtccacagt gcagggcaac agcatgctgg aggaccggcc cacctccaac ctggagaagc    720
tgcacttcat catcggcaat ggcatcctgc ggccagcact ccgggacgag atctactgcc    780
agatcagcaa gcagctgacc cacaacccct ccaagagcag ctatgcccgg ggctggattc    840
tcgtgtctct ctgcgtgggc tgtttcgccc cctccgagaa gtttgtcaag tacctgcgga    900
acttcatcca cgggggcccg cccggctacg ccccgtactg tgaggagcgc ctgagaagga    960
cctttgtcaa tgggacacgg acacagccgc ccagctggct ggagctgcag gccaccaagt   1020
ccaagaagcc aatcatgttg cccgtgacat tcatggatgg gaccaccaag accctgctga   1080
cggactcggc aaccacggcc aaggagctct gcaacgcgct ggccgacaag atctctctca   1140
aggaccggtt cgggttctcc ctctacattg ccctgtttga caaggtgtcc tccctgggca   1200
gcggcagtga ccacgtcatg gacgccatct cccagtgcga gcagtacgcc aaggagcagg   1260
gcgcccagga gcgcaacgcc ccctggaggc tcttcttccg caaagaggtc ttcacgccct   1320
ggcacagccc ctccgaggac aacgtggcca ccaacctcat ctaccagcag gtggtgcgag   1380
gagtcaagtt tggggagtac aggtgtgaga aggaggacga cctggctgag ctggcctccc   1440
agcagtactt tgtagactat ggctctgaga tgatcctgga gcgcctcctg aacctcgtgc   1500
ccacctacat ccccgaccgc gagatcacgc ccctgaagac gctggagaag tgggcccagc   1560
tggccatcgc cgcccacaag aaggggattt atgcccagag gagaactgat gcccagaagg   1620
tcaaagagga tgtggtcagt tatgcccgct tcaagtggcc cttgctcttc tccaggtttt   1680
atgaagccta caaattctca ggccccagtc tccccaagaa cgacgtcatc gtggccgtca   1740
actggacggg tgtgtacttt gtggatgagc aggagcaggt acttctggag ctgtccttcc   1800
cagagatcat ggccgtgtcc agcagcaggg agtgccgtgt ctggctctca ctgggctgct   1860
ctgatcttgg ctgtgctgcg cctcactcag gctgggcagg actgaccccg gcggggccct   1920
gttctccgtg ttggtcctgc aggggagcga aaacgacggc ccccagcttc acgctggcca   1980
ccatcaaggg ggacgaatac accttcacct ccagtaatgc tgaggacatt cgtgacctgg   2040
tggtcacctt cctagagggg ctccggaaga gatctaagta tgttgtggcc ctgcaggata   2100
accccaaccc cgcaggcgag gagtcaggct tcctcagctt tgccaaggga gacctcatca   2160
tcctggacca tgacacgggc gagcaggtca tgaactcggg ctgggccaac ggcatcaatg   2220
agaggaccaa gcagcgtggg gacttcccca ccgactgtgt gtacgtcatg cccactgtca   2280
ccatgccacc tcgtgagatt gtggccctgg tcaccatgac tcccgatcag aggcaggacg   2340
ttgtccggct cttgcagctg cgaacggcgg agcccgaggt gcgtgccaag ccctacacgc   2400
tggaggagtt ttcctatgac tacttcaggc ccccacccaa gcacacgctg agccgtgtca   2460
tggtgtccaa ggcccgaggc aaggaccggc tgtggagcca cacgcgggaa ccgctcaagc   2520
aggcgctgct caagaagctc ctgggcagtg aggagctctc gcaggaggcc tgcctggcct   2580
```

tcattgctgt gctcaagtac atgggcgact acccgtccaa gaggacacgc tccgtcaatg 2640 agctcaccga ccagatcttt gagggtcccc tgaaagccga gcccctgaag gacgaggcat 2700 atgtgcagat cctgaagcag ctgaccgaca accacatcag gtacagcgag gagcggggtt 2760 gggagctgct ctggctgtgc acgggccttt tcccacccag caacatcctc ctgccccacg 2820 tgcagcgctt cctgcagtcc cgaaagcact gcccactcgc catcgactgc ctgcaacggc 2880 tccagaaagc cctgagaaac gggtcccgga agtaccctcc gcacctggtg gaggtggagg 2940 ccatccagca caagaccacc cagattttcc acaaggtcta cttccctgat gacactgacg 3000 aggccttcga agtggagtcc agcaccaagg ccaaggactt ctgccagaac atcgccacca 3060 ggctgctcct caagtcctca gagggattca gcctctttgt caaaattgca gacaaggtca 3120 tcagcgttcc tgagaatgac ttcttctttg actttgttcg acacttgaca gactggataa 3180 agaaagctcg gcccatcaag gacggaattg tgccctcact cacctaccag gtgttcttca 3240 tgaagaagct gtggaccacc acggtgccag ggaaggatcc catggccgat tccatcttcc 3300 actattacca ggagttgccc aagtatctcc gaggctacca caagtgcacg cgggaggagg 3360 tgctgcagct gggggcgctg atctacaggg tcaagttcga ggaggacaag tcctacttcc 3420 ccagcatccc caagctgctg cgggagctgg tgccccagga ccttatccgg caggtctcac 3480 ctgatgactg gaagcggtcc atcgtcgcct acttcaacaa gcacgcaggg aagtccaagg 3540 aggaggccaa gctggccttc ctgaagctca tcttcaagtg gcccaccttt ggctcagcct 3600 tcttcgaggt gaagcaaact acggagccaa acttccctga gatcctccta attgccatca 3660 acaagtatgg ggtcagcctc atcgatccca aaacgaagga tatcctcacc actcatccct 3720 tcaccaagat ctccaactgg agcagcggca acacctactt ccacatcacc attgggaact 3780 tggtgcgcgg gagcaaactg ctctgcgaga cgtcactggg ctacaagatg gatgacctcc 3840 tgacttccta cattagccag atgctcacag ccatgagcaa acagcggggc tccaggagcg 3900 gcaagtgacc gcggcctgct gccggctctg cggcctcttc cgcgtcttcg agatctgcct 3960 cgactgtgcc ttctagttgc cagccatctg ttgtttgccc ctcccccgtg ccttccttga 4020 ccctggaagg tgccactccc actgtccttt cctaataaaa tgaggaaatt gcatcgcatt 4080 gtctgagtag gtgtcattct attctggggg gtggggtggg gcaggacagc aagggggagg 4140 attgggaaga caatagcagg catgctgggg actcgagtta agggcgcaat tcccgattag 4200 gatcttccta gagcatggct acgtagataa gtagcatggc gggttaatca ttaactacaa 4260 ggaaccccta gtgatggagt tggccactcc ctctctgcgc gctcgctcgc tcactgaggc 4320 cgggcgacca aaggtcgccc gacgcccggg ctttgcccgg gcggcctcag tgagcgagcg 4380 agcgcgcag 4389

<210> SEQ ID NO 27
<211> LENGTH: 4468
<212> TYPE: DNA
<213> ORGANISM: Artificial Sequence
<220> FEATURE:
<223> OTHER INFORMATION: synthetic

<400> SEQUENCE: 27 ctgcgcgctc gctcgctcac tgaggccgcc cgggcaaagc ccgggcgtcg ggcgaccttt 60 ggtcgcccgg cctcagtgag cgagcgagcg cgcagagagg gagtggccaa ctccatcact 120 aggggttcct tgtagttaat gattaacccg ccatgctact tatctacgta gccatgctct 180

-continued

```
aggaagatcc taatcgggaa ttcgccctta agctagcgtg ccacctggtc gacattgatt    240
attgactagt tattaatagt aatcaattac ggggtcatta gttcatagcc catatatgga    300
gttccgcgtt acataactta cggtaaatgg cccgcctggc tgaccgccca acgacccccg    360
cccattgacg tcaataatga cgtatgttcc catagtaacg ccaataggga ctttccattg    420
acgtcaatgg gtggactatt tacggtaaac tgcccacttg gcagtacatc aagtgtatca    480
tatgccaagt acgcccccta ttgacgtcaa tgacggtaaa tggcccgcct ggcattatgc    540
ccagtacatg accttatggg actttcctac ttggcagtac atctacgtat tagtcatcgc    600
tattaccatg ggtcgaggtg agccccacgt tctgcttcac tctccccatc tcccccccct    660
ccccaccccc aattttgtat ttatttattt tttaattatt ttgtgcagcg atgggggcgg    720
gggggggggg ggcgcgcgcc aggcggggcg gggcggggcg aggggcgggg cggggcgagg    780
cggagaggtg cggcggcagc caatcagagc ggcgcgctcc gaaagtttcc ttttatggcg    840
aggcggcggc ggcggcggcc ctataaaaag cgaagcgcgc ggcgggcggc tgcagaagtt    900
ggtcgtgagg cactgggcag gtaagtatca aggttacaag acaggtttaa ggagaccaat    960
agaaactggg cttgtcgaga cagagaagac tcttgcgttt ctgataggca cctattggtc   1020
ttactgacat ccactttgcc tttctctcca caggtgtcca ggcggccgcc atggtgattc   1080
ttcagcaggg ggaccatgtg tggatggacc tgagattggg gcaggagttc gacgtgccca   1140
tcggggcggt ggtgaagctc tgcgactctg ggcaggtcca ggtggtggat gatgaagaca   1200
atgaacactg gatctctccg cagaacgcaa cgcacatcaa gcctatgcac cccacgtcgg   1260
tccacggcgt ggaggacatg atccgcctgg gggacctcaa cgaggcgggc atcttgcgca   1320
acctgcttat ccgctaccgg gaccacctca tctacacgta tacgggctcc atcctggtgg   1380
ctgtgaaccc ctaccagctg ctctccatct actcgccaga gcacatccgc cagtatacca   1440
acaagaagat tggggagatg ccccccccaca tctttgccat tgctgacaac tgctacttca   1500
acatgaaacg caacagccga gaccagtgct gcatcatcag tggggaatct ggggccggga   1560
agacggagag cacaaagctg atcctgcagt tcctggcagc catcagtggg cagcactcgt   1620
ggattgagca gcaggtcttg gaggccaccc ccattctgga agcatttggg aatgccaaga   1680
ccatccgcaa tgacaactca agccgtttcg gaaagtacat cgacatccac ttcaacaagc   1740
ggggcgccat cgagggcgcg aagattgagc agtacctgct ggaaaagtca cgtgtctgtc   1800
gccaggccct ggatgaaagg aactaccacg tgttctactg catgctggag ggcatgagtg   1860
aggatcagaa gaagaagctg ggcttgggcc aggcctctga ctacaactac ttggccatgg   1920
gtaactgcat aacctgtgag ggccgggtgg acagccagga gtacgccaac atccgctccg   1980
ccatgaaggt gctcatgttc actgacaccg agaactggga gatctcgaag ctcctggctg   2040
ccatcctgca cctgggcaac ctgcagtatg aggcacgcac atttgaaaac ctggatgcct   2100
gtgaggttct cttctcccca tcgctggcca cagctgcatc cctgcttgag gtgaaccccc   2160
cagacctgat gagctgcctg actagccgca ccctcatcac ccgcggggag acggtgtcca   2220
ccccactgag cagggaacag gcactggacg tgcgcgacgc cttcgtaaag gggatctacg   2280
ggcggctgtt cgtgtggatt gtggacaaga tcaacgcagc aatttacaag cctccctccc   2340
aggatgtgaa gaactctcgc aggtccatcg gcctcctgga catctttggg tttgagaact   2400
ttgctgtgaa cagctttgag cagctctgca tcaacttcgc caatgagcac ctgcagcagt   2460
tctttgtgcg gcacgtgttc aagctggagc aggaggaata tgacctggag agcattgact   2520
ggctgcacat cgagttcact gacaaccagg atgccctgga catgattgcc aacaagccca   2580
```

```
tgaacatcat ctccctcatc gatgaggaga gcaagttccc caagggcaca gacaccacca   2640
tgttacacaa gctgaactcc cagcacaagc tcaacgccaa ctacatcccc cccaagaaca   2700
accatgagac ccagtttggc atcaaccatt ttgcaggcat cgtctactat gagacccaag   2760
gcttcctgga gaagaaccga gacaccctgc atggggacat tatccagctg gtccactcct   2820
ccaggaacaa gttcatcaag cagatcttcc aggccgatgt cgccatgggc gccgagacca   2880
ggaagcgctc gcccacactt agcagccagt tcaagcggtc actggagctg ctgatgcgca   2940
cgctgggtgc ctgccagccc ttctttgtgc gatgcatcaa gcccaatgag ttcaagaagc   3000
ccatgctgtt cgaccggcac ctgtgcgtgc gccagctgcg gtactcagga atgatggaga   3060
ccatccgaat ccgccgagct ggctacccca tccgctacag cttcgtagag tttgtggagc   3120
ggtaccgtgt gctgctgcca ggtgtgaagc cggcctacaa gcagggcgac ctccgcggga   3180
cttgccagcg catggctgag gctgtgctgg gcacccacga tgactggcag ataggcaaaa   3240
ccaagatctt tctgaaggac caccatgaca tgctgctgga agtggagcgg gacaaagcca   3300
tcaccgacag agtcatcctc cttcagaaag tcatccgggg attcaaagac aggtctaact   3360
ttctgaagct gaagaacgct gccacactga tccagaggca ctggcggggt cacaactgta   3420
ggaagaacta cgggctgatg cgtctgggct tcctgcggct gcaggccctg caccgctccc   3480
ggaagctgca ccagcagtac cgcctggccc gccagcgcat catccagttc caggcccgct   3540
gccgcgccta tctggtgcgc aaggccttcc gccaccgcct ctgggctgtg ctcaccgtgc   3600
aggcctatgc ccggggcatg atcgcccgca ggctgcacca acgcctcagg gctgagtatc   3660
tgtggcgcct cgaggctgag aaaatgcggc tggcggagga agagaagctt cggaaggaga   3720
tgagcgccaa gaaggccaag gaggaggccg agcgcaagca tcaggagcgc ctggcccagc   3780
tggctcgtga ggacgctgag cgggagctga aggagaagga ggccgctcgg cggaagaagg   3840
agctcctgga gcagatggaa agggcccgcc atgagcctgt caatcactca gacatggtgg   3900
acaagatgtt tggcttcctg gggacttcag gtggcctgcc aggccaggag ggccaggcac   3960
ctagtggctt tgaggacctg gagcgagggc ggagggagat ggtggaggag gacctggatg   4020
cagccctgcc cctgcctgac gaggatgagg aggacctctc tgagtataaa tttgccaagt   4080
tcgcggccac ctacttccag gggacaacta cgcactccta cacccggcgg ccactcaaac   4140
agccactgct ctaccatgac gacgagggtg accagctggt aagtatcaag gttacaagac   4200
aggtttaagg agaccaatag aaactgggct tgtcgagaca gagaagactc ttgcgtttct   4260
caattgaagg gcgaattccg atcttcctag agcatggcta cgtagataag tagcatggcg   4320
ggttaatcat taactacaag gaacccctag tgatggagtt ggccactccc tctctgcgcg   4380
ctcgctcgct cactgaggcc gggcgaccaa aggtcgcccg acgcccgggc tttgcccggg   4440
cggcctcagt gagcgagcga gcgcgcag                                      4468
```

<210> SEQ ID NO 28
<211> LENGTH: 4268
<212> TYPE: DNA
<213> ORGANISM: Artificial Sequence
<220> FEATURE:
<223> OTHER INFORMATION: synthetic

<400> SEQUENCE: 28

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
```

```
aggggttcct tgtagttaat gattaacccg ccatgctact tatctacgta gccatgctct    180
aggaagatcg gaattcgata ggcacctatt ggtcttactg acatccactt tgcctttctc    240
tccacaggca gccctggcgg tctggatcac catcctccgc ttcatggggg acctccctga    300
gcccaagtac cacacagcca tgagtgatgg cagtgagaag atccctgtga tgaccaagat    360
ttatgagacc ctgggcaaga agacgtacaa gagggagctg caggccctgc agggcgaggg    420
cgaggcccag ctccccgagg gccagaagaa gagcagtgtg aggcacaagc tggtgcattt    480
gactctgaaa aagaagtcca agctcacaga ggaggtgacc aagaggctgc atgacgggga    540
gtccacagtg cagggcaaca gcatgctgga ggaccggccc acctccaacc tggagaagct    600
gcacttcatc atcggcaatg gcatcctgcg gccagcactc cgggacgaga tctactgcca    660
gatcagcaag cagctgaccc acaacccctc caagagcagc tatgcccggg gctggattct    720
cgtgtctctc tgcgtgggct gtttcgcccc ctccgagaag tttgtcaagt acctgcggaa    780
cttcatccac gggggcccgc ccggctacgc cccgtactgt gaggagcgcc tgagaaggac    840
ctttgtcaat gggacacgga cacagccgcc cagctggctg gagctgcagg ccaccaagtc    900
caagaagcca atcatgttgc ccgtgacatt catggatggg accaccaaga ccctgctgac    960
ggactcggca accacggcca aggagctctg caacgcgctg gccgacaaga tctctctcaa   1020
ggaccggttc gggttctccc tctacattgc cctgtttgac aaggtgtcct ccctgggcag   1080
cggcagtgac cacgtcatgg acgccatctc ccagtgcgag cagtacgcca aggagcaggg   1140
cgcccaggag cgcaacgccc cctggaggct cttcttccgc aaagaggtct tcacgccctg   1200
gcacagcccc tccgaggaca acgtggccac caacctcatc taccagcagg tggtgcgagg   1260
agtcaagttt ggggagtaca ggtgtgagaa ggaggacgac ctggctgagc tggcctccca   1320
gcagtacttt gtagactatg gctctgagat gatcctggag cgcctcctga acctcgtgcc   1380
cacctacatc cccgaccgcg agatcacgcc cctgaagacg ctggagaagt gggcccagct   1440
ggccatcgcc gcccacaaga aggggattta tgcccagagg agaactgatg cccagaaggt   1500
caaagaggat gtggtcagtt atgcccgctt caagtggccc ttgctcttct ccaggtttta   1560
tgaagcctac aaattctcag gccccagtct ccccaagaac gacgtcatcg tggccgtcaa   1620
ctggacgggt gtgtactttg tggatgagca ggagcaggta cttctggagc tgtccttccc   1680
agagatcatg gccgtgtcca gcagcaggga gtgccgtgtc tggctctcac tgggctgctc   1740
tgatcttggc tgtgctgcgc ctcactcagg ctgggcagga ctgaccccgg cggggccctg   1800
ttctccgtgt tggtcctgca ggggagcgaa aacgacggcc cccagcttca cgctggccac   1860
catcaagggg gacgaataca ccttcacctc cagtaatgct gaggacattc gtgacctggt   1920
ggtcaccttc ctagaggggc tccggaagag atctaagtat gttgtggccc tgcaggataa   1980
ccccaacccc gcaggcgagg agtcaggctt cctcagcttt gccaagggag acctcatcat   2040
cctggaccat gacacgggcg agcaggtcat gaactcgggc tgggccaacg gcatcaatga   2100
gaggaccaag cagcgtgggg acttccccac cgactgtgtg tacgtcatgc ccactgtcac   2160
catgccacct cgtgagattg tggccctggt caccatgact cccgatcaga ggcaggacgt   2220
tgtccggctc ttgcagctgc gaacggcgga gcccgaggtg cgtgccaagc cctacacgct   2280
ggaggagttt tcctatgact acttcaggcc cccacccaag cacacgctga gccgtgtcat   2340
ggtgtccaag gcccgaggca aggaccggct gtggagccac acgcgggaac cgctcaagca   2400
ggcgctgctc aagaagctcc tgggcagtga ggagctctcg caggaggcct gcctggcctt   2460
cattgctgtg ctcaagtaca tgggcgacta cccgtccaag aggacacgct ccgtcaatga   2520
```

gctcaccgac cagatctttg agggtcccct gaaagccgag cccctgaagg acgaggcata 2580 tgtgcagatc ctgaagcagc tgaccgacaa ccacatcagg tacagcgagg agcggggttg 2640 ggagctgctc tggctgtgca cgggcctttt cccacccagc aacatcctcc tgccccacgt 2700 gcagcgcttc ctgcagtccc gaaagcactg cccactcgcc atcgactgcc tgcaacggct 2760 ccagaaagcc ctgagaaacg ggtcccggaa gtaccctccg cacctggtgg aggtggaggc 2820 catccagcac aagaccaccc agattttcca caaggtctac ttccctgatg acactgacga 2880 ggccttcgaa gtggagtcca gcaccaaggc caaggacttc tgccagaaca tcgccaccag 2940 gctgctcctc aagtcctcag agggattcag cctctttgtc aaaattgcag acaaggtcat 3000 cagcgttcct gagaatgact tcttctttga ctttgttcga cacttgacag actggataaa 3060 gaaagctcgg cccatcaagg acggaattgt gccctcactc acctaccagg tgttcttcat 3120 gaagaagctg tggaccacca cggtgccagg gaaggatccc atggccgatt ccatcttcca 3180 ctattaccag gagttgccca agtatctccg aggctaccac aagtgcacgc gggaggaggt 3240 gctgcagctg ggggcgctga tctacagggt caagttcgag gaggacaagt cctacttccc 3300 cagcatcccc aagctgctgc gggagctggt gccccaggac cttatccggc aggtctcacc 3360 tgatgactgg aagcggtcca tcgtcgccta cttcaacaag cacgcaggga agtccaagga 3420 ggaggccaag ctggccttcc tgaagctcat cttcaagtgg cccacctttg gctcagcctt 3480 cttcgaggtg aagcaaacta cggagccaaa cttccctgag atcctcctaa ttgccatcaa 3540 caagtatggg gtcagcctca tcgatcccaa aacgaaggat atcctcacca ctcatccctt 3600 caccaagatc tccaactgga gcagcggcaa cacctacttc cacatcacca ttgggaactt 3660 ggtgcgcggg agcaaactgc tctgcgagac gtcactgggc tacaagatgg atgacctcct 3720 gacttcctac attagccaga tgctcacagc catgagcaaa cagcggggct ccaggagcgg 3780 caagtgaccg cggcctgctg ccggctctgc ggcctcttcc gcgtcttcga gatctgcctc 3840 gactgtgcct tctagttgcc agccatctgt tgtttgcccc tcccccgtgc cttccttgac 3900 cctggaaggt gccactccca ctgtcctttc ctaataaaat gaggaaattg catcgcattg 3960 tctgagtagg tgtcattcta ttctgggggg tggggtgggg caggacagca agggggagga 4020 ttgggaagac aatagcaggc atgctgggga ctcgagttaa gggcgcaatt cccgattagg 4080 atcttcctag agcatggcta cgtagataag tagcatggcg ggttaatcat taactacaag 4140 gaacccctag tgatggagtt ggccactccc tctctgcgcg ctcgctcgct cactgaggcc 4200 gggcgaccaa aggtcgcccg acgcccgggc tttgcccggg cggcctcagt gagcgagcga 4260 gcgcgcag 4268

<210> SEQ ID NO 29
<211> LENGTH: 278
<212> TYPE: DNA
<213> ORGANISM: Artificial Sequence
<220> FEATURE:
<223> OTHER INFORMATION: synthetic

<400> SEQUENCE: 29 gtgatcctag gtggaggccg aaagtacatg tttcgcatgg gaaccccaga ccctgagtac 60 ccagatgact acagccaagg tgggaccagg ctggacggga agaatctggt gcaggaatgg 120 ctggcgaagc gccagggtgc ccggtacgtg tggaaccgca ctgagctcat gcaggcttcc 180 ctggacccgt ctgtgaccca tctcatgggt ctctttgagc ctggagacat gaaatacgag 240 atccaccgag actccacact ggacccctcc ctgatgga 278

<210> SEQ ID NO 30
<211> LENGTH: 66
<212> TYPE: DNA
<213> ORGANISM: Artificial Sequence
<220> FEATURE:
<223> OTHER INFORMATION: synthetic

<400> SEQUENCE: 30 gactacaaag accatgacgg tgattataaa gatcatgaca tcgactacaa ggatgacgat 60 gacaag 66

<210> SEQ ID NO 31
<211> LENGTH: 30
<212> TYPE: DNA
<213> ORGANISM: Artificial Sequence
<220> FEATURE:
<223> OTHER INFORMATION: synthetic

<400> SEQUENCE: 31 atgtatgatg ttcctgatta tgctagcctc 30

<210> SEQ ID NO 32
<211> LENGTH: 27
<212> TYPE: DNA
<213> ORGANISM: Artificial Sequence
<220> FEATURE:
<223> OTHER INFORMATION: synthetic

<400> SEQUENCE: 32 tatccgtatg atgtgccgga ttatgcg 27

<210> SEQ ID NO 33
<211> LENGTH: 24
<212> TYPE: DNA
<213> ORGANISM: Artificial Sequence
<220> FEATURE:
<223> OTHER INFORMATION: synthetic

<400> SEQUENCE: 33 gtggagcttg acatctactt gacc 24

<210> SEQ ID NO 34
<211> LENGTH: 21
<212> TYPE: DNA
<213> ORGANISM: Artificial Sequence
<220> FEATURE:
<223> OTHER INFORMATION: synthetic

<400> SEQUENCE: 34 agctgaccct catgactctg c 21

The invention claimed is:

1. A dual construct system to express the coding sequence of a gene of interest in a host cell, said coding sequence consisting of a 5'end portion and of a 3'end portion, said dual construct system comprising:

a) a first plasmid comprising, in a 5'-3' direction:
- a 5'-inverted terminal repeat (5'-ITR) sequence;
- a promoter sequence;
- the 5' end portion of said coding sequence, said 5'end portion being operably linked to and under control of said promoter;

a nucleic acid sequence of a splicing donor signal; and a 3'-inverted terminal repeat (3'-ITR) sequence; and b) a second plasmid comprising, in a 5'-3' direction:
- a 5'-inverted terminal repeat (5'-ITR) sequence;
- a nucleic acid sequence of a splicing acceptor signal;
- the 3'end of said coding sequence;
- a poly-adenylation signal nucleic acid sequence;
- a 3'-inverted terminal repeat (3'-ITR) sequence;

wherein the nucleotide sequence of the respective ITRs is obtained from an adeno-associated virus (AAV) of the same AAV serotype or from an AAV of a different serotype;

wherein said first plasmid further comprises a nucleic acid sequence of a recombinogenic region in 5' position of the 3'ITR of said first plasmid, and wherein said second plasmid further comprises a nucleic acid sequence of a recombinogenic region in 3' position of the 5'-ITR of said second plasmid; and wherein the recombinogenic region is an F1 phage recombinogenic region that consists of the sequence:

(SEQ ID NO: 3)
GGGATTTTGCCGATTTCGGCCTATTGGTTAAAAAATGAGCTGATTTAACA

AAAATTTAACGCGAATTTTAACAAAAT.

2. The dual construct system according to claim 1, wherein upon introduction of said first plasmid and said second plasmid into the host cell, said coding sequence reconstitutes by means of the splicing donor and the splicing acceptor signals.

3. The dual construct system according to claim 1, wherein the 3'-ITR of the first plasmid and the 5'-ITR of the second plasmid are from the same AAV serotype.

4. The dual construct system according to claim 1, wherein the 5'-ITR and 3'-ITR of the first plasmid and the 5'-ITR and 3'-ITR of the second plasmid are respectively from different AAV serotypes.

5. The dual construct system according to claim 1, wherein the 5'-ITR of the first plasmid and the 3'-ITR of the second plasmid are from different AAV serotypes.

6. The dual construct system according to claim 1, wherein the coding sequence is split into the 5' end portion and the 3' end portion at a natural exon-exon junction.

7. The dual construct system according to claim 1, wherein the nucleic acid sequence of the splicing donor signal comprises the sequence:

(SEQ ID NO: 1)
GTAAGTATCAAGGTTACAAGACAGGTTTAAGGAGACCAATAGAAACTGGG

CTTGTCGAGACAGAGAAGACTCTTGCGTTTCT.

8. The dual construct system according to claim 1, wherein the nucleic acid sequence of the splicing acceptor signal comprises the sequence (SEQ ID NO: 2)
GATAGGCACCTATTGGTCTTACTGACATCCACTTTGCCTTTCTCTCCACA

G.

9. The dual construct system according to claim 1, wherein the first plasmid further comprises at least one enhancer sequence, operably linked to the coding sequence.

10. The dual construct system according to claim 1, wherein the coding sequence is a nucleotide sequence encoding a protein able to correct an inherited retinal degeneration.

11. The dual construct system according to claim 10, wherein the coding sequence is selected from the group consisting of: ABCA4, MYO7A, CEP290, CDH23, EYS, USH2a, GPR98 and ALMS1.

12. A dual viral vector system comprising:

a) a first viral vector containing the first plasmid, and b) a second viral vector containing the second plasmid, wherein said first and said second plasmids are as defined in claim 1, and wherein the vectors are adeno-associated virus (AAV) vectors.

13. The dual viral vector system according to claim 12, wherein the adeno-associated virus (AAV) vectors are the same or different AAV serotypes.

14. The dual viral vector system according to claim 12, wherein the AAV vectors have a serotype selected from the group consisting of serotype 2, serotype 8, serotype 5, serotype 7 and serotype 9.

15. An isolated host cell transformed with the dual viral vector system according to claim 12.

16. A pharmaceutical composition comprising the dual construct system according to claim 1, and a pharmaceutically acceptable vehicle.

17. A method for treating a subject having a disease characterized by a retinal degeneration comprising subretinally administering to said subject an effective amount of the dual viral vector system according to claim 12.

18. A pharmaceutical composition comprising the dual viral vector system according to claim 12 and a pharmaceutically acceptable vehicle.

19. A pharmaceutical composition comprising the isolated host cell according to claim 15 and a pharmaceutically acceptable vehicle.

*20. A first polynucleotide comprising in a 5'-3' direction:*

*a 5'-inverted terminal repeat (5'-ITR) sequence;*

*a promoter sequence;*

*a 5' end portion of a coding sequence of a gene of interest, the 5' end portion being operably linked to and under control of the promoter sequence;*

*a nucleic acid sequence of a splicing donor signal;*

*a nucleic acid sequence of a recombinogenic region; and*

*a 3'-inverted terminal repeat (3'-ITR) sequence,*

*wherein the ITRs are adeno-associated virus (AAV) ITRs, and wherein the recombinogenic region is: (a) a Fl phage recombinogenic region that consists of the sequence:*

*(SEQ ID NO: 3)*
*GGGATTTTGCCGATTTCGGCCTATTGGTTAAAAAATGAGCTGATTTAACA*

*AAAATTTAACGCGAATTTTAACAAAAT;*

*or (b) a fragment of SEQ ID NO: 3 having at least 85% sequence identity thereto.*

21. The first polynucleotide of claim 20, capable of undergoing homologous recombination with a second polynucleotide that comprises the Fl phage recombinogenic region.

22. The first polynucleotide of claim 20, wherein:

the nucleotide sequence of the 5'-ITR and 3'-ITR are obtained from an AAV of the same AAV serotype or a different AAV serotype;

the nucleotide sequence of the 5'-ITR and 3'-ITR are obtained from AAV serotype 2;

the coding sequence is split into the 5' end portion at a natural exon-exon junction;

the nucleic acid sequence of the splicing donor signal comprises (SEQ ID NO: 1)
GTAAGTATCAAGGTTACAAGACAGGTTTAAGGAGACCAATAGAAACTGGG

CTTGTCGAGACAGAGAAGACTCTTGCGTTTCT;

the 5' end portion of the coding sequence of the gene of interest is 4.5 Kb, 5 Kb, 5.5 Kb, 6 Kb, or a smaller size; and/or the coding sequence is a nucleotide sequence encoding a protein able to correct an inherited retinal degeneration, optionally wherein the coding sequence is selected from the group consisting of the gene coding sequences of: ABCA4, MYO7A, CEP290, CDH23, EYS, USH2a, GPR98, and ALMS1.

23. The first polynucleotide of claim 20, wherein the promoter sequence is selected from the group consisting of a cytomegalovirus (CMV) promoter sequence, a chicken beta-actin (CBA) promoter sequence, a vitelliform macular dystrophy 2 (VMD2) promoter sequence, a interphotoreceptor retinoid binding protein promoter sequence, a rhodopsin (RHO) promoter sequence, and a rhodopsin kinase (RHOK) promoter sequence, optionally wherein the first polynucleotide further comprises at least one enhancer and/or intron sequence, operably linked to the coding sequence.

24. A first viral vector comprising the first polynucleotide of claim 20, optionally wherein the vector is an AAV vector, optionally wherein:

the adeno-associated virus is selected from serotype 2, serotype 8, serotype 5, serotype 7, and serotype 9; and/or the AAV vector is AAV2/8.

25. An isolated host cell transformed with the first viral vector of claim 24.

26. A pharmaceutical composition comprising the first viral vector of claim 24 and pharmaceutically acceptable vehicle, optionally wherein the pharmaceutical composition is administered to a subject via subretinal administration.

27. A second polynucleotide comprising in a 5'-3' direction:

a 5'-inverted terminal repeat (5'-ITR) sequence;

a nucleic acid sequence of a recombinogenic region;

a nucleic acid sequence of a splicing acceptor signal;

a 3' end portion of a coding sequence of a gene of interest;

a poly-adenylation signal nucleic acid sequence; and a 3'-inverted terminal repeat (3'-ITR) sequence, wherein the ITRs are adeno-associated virus (AAV) ITRs, and wherein the recombinogenic region is: (a) a Fl phage recombinogenic region that consists of the sequence:

(SEQ ID NO: 3)
GGGATTTTGCCGATTTCGGCCTATTGGTTAAAAAATGAGCTGATTTAACA

AAAATTTAACGCGAATTTTAACAAAAT;

or (b) a fragment of SEQ ID NO: 3 having at least 85% sequence identity thereto.

28. The second polynucleotide of claim 27, capable of undergoing homologous recombination with a first polynucleotide that comprises the Fl phage recombinogenic region.

29. The second polynucleotide of claim 27, wherein:

the nucleotide sequence of the 5'-ITR and 3'-ITR are obtained from an AAV of the same AAV serotype or a different AAV serotype;

the nucleotide sequence of the 5'-ITR and 3'-ITR are obtained from AAV serotype 2;

the coding sequence is split into the 3' end portion at a natural exon-exon junction;

the nucleic acid sequence of the splicing acceptor signal comprises (SEQ ID NO: 2)
GATAGGCACCTATTGGTCTTACTGACATCCACTTTGCCTTTCTCTCCACA

G;

the 3' end portion of the coding sequence of the gene of interest is 4.5 Kb, 5 Kb, 5.5 Kb, 6 Kb, or a smaller size; and/or the coding sequence is a nucleotide sequence encoding a protein able to correct an inherited retinal degeneration, optionally wherein the coding sequence is selected from the group consisting of the gene coding sequences of: ABCA4, MYO7A, CEP290, CDH23, EYS, USH2a, GPR98, and ALMS1.

30. The second polynucleotide of claim 27, wherein the poly-adenylation signal nucleic acid sequence comprises a bovine growth hormone (BGH) poly-adenylation signal or a simian virus 40 (SV40) poly-adenylation signal.

31. A second viral vector comprising the second polynucleotide of claim 27, optionally wherein the vector is an AAV vector, optionally wherein:

the adeno-associated virus is selected from serotype 2, serotype 8, serotype 5, serotype 7, and serotype 9; and/or the AAV vector is AAV2/8.

32. An isolated host cell transformed with the second viral vector of claim 31.

33. A pharmaceutical composition comprising the second viral vector of claim 31 and pharmaceutically acceptable vehicle, optionally wherein the pharmaceutical composition is administered to a subject via subretinal administration.

34. A dual construct system to express a coding sequence of a gene of interest in a host cell, the coding sequence having a 5' end portion and a 3' end portion, the dual construct system comprising:

a) a first polynucleotide comprising in a 5'-3' direction:

a 5'-inverted terminal repeat (5'-ITR) sequence;

a promoter sequence;

a 5' end portion of the coding sequence of the gene of interest, the 5' end portion being operably linked to and under control of the promoter sequence;

a nucleic acid sequence of a splicing donor signal;

a nucleic acid sequence of a recombinogenic region; and a 3'-inverted terminal repeat (3'-ITR) sequence,

*wherein the ITRs are adeno-associated virus (AAV) ITRs, and wherein the recombinogenic region is: (a) a Fl phage recombinogenic region that consists of the sequence:*

(SEQ ID NO. 3)
GGGATTTTGCCGATTTCGGCCTATTGGTTAAAAAATGAGCTGATTTAACA

AAAATTTAACGCGAATTTTAACAAAAT;

*or (b) a fragment of SEQ ID NO: 3 having at least 85% sequence identity thereto; and*

*b) a second polynucleotide comprising in a 5'-3' direction:*

*a 5'-inverted terminal repeat (5'-ITR) sequence;*

*a nucleic acid sequence of a recombinogenic region;*

*a nucleic acid sequence of a splicing acceptor signal;*

*a 3' end portion of the coding sequence of the gene of interest;*

*a poly-adenylation signal nucleic acid sequence; and*

*a 3'-inverted terminal repeat (3'-ITR) sequence,*

*wherein the ITRs are AAV ITRs, and wherein the recombinogenic region is: (a) a Fl phage recombinogenic region that consists of the sequence:*

(SEQ ID NO. 3)
GGGATTTTGCCGATTTCGGCCTATTGGTTAAAAAATGAGCTGATTTAACA

AAAATTTAACGCGAATTTTAACAAAAT;

*or (b) a fragment of SEQ ID NO: 3 having at least 85% sequence identity thereto.*

*35. The dual construct system of claim 34, wherein upon introduction of the first polynucleotide and the second polynucleotide into the host cell, the coding sequence reconstitutes by means of the splicing donor and the splicing acceptor signals.*

*36. The dual construct system of claim 34, wherein:*

*upon introduction of the first polynucleotide and the second polynucleotide into the host cell, the coding sequence reconstitutes by means of homologous recombination between the Fl phage recombinogenic region of the first polynucleotide and the Fl phage recombinogenic region of the second polynucleotide; or*

*upon introduction of the first polynucleotide and the second polynucleotide into the host cell, the coding sequence reconstitutes by means of ITR-mediated concatemerization; or*

*upon introduction of the first polynucleotide and the second polynucleotide into the host cell, the coding sequence reconstitutes by one or both of:*

*(i) ITR-mediated concatemerization; and*

*(ii) homologous recombination between the Fl phage recombinogenic region of the first polynucleotide and the Fl phage recombinogenic region of the second polynucleotide,*

*followed by splicing through the splicing donor and the splicing acceptor signals for the production of a mature mRNA.*

*37. The dual construct system of claim 34, wherein:*

*the 3'-ITR of the first polynucleotide and the 5'-ITR of the second polynucleotide are from the same AAV serotype;*

*the 5'-ITR and 3'-ITR of the first polynucleotide and the 5'-ITR and 3'-ITR of the second polynucleotide are respectively from different AAV serotypes;*

*the 5'-ITR of the first polynucleotide and the 3'-ITR of the second polynucleotide are from different AAV serotypes;*

*the nucleotide sequence of the 5'-ITR and 3'-ITR of the first polynucleotide and the second polynucleotide are obtained from AAV serotype 2;*

*the coding sequence is split into the 5' end portion and the 3' end portion at a natural exon-exon junction;*

*the nucleic acid sequence of the splicing donor signal comprises the sequence:*

(SEQ ID NO: 1)
GTAAGTATCAAGGTTACAAGACAGGTTTAAGGAGACCAATAGAAACTGGG

CTTGTCGAGACAGAGAAGACTCTTGCGTTTCT;

*the nucleic acid sequence of the splicing acceptor signal comprises the sequence*

(SEQ ID NO: 2)
GATAGGCACCTATTGGTCTTACTGACATCCACTTTGCCTTTCTCTCCACA

G;

*the 5' end portion of the coding sequence of the gene of interest is 4.5 Kb, 5 Kb, 5.5 Kb, 6 Kb, or a smaller size;*

*the 3' end portion of the coding sequence of the gene of interest is 4.5 Kb, 5 Kb, 5.5 Kb, 6 Kb, or a smaller size;*

*the first polynucleotide further comprises at least one enhancer and/or intron sequence, operably linked to the coding sequence; and/or*

*the coding sequence is a nucleotide sequence encoding a protein able to correct an inherited retinal degeneration, optionally wherein the coding sequence is selected from the group consisting of the gene coding sequences of: ABCA4, MYO7A, CEP290, CDH23, EYS, USH2a, GPR98, and ALMS1.*

*38. The dual construct system of claim 34, wherein:*

*the promoter sequence is selected from the group consisting of a cytomegalovirus (CMV) promoter sequence, a chicken beta-actin (CBA) promoter sequence, a vitelliform macular dystrophy 2 (VMD2) promoter sequence, a interphotoreceptor retinoid binding protein promoter sequence, a rhodopsin (RHO) promoter sequence, and a rhodopsin kinase (RHOK) promoter sequence; and/or*

*the poly-adenylation signal nucleic acid sequence comprises a bovine growth hormone (BGH) poly-adenylation signal or a simian virus 40 (SV40) poly-adenylation signal.*

*39. A dual viral vector system comprising: a) a first viral vector containing the first polynucleotide, and b) a second viral vector containing the second polynucleotide, wherein said first and said second polynucleotides are as defined in claim 34, and wherein the vectors are AAV vectors, optionally wherein:*

*the AAV vectors are the same or different AAV serotypes;*

*the AAV vectors have a serotype selected from the group consisting of serotype 2, serotype 8, serotype 5, serotype 7 and serotype 9;*

*the AAV vector is AAV2/8;*

*the dual viral vector system is capable of transducing one or both of retinal pigment epithelium and photoreceptors; and/or*

*the dual viral vector system is capable of inducing stronger expression of the gene of interest compared to a dual AAV trans-splicing vector system.*

*40. An isolated host cell transformed with the dual viral vector system according to claim 39.*

*41. A pharmaceutical composition comprising the dual viral vector system of claim 39, and a pharmaceutically*

*acceptable vehicle, optionally wherein the pharmaceutical composition is administered to a subject via subretinal administration.*

*42. A method for treating a subject having a disease characterized by a retinal degeneration comprising subretinally administering to the subject an effective amount of the dual viral vector system of claim 39, optionally wherein the disease characterized by a retinal degeneration is Usher 1B and the coding sequence is of a MYO7A gene.*

*43. A dual construct system to express a coding sequence of a gene of interest in an host cell, the coding sequence having a 5' end portion and a 3' end portion, the dual construct system comprising:*

*a) a first polynucleotide comprising in a 5'-3' direction:*

*a 5'-inverted terminal repeat (5'-ITR) sequence;*

*a chicken beta-actin (CBA) promoter sequence;*

*a 5' end portion of the coding sequence of a MYO7A gene, the 5' end portion being operably linked to and under control of the promoter sequence;*

*a nucleic acid sequence of a splicing donor signal;*

*a nucleic acid sequence of a recombinogenic region; and*

*a 3'-inverted terminal repeat (3'-ITR) sequence,*

*wherein the ITRs are adeno-associated virus (AAV) ITRs, and wherein the recombinogenic region is: (a) a Fl phage recombinogenic region that consists of the sequence:*

(SEQ ID NO. 3)
GGGATTTTGCCGATTTCGGCCTATTGGTTAAAAAATGAGCTGATTTAACA
AAAATTTAACGCGAATTTTAACAAAAT;

*or (b) a fragment of SEQ ID NO: 3 having at least 85% sequence identity thereto; and*

*b) a second polynucleotide comprising in a 5'-3' direction:*

*a 5'-inverted terminal repeat (5'-ITR) sequence;*

*a nucleic acid sequence of a recombinogenic region;*

*a nucleic acid sequence of a splicing acceptor signal;*

*a 3' end portion of the coding sequence of a MYO7A gene;*

*a bovine growth hormone (BGH) poly-adenylation signal nucleic acid sequence; and*

*a 3'-inverted terminal repeat (3'-ITR) sequence,*

*wherein the ITRs are AAV ITRs, and wherein the recombinogenic region is: (a) a Fl phage recombinogenic region that consists of the sequence:*

(SEQ ID NO. 3)
GGGATTTTGCCGATTTCGGCCTATTGGTTAAAAAATGAGCTGATTTAACA
AAAATTTAACGCGAATTTTAACAAAAT;

*or (b) a fragment of SEQ ID NO: 3 having at least 85% sequence identity thereto.*

*44. The dual construct system of claim 43, wherein:*

*upon introduction of the first polynucleotide and the second polynucleotide into the host cell, the coding sequence reconstitutes by means of the splicing donor and the splicing acceptor signals;*

*upon introduction of the first polynucleotide and the second polynucleotide into the host cell, the coding sequence reconstitutes by means of homologous recombination between the Fl phage recombinogenic region of the first polynucleotide and the Fl phage recombinogenic region of the second polynucleotide;*

*the 3'-ITR of the first polynucleotide and the 5'-ITR of the second polynucleotide are from the same AAV serotype;*

*the 5'-ITR and 3'-ITR of the first polynucleotide and the 5'-ITR and 3'-ITR of the second polynucleotide are respectively from different AAV serotypes;*

*the 5'-ITR of the first polynucleotide and the 3'-ITR of the second polynucleotide are from different AAV serotypes;*

*the nucleotide sequence of the 5'-ITR and 3'-ITR of the first polynucleotide and the second polynucleotide are obtained from AAV serotype 2;*

*the coding sequence is split into the 5' end portion and the 3' end portion at a natural exon-exon junction;*

*the MYO7A coding sequence is split between exons 24-25;*

*the nucleic acid sequence of the splicing donor signal comprises the sequence:*

(SEQ ID NO: 1)
GTAAGTATCAAGGTTACAAGACAGGTTTAAGGAGACCAATAGAAACTGGG
CTTGTCGAGACAGAGAAGACTCTTGCGTTTCT;

*the nucleic acid sequence of the splicing acceptor signal comprises the sequence*

(SEQ ID NO: 2)
GATAGGCACCTATTGGTCTTACTGACATCCACTTTGCCTTTCTCTCCACA
G;

*and/or*

*the first polynucleotide further comprises at least one enhancer and/or intron sequence, operably linked to the coding sequence.*

*45. A dual viral vector system comprising: a) a first viral vector containing the first polynucleotide, and b) a second viral vector containing the second polynucleotide, wherein said first and said second polynucleotides are as defined in claim 43, and wherein the vectors are AAV vectors, optionally wherein:*

*the AAV vectors are the same or different AAV serotypes;*

*the AAV vectors have a serotype selected from the group consisting of serotype 2, serotype 8, serotype 5, serotype 7 and serotype 9; and/or*

*the AAV vector is AAV2/8.*

*46. The dual viral vector system of claim 45,*

*capable of transducing one or both of retinal pigment epithelium and photoreceptors;*

*capable of inducing stronger expression of MYO7A compared to a dual AAV trans-splicing vector system; and/or*

*capable of transducing retina to a higher level compared to an oversized AAV vector system or a dual viral vector system comprising an alkaline phosphatase (AP) recombinogenic region.*

*47. An isolated host cell transformed with the dual viral vector system according to claim 45, optionally wherein the host cell is a human cell.*

*48. A pharmaceutical composition comprising the dual viral vector system of claim 45, and a pharmaceutically acceptable vehicle, optionally wherein the pharmaceutical composition is administered to a subject via subretinal administration.*

*49. A method for treating a subject having Usher 1B, comprising subretinally administering to the subject an effective amount of the dual viral vector system of claim 45.*

*50. A method for correctly localizing retinal pigment epithelium (RPE) melanosomes apically, comprising subretinally administering to the subject an effective amount of the dual viral vector system of claim 45.*

51. A method for reducing the accumulation of rhodopsin at the connecting cilium of photoreceptors, comprising subretinally administering to the subject an effective amount of the dual viral vector system of claim 45.

52. A method to induce genetic recombination in a host cell, the method comprising introducing into the host cell a dual construct system, wherein the dual construct system comprises:

a) a first polynucleotide comprising in a 5'-3' direction:
- a 5'-inverted terminal repeat (5'-ITR) sequence;
- a promoter sequence;
- a 5' end portion of a coding sequence of a gene of interest, the 5' end portion being operably linked to and under control of the promoter sequence;
- a nucleic acid sequence of a splicing donor signal;
- a nucleic acid sequence of a recombinogenic region; and
- a 3'-inverted terminal repeat (3'-ITR) sequence, wherein the ITRs are adeno-associated virus (AAV) ITRs, and wherein the recombinogenic region is: (a) a Fl phage recombinogenic region that consists of the sequence:

(SEQ ID NO. 3)
GGGATTTTGCCGATTTCGGCCTATTGGTTAAAAAATGAGCTGATTTAACA
AAAATTTAACGCGAATTTTAACAAAAT;

or (b) a fragment of SEQ ID NO: 3 having at least 85% sequence identity thereto; and b) a second polynucleotide comprising in a 5'-3' direction:
- a 5'-inverted terminal repeat (5'-ITR) sequence;
- a nucleic acid sequence of a recombinogenic region;
- a nucleic acid sequence of a splicing acceptor signal;
- a 3' end portion of a coding sequence of the gene of interest;
- a poly-adenylation signal nucleic acid sequence; and
- a 3'-inverted terminal repeat (3'-ITR) sequence, wherein the ITRs are AAV ITRs, and wherein the recombinogenic region is: (a) a Fl phage recombinogenic region that consists of the sequence:

(SEQ ID NO. 3)
GGGATTTTGCCGATTTCGGCCTATTGGTTAAAAAATGAGCTGATTTAACA
AAAATTTAACGCGAATTTTAACAAAAT;

or (b) a fragment of SEQ ID NO: 3 having at least 85% sequence identity thereto.

53. The method of claim 52, wherein:

upon introduction of the first polynucleotide and the second polynucleotide into the host cell, the coding sequence reconstitutes by means of the splicing donor and the splicing acceptor signals; and/or upon introduction of the first polynucleotide and the second polynucleotide into the host cell, the coding sequence reconstitutes by means of homologous recombination between the Fl phage recombinogenic region of the first polynucleotide and the Fl phage recombinogenic region of the second polynucleotide.

54. A method for reconstituting a coding sequence in a host cell, the method comprising introducing into the host cell a dual construct system, wherein the dual construct system comprises:

a) a first polynucleotide comprising in a 5'-3' direction:
- a 5'-inverted terminal repeat (5'-ITR) sequence;
- a promoter sequence;
- a 5' end portion of a coding sequence of a gene of interest, the 5' end portion being operably linked to and under control of the promoter sequence;
- a nucleic acid sequence of a splicing donor signal;
- a nucleic acid sequence of a recombinogenic region; and
- a 3'-inverted terminal repeat (3'-ITR) sequence, wherein the ITRs are adeno-associated virus (AAV) ITRs, and wherein the recombinogenic region is: (a) a Fl phage recombinogenic region that consists of the sequence:

(SEQ ID NO. 3)
GGGATTTTGCCGATTTCGGCCTATTGGTTAAAAAATGAGCTGATTTAACA
AAAATTTAACGCGAATTTTAACAAAAT;

or (b) a fragment of SEQ ID NO: 3 having at least 85% sequence identity thereto; and b) a second polynucleotide comprising in a 5'-3' direction:
- a 5'-inverted terminal repeat (5'-ITR) sequence;
- a nucleic acid sequence of a recombinogenic region;
- a nucleic acid sequence of a splicing acceptor signal;
- a 3' end portion of a coding sequence of the gene of interest;
- a poly-adenylation signal nucleic acid sequence; and
- a 3'-inverted terminal repeat (3'-ITR) sequence, wherein the ITRs are AAV ITRs, and wherein the recombinogenic region is: (a) a Fl phage recombinogenic region that consists of the sequence:

(SEQ ID NO. 3)
GGGATTTTGCCGATTTCGGCCTATTGGTTAAAAAATGAGCTGATTTAACA
AAAATTTAACGCGAATTTTAACAAAAT;

or (b) a fragment of SEQ ID NO: 3 having at least 85% sequence identity thereto.

55. A dual viral vector system comprising:

a) a first viral vector comprising in a 5'-3' direction:
- a 5'-inverted terminal repeat (5'-ITR) sequence;
- a promoter sequence;
- a 5' end portion of a coding sequence of a gene of interest, the 5' end portion being operably linked to and under control of the promoter sequence;
- a nucleic acid sequence of a splicing donor signal;
- a nucleic acid sequence of a recombinogenic region; and
- a 3'-inverted terminal repeat (3'-ITR) sequence, wherein the ITRs are adeno-associated virus (AAV) ITRs, and wherein the recombinogenic region is: (a) a Fl phage recombinogenic region that consists of the sequence:

(SEQ ID NO. 3)
GGGATTTTGCCGATTTCGGCCTATTGGTTAAAAAATGAGCTGATTTAACA
AAAATTTAACGCGAATTTTAACAAAAT;

or (b) a fragment of SEQ ID NO: 3 having at least 85% sequence identity thereto; and b) a second viral vector comprising in a 5'-3' direction:
- a 5'-inverted terminal repeat (5'-ITR) sequence;
- a nucleic acid sequence of a recombinogenic region;
- a nucleic acid sequence of a splicing acceptor signal;
- a 3' end portion of a coding sequence of the gene of interest;
- a poly-adenylation signal nucleic acid sequence; and
- a 3'-inverted terminal repeat (3'-ITR) sequence,

*wherein the ITRs are AAV ITRs, and wherein the recombinogenic region is: (a) a Fl phage recombinogenic region that consists of the sequence:*

(SEQ ID NO. 3)

GGGATTTTGCCGATTTCGGCCTATTGGTTAAAAAATGAGCTGATTTAACA

AAAATTTAACGCGAATTTTAACAAAAT;

*or (b) a fragment of SEQ ID NO: 3 having at least 85% sequence identity thereto.*

* * * * *